United States Patent
Weeks et al.

(10) Patent No.: US 9,918,441 B2
(45) Date of Patent: **\*Mar. 20, 2018**

(54) POTATO CULTIVAR V11

(71) Applicant: J.R. Simplot Company, Boise, ID (US)

(72) Inventors: Troy Weeks, Boise, ID (US); Craig Richael, Meridian, ID (US); Caius Rommens, Boise, ID (US); Hua Yan, Boise, ID (US); Jingsong Ye, Boise, ID (US)

(73) Assignee: J.R. Simplot Company, Boise, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/153,984

(22) Filed: May 13, 2016

(65) Prior Publication Data

US 2016/0330923 A1    Nov. 17, 2016

Related U.S. Application Data

(60) Provisional application No. 62/276,360, filed on Jan. 8, 2016, provisional application No. 62/161,732, filed on May 14, 2015.

(51) Int. Cl.
| | | |
|---|---|---|
| A01H 5/06 | (2006.01) | |
| A23L 19/18 | (2016.01) | |
| A23L 19/12 | (2016.01) | |
| A23L 19/15 | (2016.01) | |
| A23K 10/35 | (2016.01) | |

(52) U.S. Cl.
CPC ............... *A01H 5/06* (2013.01); *A23L 19/12* (2016.08); *A23L 19/15* (2016.08); *A23L 19/18* (2016.08); *A23K 10/35* (2016.05); *A23V 2002/00* (2013.01)

(58) Field of Classification Search
None
See application file for complete search history.

(56) References Cited

U.S. PATENT DOCUMENTS

| | | | |
|---|---|---|---|
| 5,510,253 A | 4/1996 | Mitsky et al. | |
| 6,160,204 A | 12/2000 | Steffens | |
| 6,855,669 B2 | 2/2005 | Knowles et al. | |
| 7,122,719 B2 | 10/2006 | Hakimi | |
| 7,250,554 B2 | 7/2007 | Rommens et al. | |
| 7,534,934 B2 | 5/2009 | Rommens et al. | |
| 7,619,138 B2 | 11/2009 | Rommens et al. | |
| 7,713,735 B2 | 5/2010 | Rommens et al. | |
| 7,880,057 B2 | 2/2011 | Rommens et al. | |
| 7,947,868 B2 | 5/2011 | Rommens et al. | |
| 8,143,477 B2 | 3/2012 | Rommens | |
| 8,158,414 B2 | 4/2012 | Rommens et al. | |
| 8,193,412 B2 | 6/2012 | Rommens et al. | |
| 8,252,974 B2 | 8/2012 | Rommens | |
| 8,273,949 B2 | 9/2012 | Rommens et al. | |
| 8,502,027 B2 | 8/2013 | Rommens | |
| 8,674,177 B2 | 3/2014 | Rommens et al. | |
| 8,710,311 B1* | 4/2014 | Clark | 435/419 |
| 8,754,303 B1* | 6/2014 | Clark | 435/419 |
| 8,889,963 B1* | 11/2014 | Clark | 435/419 |
| 8,889,964 B1* | 11/2014 | Clark | A23L 1/216 435/419 |
| 9,328,352 B2* | 5/2016 | Richael | C12N 15/8279 |
| 2009/0220670 A1 | 9/2009 | Rommens et al. | |
| 2010/0199386 A1 | 8/2010 | Bhaskar et al. | |
| 2011/0099656 A1 | 4/2011 | Rockey et al. | |
| 2011/0107470 A1 | 5/2011 | Rommens | |
| 2011/0145943 A1 | 6/2011 | Hoopes | |
| 2011/0231949 A1 | 9/2011 | Hoopes | |
| 2012/0102589 A1 | 4/2012 | Rommens | |
| 2012/0144902 A1 | 6/2012 | Torres-ordonez et al. | |
| 2013/0074222 A1 | 3/2013 | Rommens et al. | |
| 2014/0328994 A1 | 11/2014 | Richael et al. | |

(Continued)

FOREIGN PATENT DOCUMENTS

| | | |
|---|---|---|
| JP | 2009-508526 A | 3/2009 |
| WO | WO 1994/003607 A1 | 2/1994 |

(Continued)

OTHER PUBLICATIONS

Liu et al. Physicochemical properties of starches during potato growth. (2003) Carbohydrate Polymers; vol. 51; pp. 213-221.*
Chinese Patent Application No. 201380076275.7, Search Report (English translation) dated Sep. 13, 2016, 2 pages.
European Patent Application No. EP 13883574.9, Extended European Search Report dated Nov. 25, 2016, 10 pages.
European Patent Application No. EP 13883638.2, Extended European Search Report dated Nov. 25, 2016, 10 pages.
European Patent Application No. EP 14791173.9, Extended European Search Report dated Nov. 25, 2016, 10 pages.

(Continued)

*Primary Examiner* — Cathy Kingdon Worley
(74) *Attorney, Agent, or Firm* — Cooley LLP

(57) ABSTRACT

A potato cultivar designated V11 is disclosed. The invention relates to the tubers of potato cultivar V11, to the seeds of potato cultivar V11, to the plants of potato V11, to the plant parts of potato cultivar V11, to food products produced from potato cultivar V11, and to methods for producing a potato plant produced by crossing potato cultivar V11 with itself or with another potato variety. The invention also relates to methods for producing a potato plant containing in its genetic material one or more transgenes and to the transgenic potato plants and plant parts produced by those methods. This invention also relates to potato cultivars or breeding cultivars and plant parts derived from potato variety V11, to methods for producing other potato cultivars, lines or plant parts derived from potato cultivar V11 and to the potato plants, varieties, and their parts derived from use of those methods. The invention further relates to hybrid potato tubers, seeds, plants and plant parts produced by crossing potato cultivar V11 with another potato cultivar.

29 Claims, 25 Drawing Sheets

(56) References Cited

U.S. PATENT DOCUMENTS

| | | | |
|---|---|---|---|
| 2016/0073600 A1* | 3/2016 | Richael | C12N 15/8279 800/263 |
| 2016/0073601 A1 | 3/2016 | Richael et al. | |
| 2016/0073602 A1 | 3/2016 | Richael et al. | |
| 2016/0095286 A1 | 4/2016 | Richael et al. | |
| 2016/0102371 A1 | 4/2016 | Ye et al. | |
| 2017/0099793 A1 | 4/2017 | Richael et al. | |
| 2017/0099794 A1 | 4/2017 | Richael et al. | |
| 2017/0150689 A1 | 6/2017 | Richael et al. | |

FOREIGN PATENT DOCUMENTS

| | | |
|---|---|---|
| WO | WO 2002/061101 A2 | 8/2002 |
| WO | WO 2003/069980 A2 | 8/2003 |
| WO | WO 2004/040999 A1 | 5/2004 |
| WO | WO 2007/035752 A2 | 3/2007 |
| WO | WO 2010/091018 A1 | 8/2010 |
| WO | WO 2014/178910 A1 | 11/2014 |
| WO | WO 2014/178913 A1 | 11/2014 |
| WO | WO 2014/178941 A1 | 11/2014 |
| WO | WO 2014/179276 A1 | 11/2014 |
| WO | WO 2015/195090 A1 | 12/2015 |
| WO | WO 2016/057874 A1 | 4/2016 |
| WO | WO 2016/183445 A1 | 11/2016 |
| WO | WO 2017/062831 A1 | 4/2017 |

OTHER PUBLICATIONS

Foster, Simon J., et al. "Rpi-vnt1. 1, a Tm-22 homolog from Solanum venturii, confers resistance to potato late blight." Molecular Plant-Microbe Interactions (2009); 22.5: 589-600.

PCT/US2014/042631, International Search Report and Written Opinion dated Jan. 2, 2015, 14 pages.

PCT/US2014/042631, International Preliminary Report on Patentability dated Dec. 20, 2016, 10 pages.

GenBank Accession HM363754, "Solanum verrucosum polyphenol oxidase 5 mRNA, 3' UTR." (2010); Downloaded Jun. 20, 2017, 1 page https://www.ncbi.nlm.nih.gov/nuccore/308743331?sat=4&satkey=45811437.

GenBank Accession AY566556, "Solanum tuberosum polyphenol oxidase mRNA, 3' UTR." (2004); Downloaded Jun. 20, 2017, 1 page https://www.ncbi.nlm.nih.gov/nuccore/AY566556.

Rommens, et al., "Crop improvement through modification of the plant's own genome." Plant Physiology (2004); 135: 421-431; Retracted Apr. 2, 2013 (Retractions, 135: 421-431, 2004 and Addenda 139: 1338-1349, 2005).

Chawla et al., Tuber-specific silencing of asparagine synthetase-1 reduces the acrylamide-forming potential of potatoes grown in the field without affecting tuber shape and yield. Plant Biotechnol J. (2012); 10(8):913-924.

Cheng et al., "Effect of Different Varities of Potatoes on Acrylamide in Fresh-cut Fried Chips," Food Science (2011); 32(7): 411-414.

Coetzer et al., "Control of enzymatic browning in potato (Solanum tuberosum L.) by sense and antisense RNA from tomato polyphenol oxidase", J. Agric. Food Chem. (2001); vol. 49, pp. 652-657.

J.R. Simplot Co.; "Petition for Determination of Nonregulated Status for InnateTM Potatoes with Low Acrylamide Potential and Reduced Black Spot Bruise: Events E12 and E24 (Russet Burbank); F10 and F37 (Ranger Russet); J3, J55, and J78 (Atlantic); G11 (G); H37and H50 (H)," Received by APHIS on Mar. 5, 2013, published on May 3, 2013, https://www.aphis.usda.gov/brs/aphisdocs/13_02201p.pdf.

Richael, et al., "Employment of cytokinin vectors for marker-free and backbone-free transformation", Methods Mol Biol (2012); 847: 3-10.

Richael, et al., "Cytokinin vectors mediate marker-free and backbone-free plant transformation", Transgenic Res. (2008); 17: 905-917.

Ritte et al., "The starch-related R1 protein is an α-glucan, water dikinase", PNAS (2002); 99: 7166-7171.

Rommens et al., "The intragenic approach as a new extension to traditional plant breeding", Trends in Plant Science (2007); 12(9): 397-403.

Rommens et al., "Low-acrylamide French fries and potato chips", Plant Biotechnology Journal (2008); 6(8): 843-853.

Rommens, C.M., "All-native DNA transformation: a new approach to plant genetic engineering", Trends in Plant Science (2004), 9(9): 457-464.

Rommens, C.M., "Chapter 4: Precise breeding through all-native DNA transformation in Genetic Modification of Plants", Biotechnology in Agriculture and Forestry 64 (2010); F. Kempken and C. Jung (eds), Springer-Verlag, Berlin Heidelberg.

Rommens, C.M., "Intragenic crop improvement: combining the benefits of traditional breeding and genetic engineering", J. Agric. Food Chem. (2007); 55(11): 4281-4288.

Rommens, et al., "Improving potato storage and processing characteristics through all-native DNA transformation", J. Agric. Food Chem. (2006), 54(26): 9882-9887.

Rommens, et al., Intragenic vectors and marker-free transformation: Tools for a greener biotechnology, in Plant Transformation Technologies (2010); (eds C.N. Stewart, A. Touraev, V. Citovsky and T. Tzfira), Wiley-Blackwell, Oxford, UK.

Rommens, et al., "Plant-derived transfer DNAs", Plant Physiology (2005), 139: 1338-1349.

Rommens, et al., "Tastier and healthier alternatives to French fries", J Food Sci (2010); 75(4): H109-15.

Sonnewald et al. "A second L-type isozyme of potato glucan phosphorylase: cloning, antisense inhibition and expression analysis", Plant Molecular Biology (1995); 27: 567-576.

Yan, et al., "New construct approaches for efficient gene silencing in plants", Plant Physiology (2006); 141: 1508-1518.

Ye, et al. "Tuber-specific silencing of the acid invertase gene substantially lowers the acrylamide-forming potential of potato", J Agric Food Chem (2010); 58(23): 12162-12167.

Chinese Patent Application No. 201480024969.0, Search Report dated May 25, 2016, 3 pages.

PCT/US2013/068543, International Search Report and Written Opinion dated Mar. 11, 2014, 10 pages.

PCT/US2013/068543, International Preliminary Report on Patentability dated Nov. 3, 2015, 4 pages.

PCT/US2013/072191, International Search Report and Written Opinion dated Feb. 12, 2014, 6 pages.

PCT/US2013/072191, International Preliminary Report on Patentability dated Nov. 3, 2015, 5 pages.

PCT/US2014/018161, International Search Report and Written Opinion dated May 22, 2014, 6 pages.

PCT/US2014/018161, International Preliminary Report on Patentability dated Nov. 3, 2015, 5 pages.

PCT/US2014/035809, International Search Report and Written Opinion dated Sep. 23, 2014, 10 pages.

PCT/US2014/035809, International Preliminary Report on Patentability dated Nov. 3, 2015, 9 pages.

PCT/US2016/032359, International Search Report and Written Opinion dated Aug. 18, 2016, 8 pages.

Budapest Certificate of Deposit, Budapest Treaty on the International Recognition of the Deposit of Microogranisms for the Purposes of Patent Procedure International Form, The American Type Culture Collection (ATCC), date of receipt of deposit Jun. 17, 2015, ATCC Designation—PTA-122246, V11 (Snowden Event), Viability Tested and Verified Dec. 15, 2015, 2 pages.

Adang, Michael J., et al., "The reconstruction and expression of a Bacillus thuringiensis cryIIIA gene in protoplasts and potato plants." Plant Molecular Biology (1993); 21: 1131-1145.

Firko, M.J. "Preliminary Extended Determination1 of Nonregulated Status for JR Simplot 1-29 Company X17 and Y9 Potato Varieties with Late Blight Resistance, Low Acrylamide Potential, Lowered Reducing Sugars, and Reduced Black Spot (Petition No. 16-064-01 p)," U.S. Department of Agriculture, Sep. 22, 2016 (Sep. 22, 2016), pp. 1-17. Retrieved from the Internet:<www.aphis.usda.gov/brs/aphisdocs/16_06401 p_pdet_pprsa.pdf> on Nov. 20, 2016 (Nov. 20, 2016). entire document.

(56) References Cited

OTHER PUBLICATIONS

Kamrani et al. "Cisgenic inhibition of the potato cold induced phosphorylase L gene expression and decrease in sugar contents," African Journal of Biotechnology (2011); 10(50): 10076-10082.
Zhu et al. "Silencing of vacuolar invertase and asparagine synthetase genes and its impact on acrylamide formation of fried potato products," Plant Biotechnology Journal (2015); 14: 709-718.
PCT/US2016/056080, International Search Report and Written Opinion dated Dec. 19, 2016, 7 pages.
PCT/US2016/056086, International Search Report and Written Opinion dated Dec. 9, 2016, 7 pages.
Brummell et al. "Induction of vacuolar invertase inhibitor mRNA in potato tubers contributes to cold-induced sweetening resistance and includes spliced hybrid mRNA variants." J. of Exp. Botany (2011); 62(10): 3519-3534.
Zhu et al., "Functional stacking of three resistance genes against Phytophthora infestans in potato." Transgenic Research (2012); 21(1): 89-99.

\* cited by examiner

```
                         SEQUENCE LISTING

<160> NUMBER OF SEQ ID NOS: 22

<210> SEQ ID NO 1
  <211> LENGTH: 24
  <212> TYPE: DNA
  <213> ORGANISM: artificial
  <220> FEATURE:
  <223> OTHER INFORMATION: BB1 forward primer

<400> SEQUENCE: 1
actagttgtg aataagtcgc tgtg                                          24

<210> SEQ ID NO 2
  <211> LENGTH: 23
  <212> TYPE: DNA
  <213> ORGANISM: artificial
  <220> FEATURE:
  <223> OTHER INFORMATION: BB1 reverse primer

<400> SEQUENCE: 2
atcggaatcg actaacagaa cat                                           23

<210> SEQ ID NO 3
  <211> LENGTH: 21
  <212> TYPE: DNA
  <213> ORGANISM: artificial
  <220> FEATURE:
  <223> OTHER INFORMATION: BB2 forward primer

<400> SEQUENCE: 3
ccggggccga tgttctgtta g                                             21

<210> SEQ ID NO 4
  <211> LENGTH: 20
  <212> TYPE: DNA
  <213> ORGANISM: artificial
  <220> FEATURE:
  <223> OTHER INFORMATION: BB2 reverse primer

<400> SEQUENCE: 4
gctcgccggc agaacttgag                                               20

<210> SEQ ID NO 5
  <211> LENGTH: 20
  <212> TYPE: DNA
  <213> ORGANISM: artificial
  <220> FEATURE:
  <223> OTHER INFORMATION: BB3 forward primer

<400> SEQUENCE: 5
gccgcgtgtt ccgtccacac                                               20
```

<210> SEQ ID NO 6
<211> LENGTH: 20
<212> TYPE: DNA
<213> ORGANISM: artificial
<220> FEATURE:
<223> OTHER INFORMATION: BB3 reverse primer

<400> SEQUENCE: 6
cctgtcgggt ttcgccacct                                           20

<210> SEQ ID NO 7
<211> LENGTH: 20
<212> TYPE: DNA
<213> ORGANISM: artificial
<220> FEATURE:
<223> OTHER INFORMATION: BB4 forward primer

<400> SEQUENCE: 7
caagtcagag gtggcgaaac                                           20

<210> SEQ ID NO 8
<211> LENGTH: 23
<212> TYPE: DNA
<213> ORGANISM: artificial
<220> FEATURE:
<223> OTHER INFORMATION: BB4 reverse primer

<400> SEQUENCE: 8
ctttatgctc attgggttga gta                                       23

<210> SEQ ID NO 9
<211> LENGTH: 23
<212> TYPE: DNA
<213> ORGANISM: artificial
<220> FEATURE:
<223> OTHER INFORMATION: BB5 forward primer

<400> SEQUENCE: 9
agtccacccg aaatataaac aac                                       23

<210> SEQ ID NO 10
<211> LENGTH: 24
<212> TYPE: DNA
<213> ORGANISM: artificial
<220> FEATURE:
<223> OTHER INFORMATION: BB5 reverse primer

<400> SEQUENCE: 10
ggtatggacc tgcatctaat tttc                                      24

<210> SEQ ID NO 11
<211> LENGTH: 23
<212> TYPE: DNA
<213> ORGANISM: artificial
<220> FEATURE:
<223> OTHER INFORMATION: BB6 forward primer

<400> SEQUENCE: 11
gctctaatat agcgcatttc aag                                       23

<210> SEQ ID NO 12
<211> LENGTH: 22
<212> TYPE: DNA
<213> ORGANISM: artificial
<220> FEATURE:

<223> OTHER INFORMATION: BB6 reverse primer

<400> SEQUENCE: 12
gcttccagcc agccaacagc tc                                              22

<210> SEQ ID NO 13
<211> LENGTH: 27
<212> TYPE: DNA
<213> ORGANISM: artificial
<220> FEATURE:
<223> OTHER INFORMATION: BB7 forward primer

<400> SEQUENCE: 13
ctattttttt actatattat actcaac                                         27

<210> SEQ ID NO 14
<211> LENGTH: 26
<212> TYPE: DNA
<213> ORGANISM: artificial
<220> FEATURE:
<223> OTHER INFORMATION: BB7 reverse primer

<400> SEQUENCE: 14
ttttaatgtt tagcaaatgt cttatc                                          26

<210> SEQ ID NO 15
<211> LENGTH: 23
<212> TYPE: DNA
<213> ORGANISM: artificial
<220> FEATURE:
<223> OTHER INFORMATION: BB8 forward primer

<400> SEQUENCE: 15
gatccacctc cacgtagacg gag                                             23

<210> SEQ ID NO 16
<211> LENGTH: 23
<212> TYPE: DNA
<213> ORGANISM: artificial
<220> FEATURE:
<223> OTHER INFORMATION: BB8 reverse primer

<400> SEQUENCE: 16
gaaatgcgct atattagagc ata                                             23

<210> SEQ ID NO 17
<211> LENGTH: 21
<212> TYPE: DNA
<213> ORGANISM: artificial
<220> FEATURE:
<223> OTHER INFORMATION: JY719 LB PCR primer

<400> SEQUENCE: 17
gagctgttgg ctggctggaa g                                               21

<210> SEQ ID NO 18
<211> LENGTH: 23
<212> TYPE: DNA
<213> ORGANISM: artificial
<220> FEATURE:
<223> OTHER INFORMATION: JY718 LB PCR primer

<400> SEQUENCE: 18
gttggaaatc aattatcact gag                                             23

```
<210> SEQ ID NO 19
<211> LENGTH: 20
<212> TYPE: DNA
<213> ORGANISM: artificial
<220> FEATURE:
<223> OTHER INFORMATION: JY1029 LB PCR primer

<400> SEQUENCE: 19
ccgttcttcc gaatagcatc                                                    20

<210> SEQ ID NO 20
<211> LENGTH: 20
<212> TYPE: DNA
<213> ORGANISM: artificial
<220> FEATURE:
<223> OTHER INFORMATION: JY1030 LB PCR primer

<400> SEQUENCE: 20
cgggttatcg gttcttaacg                                                    20

<210> SEQ ID NO 21
<211> LENGTH: 24
<212> TYPE: DNA
<213> ORGANISM: artificial
<220> FEATURE:
<223> OTHER INFORMATION: JY725 RB PCR primer

<400> SEQUENCE: 21
gcttcccgta tacaacataa catg                                               24

<210> SEQ ID NO 22
<211> LENGTH: 24
<212> TYPE: DNA
<213> ORGANISM: artificial
<220> FEATURE:
<223> OTHER INFORMATION: JY726 RB PCR primer

<400> SEQUENCE: 22
gatctcaaac aaacatacac agcg                                               24
```

POTATO CULTIVAR V11

CROSS-REFERENCE TO RELATED APPLICATIONS

The present application claims the benefit of priority to U.S. Provisional Application No. 62/161,732, filed on May 14, 2015, and U.S. Provisional Application No. 62/276,360, filed on Jan. 8, 2016, the entire contents of each of which are hereby incorporated by reference in their entirety for all purposes.

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is JRSI-074_01US_ST25.txt. The text file is about 4 KB, was created on Jan. 6, 2016, and is being submitted electronically via EFS-Web.

BACKGROUND OF THE INVENTION

The present invention relates to a novel potato cultivar designated V11 and to the tubers, plants, plant parts, tissue culture and seeds produced by that potato variety. The invention further relates to food products produced from potato cultivar V11, such as French fries, potato chips, dehydrated potato material, potato flakes and potato granules. All publications cited in this application are herein incorporated by reference.

The potato is the world's fourth most important food crop and by far the most important vegetable. Potatoes are currently grown commercially in nearly every state of the United States. Annual potato production exceeds 18 million tons in the United States and 300 million tons worldwide. The popularity of the potato derives mainly from its versatility and nutritional value. Potatoes can be used fresh, frozen or dried, or can be processed into flour, starch or alcohol. They contain complex carbohydrates and are rich in calcium, niacin and vitamin C.

The quality of potatoes in the food industry is adversely affected by two critical factors: (1) potatoes contain large amounts of asparagine, a non-essential free amino acid that is rapidly oxidized to form acrylamide, a carcinogenic product, upon frying or baking; and (2) potatoes are highly susceptible to enzymatic browning and discoloration, an undesirable event which happens when polyphenol oxidase leaks out from the damaged plastids of bruised potatoes. In the cytoplasm, the enzyme oxidizes phenols, which then rapidly polymerize to produce dark pigments. Tubers contain large amounts of phosphorylated starch, some of which is degraded during storage to produce glucose and fructose. These reducing sugars react with amino acids to form Maillard products including acrylamide when heated at temperatures above 120° C. Two enzymes involved in starch phosphorylation are water dikinase R1 and phosphorylase-L (R1 and PhL). Browning is also triggered non-enzymatically as a consequence of the partial degradation of starch into glucose and fructose.

Tubers with low acrylamide content, increased black spot bruise tolerance and lowered reducing sugars would be valuable for the potato industry. Thus, there is a need to develop potato varieties with reduced levels of toxic compounds but without the use of unknown or foreign nucleic acids. The present invention satisfies this need.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary, not limiting in scope. In various embodiments, one or more of the above-described problems have been reduced or eliminated, while other embodiments are directed to other improvements.

To this end, the present invention provides novel potato variety V11 transformed with nucleic acid sequences that are native to the potato plant genome and does not contain foreign DNA, *Agrobacterium* DNA, viral markers or vector backbone sequences. Rather, the DNA inserted into the genome of the potato variety V11 is a non-coding polynucleotide native to potato or native to wild potato, a potato sexually-compatible plant, that silences genes involved in the expression of black spot bruises, asparagine accumulation and senescence sweetening.

Thus, in one embodiment, the present invention provides a plant vector, referred to as pSIM1278, that comprises a first silencing cassette containing two copies of a DNA segment comprising, in anti-sense orientation, a fragment of the asparagine synthetase-1 gene (Asn1) and the 3'-untranslated sequence of the polyphenol oxidase-5 gene; and a second silencing cassette containing two copies of a DNA segment comprising, in anti-sense orientation, a fragment of the promoter from the potato phosphorylase-L (pPhL) gene and a fragment of the promoter from the potato R1 gene. The pSIM1278 vector comprises a 9,512 bp backbone region that supports maintenance of the plant DNA prior to plant transformation and is not transferred into plant cells upon transformation of the plant cells, and a 10,148 bp DNA insert region comprising native DNA that is stably integrated into the genome of the plant cells upon transformation.

In a different embodiment, the invention provides a plant cell transformed with a plant vector of the invention. In a further embodiment, the invention provides a potato plant variety comprising one or more cells transformed with the vector of the invention. In one aspect of the invention, the potato plant variety expresses at least one of the two silencing cassettes of the vector pSIM1278, and expression of the silencing cassettes results in the down-regulation of the asparagine synthetase-1 gene and the polyphenol oxidase-5 gene in the tubers of the plant. In a preferred aspect of the invention, the tubers of the potato plant variety expressing at least one silencing cassette display two or more desirable traits that are not present in the tubers of untransformed plants of the same variety. In the most preferred aspect of the invention, the two or more desirable traits are selected from the group consisting of low asparagine accumulation, reduced black-spot bruising, reduced heat-induced acrylamide formation and reduced accumulation of reducing sugars during storage.

In a different aspect of the invention, the potato plant variety expresses both silencing cassettes of the plant DNA vector pSIM1278, and expression of the silencing cassettes results in the down-regulation of the asparagine synthetase-1 gene, the polyphenol oxidase-5 gene, the phosphorylase-L gene and the dikinase R1 gene in the tubers of the potato plant variety. In a preferred aspect of the invention, the tubers of the potato plant variety expressing two silencing cassettes of the plant DNA vector pSIM1278 display two or more desirable traits that are not present in the tubers of untransformed plants of the same variety. In a preferred embodiment, the two or more desirable traits are selected from the group consisting of low asparagine accumulation, reduced black-spot bruising, reduced accumulation of reducing sugars during storage and reduced heat-induced acrylamide formation. In one aspect of the invention, the potato plant variety expressing the two silencing cassettes of the plant DNA vector pSIM1278 is the Snowden V11 variety.

Thus, according to the invention, there is provided a new potato cultivar of the genus and species *Solanum tuberosum* L. designated V11. This invention thus relates to potato cultivar V11, to the tubers of potato cultivar V11, to the plants of potato cultivar V11, to the seeds of potato cultivar V11, to the food products produced from potato cultivar V11, and to methods for producing a potato plant produced by selfing potato cultivar V11 or by crossing potato cultivar V11 with another potato cultivar, and the creation of variants by mutagenesis or transformation of potato cultivar V11.

Thus, any such methods using the cultivar V11 are embodiments of this invention: selfing, backcrosses, hybrid production, crosses to populations, and the like. All plants produced using potato cultivar V11 as at least one parent are within the scope of this invention. Advantageously, the potato cultivar could be used in crosses with other, different, potato plants to produce first generation ($F_1$) potato hybrid tubers, seeds and plants with superior characteristics.

In another embodiment, the present invention provides for single or multiple gene converted plants of potato cultivar V11. In one embodiment, the transferred gene(s) may be a dominant or recessive allele(s). In some embodiments, the transferred gene(s) will confer such traits as herbicide resistance, insect resistance, resistance for bacterial, fungal, or viral disease, male fertility, male sterility, enhanced nutritional quality, uniformity, and increase in concentration of starch and other carbohydrates, decrease in tendency to bruise and decrease in the rate of conversion of starch to sugars. The gene(s) may be a naturally occurring potato gene or a transgene introduced through genetic engineering techniques, backcrossing or mutation.

In another embodiment, the present invention provides regenerable cells for use in tissue culture of potato cultivar V11. In one embodiment, the tissue culture will be capable of regenerating plants having all the physiological and morphological characteristics of the foregoing potato plant, and of regenerating plants having substantially the same genotype as the foregoing potato plant. In some embodiments, the regenerable cells in such tissue cultures will be embryos, protoplasts, meristematic cells, callus, pollen, leaves, anthers, pistils, cotyledons, hypocotyl, roots, root tips, flowers, seeds, petioles, tubers, eyes or stems. Still further, the present invention provides potato plants regenerated from tissue cultures of the invention.

In a further embodiment, the invention provides a food product made from a tuber of potato plant variety Snowden V11. Preferably, the food product is a heat-treated product. Even more preferably, the food product is a French fry, potato chip, dehydrated potato material, potato flakes, or potato granules.

In addition to the exemplary aspects and embodiments described above, further aspects and embodiments will become apparent by study of the following descriptions.

DETAILED DESCRIPTION OF THE INVENTION

Figure 1:
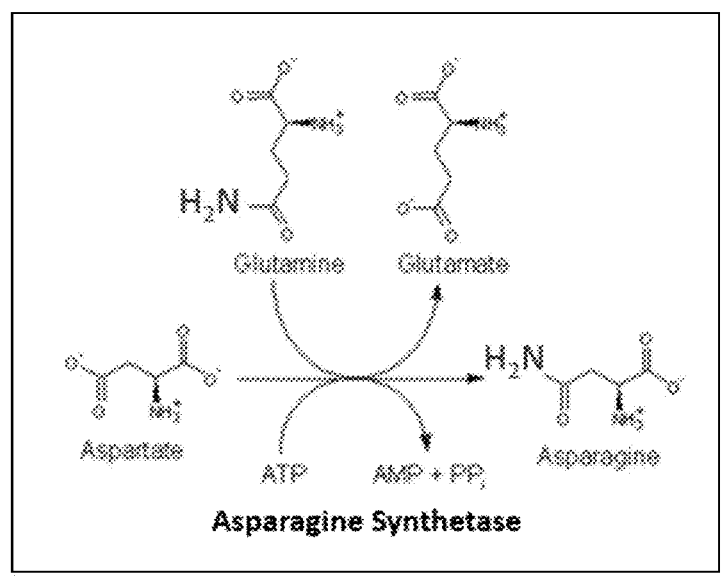
FIG. 1 depicts the pathway for biosynthesis of Asparagine in plants.

In the description and tables which follow, a number of terms are used. In order to provide a clear and consistent understanding of the specification and claims, including the scope to be given such terms, the following definitions are provided:

Allele. An allele is any of one or more alternative forms of a gene which relate to one trait or characteristic. In a diploid cell or organism, the two alleles of a given gene occupy corresponding loci on a pair of homologous chromosomes.

Amino acid sequence. As used herein, includes an oligopeptide, peptide, polypeptide, or protein and fragments thereof that are isolated from, native to, or naturally occurring in a plant, or are synthetically made but comprise the nucleic acid sequence of the endogenous counterpart.

Artificially manipulated. as used herein, "artificially manipulated" means to move, arrange, operate or control by the hands or by mechanical means or recombinant means, such as by genetic engineering techniques, a plant or plant cell, so as to produce a plant or plant cell that has a different biological, biochemical, morphological, or physiological phenotype and/or genotype in comparison to unmanipulated, naturally-occurring counterpart.

Asexual propagation. Producing progeny by generating an entire plant from leaf cuttings, stem cuttings, root cuttings, tuber eyes, stolons, single plant cells protoplasts, callus and the like, that does not involve fusion of gametes.

Backbone. Nucleic acid sequence of a binary vector that excludes the DNA insert sequence intended for transfer.

Backcrossing. Backcrossing is a process in which a breeder repeatedly crosses hybrid progeny back to one of the parents, for example, a first generation hybrid $F_1$ with one of the parental genotypes of the $F_1$ hybrid.

Bacterial Ring Rot. Bacterial ring rot is a disease caused by the bacterium *Clavibacter michiganense* ssp. Bacterial ring rot derives its name from a characteristic breakdown of the vascular ring within the tuber. This ring often appears as a creamy-yellow to light-brown, cheesy rot. On the outer surface of the potato, severely diseased tubers may show slightly sunken, dry and cracked areas. Symptoms of bacterial ring rot in the vascular tissue of infected tubers can be less obvious than described above, appearing as only a broken, sporadically appearing dark line or as a continuous, yellowish discoloration.

Black spot bruise. Black spots found in bruised tuber tissue are a result of a pigment called melanin that is produced following the injury of cells and gives tissue a brown, gray or black appearance. Melanin is formed when phenol substrates and an appropriate enzyme come in contact with each other as a result of cellular damage. The damage does not require broken cells. However, mixing of the substrate and enzyme must occur, usually when the tissue is impacted. Black spots occur primarily in the perimedullary tissue just beneath the vascular ring, but may be large enough to include a portion of the cortical tissue.

Border-like sequences. A "border-like" sequence is isolated from the selected plant species that is to be modified, or from a plant that is sexually-compatible with the plant species to be modified, and functions like the border sequences of *Agrobacterium*. That is, a border-like sequence of the present invention promotes and facilitates the integration of a polynucleotide to which it is linked. A DNA insert of the present invention preferably contains border-like sequences. A border-like sequence of a DNA insert is between 5-100 bp in length, 10-80 bp in length, 15-75 bp in length, 15-60 bp in length, 15-50 bp in length, 15-40 bp in length, 15-30 bp in length, 16-30 bp in length, 20-30 bp in length, 21-30 bp in length, 22-30 bp in length, 23-30 bp in length, 24-30 bp in length, 25-30 bp in length, or 26-30 bp in length. A DNA insert left and right border sequence are isolated from and/or native to the genome of a plant that is to be modified. A DNA insert border-like sequence is not identical in nucleotide sequence to any known *Agrobacterium*-derived T-DNA border sequence. Thus, a DNA insert border-like sequence may possess 1, 2, 3, 4, 5, 6, 7, 8, 9, 10, 11, 12, 13, 14, 15, 16, 17, 18, 19, 20, or more nucleotides that are different from a T-DNA border sequence from an *Agrobacterium* species, such as *Agrobacterium tumefaciens* or *Agrobacterium rhizogenes*. That is, a DNA insert border, or a border-like sequence of the present invention has at least 95%, at least 90%, at least 80%, at least 75%, at least 70%, at least 60% or at least 50% sequence identity with a T-DNA border sequence from an *Agrobacterium* species, such as *Agrobacterium tumefaciens* or *Agrobacterium rhizogenes*, but not 100% sequence identity. As used herein, the descriptive terms "DNA insert border" and "DNA insert border-like" are exchangeable. A border-like sequence can be isolated from a plant genome and be modified or mutated to change the efficiency by which it is capable of integrating a nucleotide sequence into another nucleotide sequence. Other polynucleotide sequences may be added to or incorporated within a border-like sequence of the present invention. Thus, a DNA insert left border or a DNA insert right border may be modified so as to possess 5'- and 3'-multiple cloning sites, or additional restriction sites. A DNA insert border sequence may be modified to increase the likelihood that backbone DNA from the accompanying vector is not integrated into the plant genome.

Consisting essentially of. A composition "consisting essentially of" certain elements is limited to the inclusion of those elements, as well as to those elements that do not materially affect the basic and novel characteristics of the inventive composition. Thus, so long as the composition does not affect the basic and novel characteristics of the instant invention, that is, does not contain foreign DNA that is not from the selected plant species or a plant that is sexually compatible with the selected plant species, then that composition may be considered a component of an inventive composition that is characterized by "consisting essentially of" language.

Cotyledon. A cotyledon is a type of seed leaf. The cotyledon contains the food storage tissues of the seed.

Degenerate primer. A "degenerate primer" is an oligonucleotide that contains sufficient nucleotide variations that it can accommodate base mismatches when hybridized to sequences of similar, but not exact, homology.

Dicotyledon (dicot). A flowering plant whose embryos have two seed leaves or cotyledons. Examples of dicots include, but are not limited to, tobacco, tomato, potato, sweet potato, cassava, legumes including alfalfa and soybean, carrot, strawberry, lettuce, oak, maple, walnut, rose, mint, squash, daisy, and cactus.

DNA insert. According to the present invention, the DNA insert to be inserted into the genome of a plant comprises polynucleotide sequences native to that plant or has native genetic elements to that plant. In one example, for instance, the DNA insert from pSIM1278 of the potato variety V11 of the present invention is a 10,148 bp non-coding polynucleotide that is native to potato or wild potato, a potato sexually-compatible plant, that is stably integrated into the genome of the plant cells upon transformation and silences genes involved in the expression of black spot bruises, asparagine accumulation and senescence sweetening. The DNA insert preferably comprises two expression cassettes and is inserted into a transformation vector referred to as the pSIM1278 transformation vector. The first cassette comprises fragments of both the asparagine synthetase-1 gene (Asn1) and the polyphenol oxidase-5 gene (Ppo5), arranged as inverted repeats between the Agp promoter of the ADP glucose pyrophosphorylase gene (Agp) and the Gbss promoter of the granule-bound synthase gene (Gbss). These promoters are predominantly active in tubers. The function of the second cassette is to silence the promoters of the starch associated gene dikinase-R1 (R1) and the phosphorylase-L gene (PhL). This cassette is comprised of fragments of the promoters of the starch associated gene dikinase-R1 (R1) and the phosphorylase-L gene (PhL), operably linked to the same Agp and Gbss promoters as the first cassette. These expression cassettes contain no foreign DNA, and consist of DNA only from either the selected plant species or from a plant that is sexually compatible with the selected plant species.

Embryo. The embryo is the immature plant contained within a mature seed.

Foreign. "Foreign," with respect to a nucleic acid, means that that nucleic acid is derived from non-plant organisms, or derived from a plant that is not the same species as the plant to be transformed, or is derived from a plant that is not interfertile with the plant to be transformed, or does not belong to the species of the target plant. According to the present invention, foreign DNA or RNA represents nucleic acids that are naturally occurring in the genetic makeup of fungi, bacteria, viruses, mammals, fish or birds, but are not naturally occurring in the plant that is to be transformed. Thus, a foreign nucleic acid is one that encodes, for instance, a polypeptide that is not naturally produced by the transformed plant. A foreign nucleic acid does not have to encode a protein product. According to the present invention, a desired intragenic plant is one that does not contain any foreign nucleic acids integrated into its genome.

Gene. As used herein, "gene" refers to the coding region and does not include nucleotide sequences that are 5'- or 3'- to that region. A functional gene is the coding region operably linked to a promoter or terminator. A gene can be introduced into a genome of a species, whether from a different species or from the same species, using transformation or various breeding methods.

Gene Converted (Conversion). Gene converted (conversion) plant refers to plants which are developed by a plant breeding technique called backcrossing wherein essentially all of the desired morphological and physiological characteristics of a variety are recovered in addition to the one or more genes transferred into the variety via the backcrossing technique, via genetic engineering or via mutation. One or more loci may also be transferred.

Genetic rearrangement. Refers to the re-association of genetic elements that can occur spontaneously in vivo as well as in vitro which introduce a new organization of genetic material. For instance, the splicing together of polynucleotides at different chromosomal loci, can occur spontaneously in vivo during both plant development and sexual recombination. Accordingly, recombination of genetic elements by non-natural genetic modification techniques in vitro is akin to recombination events that also can occur through sexual recombination in vivo.

Golden nematode. *Globodera rostochiensis*, commonly known as golden nematode, is a plant parasitic nematode affecting the roots and tubers of potato plants. Symptoms include poor plant growth, wilting, water stress and nutrient deficiencies.

Hypocotyl. A hypocotyl is the portion of an embryo or seedling between the cotyledons and the root. Therefore, it can be considered a transition zone between shoot and root.

In frame. Nucleotide triplets (codons) are translated into a nascent amino acid sequence of the desired recombinant protein in a plant cell. Specifically, the present invention contemplates a first nucleic acid linked in reading frame to a second nucleic acid, wherein the first nucleotide sequence is a gene and the second nucleotide is a promoter or similar regulatory element.

Integrate. Refers to the insertion of a nucleic acid sequence from a selected plant species, or from a plant that is from the same species as the selected plant, or from a plant that is sexually compatible with the selected plant species, into the genome of a cell of a selected plant species. "Integration" refers to the incorporation of only native genetic elements into a plant cell genome. In order to integrate a native genetic element, such as by homologous recombination, the present invention may "use" non-native DNA as a step in such a process. Thus, the present invention distinguishes between the "use of" a particular DNA molecule and the "integration" of a particular DNA molecule into a plant cell genome.

Introduction. As used herein, refers to the insertion of a nucleic acid sequence into a cell, by methods including infection, transfection, transformation or transduction.

Isolated. "Isolated" refers to any nucleic acid or compound that is physically separated from its normal, native environment. The isolated material may be maintained in a suitable solution containing, for instance, a solvent, a buffer, an ion, or other component, and may be in purified, or unpurified, form.

Late blight. A potato disease caused by the oomycete *Phytophthora infestans* and also known as 'potato blight' that can infect and destroy the leaves, stems, fruits, and tubers of potato plants.

Leader. Transcribed but not translated sequence preceding (or 5' to) a gene.

Locus. A locus confers one or more traits such as, for example, male sterility, herbicide tolerance, insect resistance, disease resistance, waxy starch, modified fatty acid metabolism, modified phytic acid metabolism, modified carbohydrate metabolism, and modified protein metabolism. The trait may be, for example, conferred by a naturally occurring gene introduced into the genome of the variety by backcrossing, a natural or induced mutation, or a transgene introduced through genetic transformation techniques. A locus may comprise one or more alleles integrated at a single chromosomal location.

Marketable Yield. Marketable yield is the weight of all tubers harvested that are between 2 and 4 inches in diameter. Marketable yield is measured in cwt (hundred weight) where cwt=100 pounds.

Monocotyledon (monocot). A flowering plant whose embryos have one cotyledon or seed leaf. Examples of monocots include, but are not limited to turf grass, maize, rice, oat, wheat, barley, sorghum, orchid, iris, lily, onion, and palm.

Native. A "native" genetic element refers to a nucleic acid that naturally exists in, originates from, or belongs to the genome of a plant that is to be transformed. Thus, any nucleic acid, gene, polynucleotide, DNA, RNA, mRNA, or cDNA molecule that is isolated either from the genome of a plant or plant species that is to be transformed or is isolated from a plant or species that is sexually compatible or interfertile with the plant species that is to be transformed, is "native" to, i.e., indigenous to, the plant species. In other words, a native genetic element represents all genetic material that is accessible to plant breeders for the improvement of plants through classical plant breeding. Any variants of a native nucleic acid also are considered "native" in accordance with the present invention. In this respect, a "native" nucleic acid may also be isolated from a plant or sexually compatible species thereof and modified or mutated so that the resultant variant is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% similar in nucleotide sequence to the unmodified, native nucleic acid isolated from a plant. A native nucleic acid variant may also be less than about 60%, less than about 55%, or less than about 50% similar in nucleotide sequence. A "native" nucleic acid isolated from a plant may also encode a variant of the naturally occurring protein product transcribed and translated from that nucleic acid. Thus, a native nucleic acid may encode a protein that is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% similar in amino acid sequence to the unmodified, native protein expressed in the plant from which the nucleic acid was isolated.

Native genetic elements. "Native genetic elements" can be incorporated and integrated into a selected plant species genome according to the present invention. Native genetic elements are isolated from plants that belong to the selected plant species or from plants that are sexually compatible with the selected plant species. For instance, native DNA incorporated into cultivated potato (*Solanum tuberosum*) can be derived from any genotype of *S. tuberosum* or any genotype of a wild potato species that is sexually compatible with *S. tuberosum* (e.g., *S. demissum*).

Naturally occurring nucleic acid. Naturally occurring nucleic acid are found within the genome of a selected plant species and may be a DNA molecule or an RNA molecule. The sequence of a restriction site that is normally present in the genome of a plant species can be engineered into an exogenous DNA molecule, such as a vector or oligonucleotide, even though that restriction site was not physically isolated from that genome. Thus, the present invention permits the synthetic creation of a nucleotide sequence, such as a restriction enzyme recognition sequence, so long as that sequence is naturally occurring in the genome of the selected plant species or in a plant that is sexually compatible with the selected plant species that is to be transformed.

Operably linked. Combining two or more molecules in such a fashion that in combination they function properly in a plant cell. For instance, a promoter is operably linked to a structural gene when the promoter controls transcription of the structural gene.

Plant. As used herein, the term "plant" includes but is not limited to angiosperms and gymnosperms such as potato, tomato, tobacco, alfalfa, lettuce, carrot, strawberry, sugarbeet, cassava, sweet potato, soybean, maize, turf grass, wheat, rice, barley, sorghum, oat, oak, *eucalyptus*, walnut, and palm. Thus, a plant may be a monocot or a dicot. The word "plant," as used herein, also encompasses plant cells, seed, plant progeny, propagule whether generated sexually or asexually, and descendents of any of these, such as cuttings or seed. Plant cells include suspension cultures, callus, embryos, meristematic regions, callus tissue, leaves, roots, shoots, gametophytes, sporophytes, pollen, seeds and microspores. Plants may be at various stages of maturity and may be grown in liquid or solid culture, or in soil or suitable media in pots, greenhouses or fields. Expression of an introduced leader, trailer or gene sequences in plants may be transient or permanent. A "selected plant species" may be, but is not limited to, a species of any one of these "plants."

Plant Parts. As used herein, the term "plant parts" (or a potato plant, or a part thereof) includes but is not limited to protoplast, leaf, stem, root, root tip, anther, pistil, seed, embryo, pollen, ovule, cotyledon, hypocotyl, flower, tuber, eye, tissue, petiole, cell, meristematic cell, and the like.

Plant species. The group of plants belonging to various officially named plant species that display at least some sexual compatibility.

Plant transformation and cell culture. Broadly refers to the process by which plant cells are genetically modified and transferred to an appropriate plant culture medium for maintenance, further growth, and/or further development.

Precise breeding. Refers to the improvement of plants by stable introduction of nucleic acids, such as native genes and regulatory elements isolated from the selected plant species, or from another plant in the same species as the selected plant, or from species that are sexually compatible with the selected plant species, into individual plant cells, and subsequent regeneration of these genetically modified plant cells into whole plants. Since no unknown or foreign nucleic acid is permanently incorporated into the plant genome, the inventive technology makes use of the same genetic material that is also accessible through conventional plant breeding.

Progeny. As used herein, includes an $F_1$ potato plant produced from the cross of two potato plants where at least one plant includes potato cultivar V11 and progeny further includes, but is not limited to, subsequent $F_2$, $F_3$, $F_4$, $F_5$, $F_6$, $F_7$, $F_8$, $F_9$, and V11 generational crosses with the recurrent parental line.

Quantitative Trait Loci (QTL). Quantitative trait loci (QTL) refer to genetic loci that control to some degree numerically representable traits that are usually continuously distributed.

Recombinant. As used herein, broadly describes various technologies whereby genes can be cloned, DNA can be sequenced, and protein products can be produced. As used herein, the term also describes proteins that have been produced following the transfer of genes into the cells of plant host systems.

Regeneration. Regeneration refers to the development of a plant from tissue culture.

Regulatory sequences. Refers to those sequences which are standard and known to those in the art that may be included in the expression vectors to increase and/or maximize transcription of a gene of interest or translation of the resulting RNA in a plant system. These include, but are not limited to, promoters, peptide export signal sequences, introns, polyadenylation, and transcription termination sites. Methods of modifying nucleic acid constructs to increase expression levels in plants are also generally known in the art (see, e.g. Rogers et al., 260 *J. Biol. Chem.* 3731-38, 1985; Cornejo et al., 23 *Plant Mol. Biol.* 567: 81,1993). In engineering a plant system to affect the rate of transcription of a protein, various factors known in the art, including regulatory sequences such as positively or negatively acting sequences, enhancers and silencers, as well as chromatin structure may have an impact. The present invention provides that at least one of these factors may be utilized in engineering plants to express a protein of interest. The regulatory sequences of the present invention are native genetic elements, i.e., are isolated from the selected plant species to be modified.

Selectable marker. A "selectable marker" is typically a gene that codes for a protein that confers some kind of resistance to an antibiotic, herbicide or toxic compound, and is used to identify transformation events. Examples of selectable markers include the streptomycin phosphotransferase (spt) gene encoding streptomycin resistance, the phosphomannose isomerase (pmi) gene that converts mannose-6-phosphate into fructose-6 phosphate; the neomycin phosphotransferase (nptII) gene encoding kanamycin and geneticin resistance, the hygromycin phosphotransferase (hpt or aphiv) gene encoding resistance to hygromycin, acetolactate synthase (als) genes encoding resistance to sulfonylurea-type herbicides, genes coding for resistance to herbicides which act to inhibit the action of glutamine synthase such as phosphinothricin or basta (e.g., the bar gene), or other similar genes known in the art.

Sense suppression. Reduction in expression of an endogenous gene by expression of one or more an additional copies of all or part of that gene in transgenic plants.

Specific gravity. As used herein, "specific gravity" is an expression of density and is a measurement of potato quality. There is a high correlation between the specific gravity of the tuber and the starch content and percentage of dry matter or total solids. A higher specific gravity contributes to higher recovery rate and better quality of the processed product.

T-DNA-Like. A "T-DNA-like" sequence is a nucleic acid that is isolated from a selected plant species, or from a plant that is sexually compatible with the selected plant species, and which shares at least 75%, 80%, 85%, 90%, or 95%, but not 100%, sequence identity with *Agrobacterium* species T-DNA. The T-DNA-like sequence may contain one or more border or border-like sequences that are each capable of integrating a nucleotide sequence into another polynucleotide.

Total Yield. Total yield refers to the total weight of all harvested tubers.

Trailer. Transcribed but not translated sequence following (or 3' to) a gene.

Transcribed DNA. DNA comprising both a gene and the untranslated leader and trailer sequence that are associated with that gene, which is transcribed as a single mRNA by the action of the preceding promoter.

Transformation of plant cells. A process by which DNA is stably integrated into the genome of a plant cell. "Stably" refers to the permanent, or non-transient retention and/or expression of a polynucleotide in and by a cell genome. Thus, a stably integrated polynucleotide is one that is a fixture within a transformed cell genome and can be replicated and propagated through successive progeny of the cell or resultant transformed plant. Transformation may occur under natural or artificial conditions using various methods well known in the art. Transformation may rely on any known method for the insertion of nucleic acid sequences into a prokaryotic or eukaryotic host cell, including *Agrobacterium*-mediated transformation protocols, viral infection, whiskers, electroporation, heat shock, lipofection, polyethylene glycol treatment, micro-injection, and particle bombardment.

Transgene. A gene that will be inserted into a host genome, comprising a protein coding region. In the context of the instant invention, the elements comprising the transgene are isolated from the host genome.

Transgenic plant. A genetically modified plant which contains at least one transgene.

Variant. A "variant," as used herein, is understood to mean a nucleotide or amino acid sequence that deviates from the standard, or given, nucleotide or amino acid sequence of a particular gene or protein. The terms, "isoform," "isotype," and "analog" also refer to "variant" forms of a nucleotide or an amino acid sequence. An amino acid sequence that is altered by the addition, removal or substitution of one or more amino acids, or a change in nucleotide sequence, may be considered a "variant" sequence. The variant may have "conservative" changes, wherein a substituted amino acid has similar structural or chemical properties, e.g., replacement of leucine with isoleucine. A variant may have "non-conservative" changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art such as Vector NTI Suite (InforMax, Md.) software.

Vine Maturity. Vine maturity refers to a plant's ability to continue to utilize carbohydrates and photosynthesize. Vine maturity is scored on a scale of 1 to 5 where 1=dead vines and 5=vines green, still flowering.

The insertion of desirable traits into the genome of potato plants presents particular difficulties because potato is tetraploid, highly heterozygous and sensitive to in-breeding depression. It is therefore very difficult to efficiently develop transgenic potato plants that produce less acrylamide and less harmful Maillard-reaction products, including N-Nitroso-N-(3-keto-1,2-butanediol)-3'-nitrotyramine (Wang et al., *Arch Toxicol* 70: 10-5, 1995), 5-hydroxymethyl-2-furfural (Janzowski et al., *Food Chem Toxicol* 38: 801-9, 2000), and other Maillard reaction products with mutagenic properties (Shibamoto, *Prog Clin Biol Res* 304: 359-76, 1989), during processing using conventional breeding.

Several methods have been tested and research is ongoing to reduce acrylamide through process changes, reduction in dextrose, and additives such as asparaginase, citrate, and competing amino acids. The required capital expense to implement process changes throughout the potato industry would cost millions of dollars. In addition to the expense, these process changes have significant drawbacks including potentially negative flavors associated with additives such as asparaginase or citrate. Typically, fry manufacturers add dextrose during processing of french fries to develop the desired golden brown color, but dextrose also increases the formation of acrylamide through the Maillard reaction. Significant reductions in acrylamide occur by merely omitting dextrose from the process; however, the signature golden brown colors must then be developed some other way (such as though the addition of colors like annatto) The use of alternate colors, results in an absence of the typical flavors that develop through those browning reactions. Another challenge with the use of additives to reduce reactants like asparagine is moisture migration that occurs during frozen storage with the resulting return of asparagine to the surface and increased acrylamide. Finally, the blackening that occurs after potatoes are bruised affects quality and recovery in processing French fries and chips. Damaged and bruised potatoes must be trimmed or are rejected before processing, resulting in quality challenges or economic loss.

The "native technology" strategy of the present invention addresses the need of the potato industry to improve the agronomic characteristics and nutritional value of potatoes by reducing the expression of polyphenol oxidase-5 (PPO-5), which is responsible for black spot bruise, the expression of asparagine synthetase-1 (Asn-1), which is responsible for the accumulation of asparagine, a precursor in acrylamide formation, reducing the expression of phosphorylase-L and kinase-R1, which are enzymes associated with the accumulation of reducing sugars that normally react with amino acids, such as asparagine, and form toxic Maillard products, including acrylamide. The partial or complete silencing of these genes in tubers decreases the potential to produce acrylamide. Use of the native technology of the invention allows for the incorporation of desirable traits into the genome of commercially valuable potato plant varieties by transforming the potatoes only with "native" genetic material, that is genetic material obtained from potato plants or plants that are sexually-compatible with potato plants, that contains only non-coding regulatory regions, without the integration of any foreign genetic material into the plant's genome. Desirable traits include high tolerance to impact-induced black spot bruise, increased resistance to late blight infection, reduced formation of the acrylamide precursor asparagine and reduced accumulation of reducing sugars, with consequent decrease in accumulation of toxic Maillard products, including acrylamide, improved quality and food color control. The incorporation of these desirable traits into existing potato varieties is impossible to achieve through traditional breeding because potato is tetraploid, highly heterozygous and sensitive to inbreeding depression.

The non-coding potato plant DNA insert sequences used in the present invention are native to the potato plant genome and do not contain any *Agrobacterium* DNA. One of the DNA inserts preferably comprises two expression cassettes and is inserted into a transformation vector referred to as the pSIM1278 transformation vector. The first cassette comprises fragments of both the asparagine synthetase-1 gene (Asn1) and the polyphenol oxidase-5 gene (Ppo5), arranged as inverted repeats between the Agp promoter of the ADP glucose pyrophosphorylase gene (Agp) and the Gbss promoter of the granule-bound synthase gene (Gbss). These promoters are predominantly active in tubers. The function of the second cassette is to silence the promoters of the starch associated gene dikinase-R1 (R1) and the phosphorylase-L gene (PhL). This cassette is comprised of fragments of the promoters of the starch associated gene dikinase-R1 (R1) and the phosphorylase-L gene (PhL), operably linked to the same Agp and Gbss promoters as the first cassette. These expression cassettes contain no foreign DNA, and consist of DNA only from either the selected plant species or from a plant that is sexually compatible with the selected plant species.

The commercially valuable potato plant variety used in the present invention is Snowden. The Snowden variety was developed by the University of Wisconsin and released in 1990 (PAA 2009) as a public variety. Plants are tall, semi-erect, and have lightly pigmented stems with slight pubescence. The leaves are open with an olive green color and slightly pubescent. There are few flowers that are medium sized and white with yellow anthers. Under most conditions no seed berries are produced. The tubers are round to oval with buff-colored skin and white flesh. Snowden is a high-yielding variety that produces a high tuber set. Snowden responds well to nitrogen and needs high irrigation. The Snowden variety has high specific gravity, good storability, and short dormancy. Snowden is an excellent chipping variety from the field as well as at storage. Snowden potatoes have been shown to store for up to nine months at 45° F. with low sugar levels (UNL Crop Watch, 2014).

Snowden is the second most popular public potato variety used for making potato chips. Snowden represents significant value to the potato industry because unlike the Atlantic variety, which must be processed right after harvesting, the Snowden variety can be stored for over six months (UNL Crop Watch, 2015). In 2013, Snowden comprised approximately 2% of seed potato acreage in the U.S. (National Potato Council, 2014).

The present invention provides a potato variety of significant market value—namely Snowden—transformed with the transformation vector pSIM1278, identified using the polymerase chain reaction rather than markers, and successfully propagated. Also provided are food products made from the tubers of the potato plant variety V11 of the present invention. Potato cultivar V11 has the following unique plant variety identifier with the Organization for Economic Cooperation and Development (OECD): SPS-ØØV11-6.

Targeted gene silencing with native DNA reduces the level of the RNA transcripts of the targeted genes in the tubers of the potato plant variety V11. Potato cultivar V11 contains expression cassettes that lower levels of reducing sugars in tubers by multiple mechanisms. Through the transformation with pSIM1278, silencing cassettes were introduced for the promoters of the starch associated gene (R1) and the phosphorylase-L gene (PhL). Together, these traits function by slowing the conversion of starch and sucrose to reducing sugars (glucose and fructose).

Thus, the tubers of the potato plant variety V11 of the invention incorporate highly desirable traits, including a reduced ratio in free amide amino acids asparagine and glutamine, which is associated with reduced acrylamide formation upon frying or baking. Specifically, the potato variety V11 of the present invention is characterized by reduction in free-asparagine content and reduced discoloration associated with black spot bruise. Furthermore, the potato variety V11 of the invention displays a delay in the degradation of starch into the reducing sugars glucose and fructose during storage. Impairment of starch-to-sugar conversion further reduces senescence sweetening and acrylamide formation and limits heat-induced browning.

Potato variety V11 of the present invention is therefore extremely valuable in the potato industry and food market, as its tubers produce significantly less acrylamide upon heat processing and do not carry any potentially harmful foreign genes.

Asparagine Synthetase 1 (Asn1)

The expressed protein product of Asn1, ASN1, catalyzes the conversion of glutamine to asparagine by transferring the side-chain amine ($NH_2$) from glutamine to aspartate to form asparagine (FIG. 1). Asparagine and glutamine are thought to play an important role in the transport and storage of nitrogen (Lehmann and Ratajczak, 2008). While most nitrogen is transported to the potato tuber as glutamine, the majority of glutamine is converted to asparagine by ASN1 (Chawla et al., 2012). Asparagine is the predominant free amino acid in potato tubers and constitutes up to 25% of the total free amino acid pool in tubers (Golan-Goldhirsh, 1986; Koch et al., 2003).

It has been shown that down-regulating Asn1 in tubers decreases the levels of free asparagine while increasing free glutamine levels, without affecting plant growth or tuber phenotype. Furthermore, glutamine does not represent a significant precursor for acrylamide (Stadler, 2005).

Asparagine is a substrate of the Maillard reaction that converts amino acids and reducing sugars to acrylamide during high-temperature processing. This reaction occurs between sugars and amino acids, affecting changes in the color, flavor, functional properties and nutritional value of food (O'brien and Morrissey 1989). Reduction of ASN1 and asparagine levels in potato tubers by down-regulating Asn1 has been shown to reduce acrylamide levels by as much as 70% in tubers (Collinge and Clark, 2013).

Water Dikinase R1 (R1)

Starch is one of the most abundant polymers in nature and is abundant in potato tubers as a storage carbohydrate. In cold storage, the starch in tubers is converted to reducing sugars during a process known as cold storage sweeting. The degradation of starch into reducing sugars has been shown to be due in part by the phosphorylation of the starch molecules in the tuber by R1 (Ritte et al., 2002, 2006).

R1 catalyzes the transfer of phosphates of ATP to α-glucan and water, resulting in phosphorylated starch (Lorberth et al., 1998). Phosphorylation affects the degree of crystalline packing within the starch granule and makes it more accessible to degradation. Thus, loss of R1 activity impairs starch degradation, which reduces accumulation of the reducing sugars glucose and fructose (Ritte et al., 2002, 2006). Down-regulation of this gene can lead to lower concentrations of reducing sugars and help contribute to low acrylamide potential via the Maillard reaction.

α-Glucan Phosphorylase, Starch Phosphorylase L (PhL)

The phosphorylase PhL gene is also thought to be responsible for degradation of starch to sugar during cold storage (Sonnewald et al., 1995). Phosphorylase L degrades starch by phosphorolytic release of glucose-1-phosphate from glucan chains. Down-regulation of PhL in potato and mutation in *Arabidopsis* does not alter total starch levels, but a loss of the enzymatic activity limits reducing sugar accumulation. Down-regulation of this gene can lead to lower concentrations of reducing sugars and help contribute to low acrylamide potential via the Maillard reaction.

Polyphenol Oxidase 5 (Ppo5)

Polyphenol oxidase enzymes (PPO) are found in most organisms including animals, plants, fungi and bacteria. Polyphenol oxidases are copper metalloenzymes that oxidize mono- and o-diphenols to o-diquinones by utilizing molecular oxygen (Thipyapong et al., 2004). Typically, PPO activity is latent until the enzyme is released by disruption of the cell structure through forces like wounding and senescence. When cell membranes are damaged, PPO enzyme is released and reacts along with oxygen molecules to produce quinones (Thipyapong et al., 2004). PPO and its role in the production of black and brown quinones are of interest in the post-harvest physiology of many fruit and vegetable crops.

The blackening that occurs after potatoes are peeled or bruised is a phenomenon caused by leakage of polyphenol oxidase from damaged plastids into the potato cell's cytoplasm (Thygesen, 1995). In addition, impacts sustained during harvest and post-harvest activities induce the release of PPO from cell plastids resulting in negative effects on quality and recovery in processing fries and chips, as well as the marketability of fresh potatoes. A family of six genes encoding PPO exists in potato, with one gene (Ppo5) being tuber-specific and the remaining five genes responsible for PPO expression in other tissues. By down-regulating Ppo5, reduced black spots in cut potatoes have been shown (Collinge and Clark, 2013).

EXAMPLES

The present invention uses native technology to integrate native non-coding DNA into the genome of selected potato plant varieties to develop new intragenic potato plant varieties. The method includes trait identification, design of vectors, incorporation of vectors into *Agrobacterium*, selection of the recipient potato variety, plant transformation, evidence of absence of open reading frames, and confirmation that the new potato plant varieties contain only the native DNA. The potato cultivar V11 of the present invention has a lowered potential to form acrylamide, lower amounts of sucrose and is more resistant to black spot bruise than its untransformed counterpart.

Example 1. The pSIM1278 Transformation Vector

Figure 2:
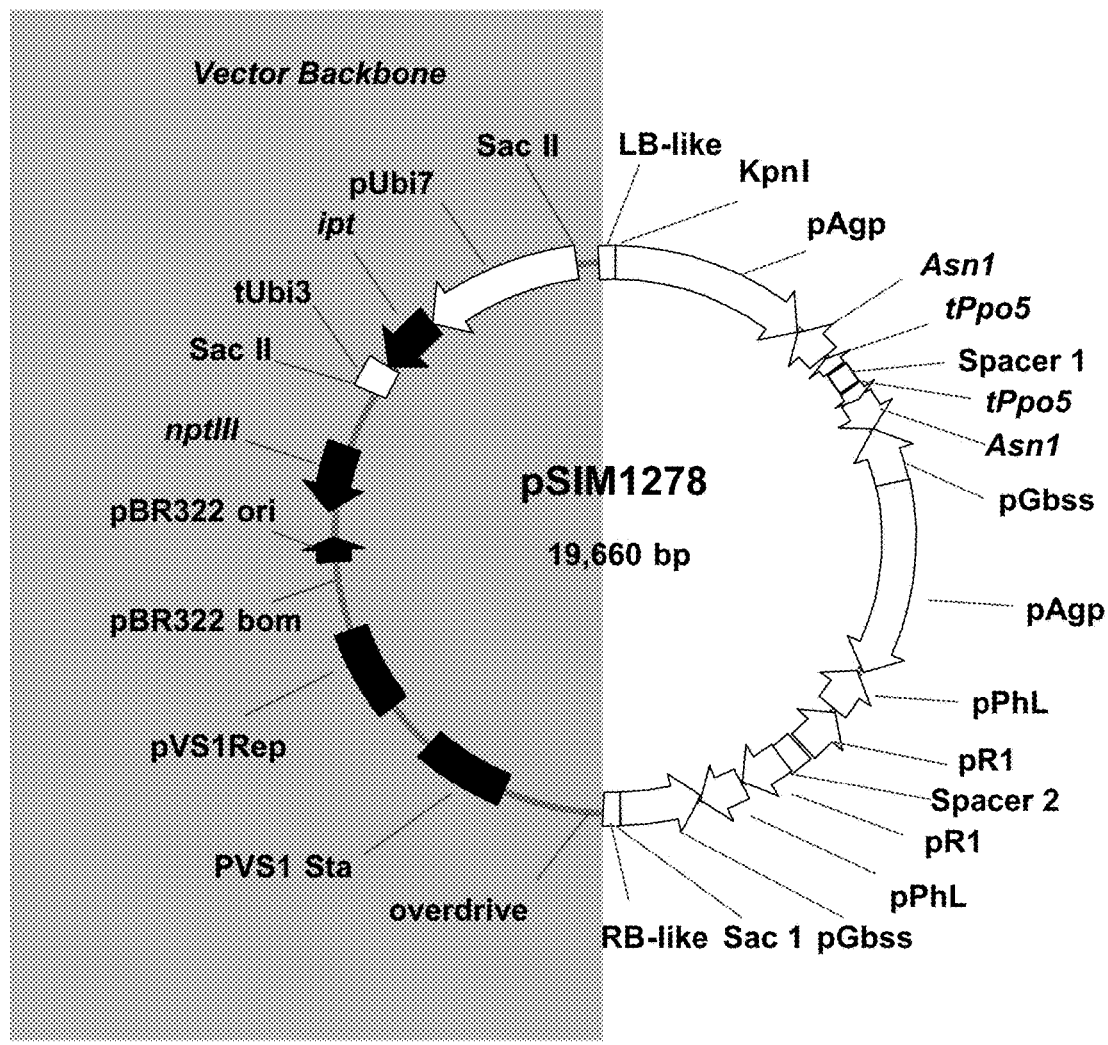
FIG. 2 depicts the pSIM1278 transformation vector. The vector backbone region, on the left, is 9,512 bp long, as it starts at position 10,149 bp and ends at position 19,660 bp. The backbone DNA consists mainly of bacterial DNA which provides support maintenance of the DNA insert prior to plant transformation. The DNA insert region (right side), including flanking Border sequences, is 10,148 bp long (from 1 bp to 10,148 bp). The DNA insert consists of native DNA only and is stably integrated into the potato genome upon transformation.

The transformation vector pSIM1278 used in the invention was derived from pSIM106, which was created by ligating a 0.4-kb potato plant DNA fragment (deposited as GenBank accession no. AY566555) with a 5.9-kb SacII-SphI fragment of pCAMBIA1301 (CAMBIA, Canberra, Australia), carrying bacterial origins of replication from plasmids pVS1 and pBR322, and the npaII gene for bacterial resistance to kanamycin. An expression cassette comprising the *Agrobacterium* ipt gene preceded by the Ubi-3 promoter (Garbarino and Belknap, 1994) and followed by the Ubi-3 terminator was introduced as a 2.6-kb SacII fragment into the vector backbone (Rommens et al., 2004). Insertion of the native 10-kb DNA segment carrying two silencing cassettes into the DNA insert of pSIM106 yielded pSIM1278. This vector was used for all transformations. The pSIM1278 vector map is shown in FIG. 2. The vector backbone region is 9,512 bp, as it starts at position 10,149 bp and ends at position 19,660 bp. The backbone DNA consists mainly of bacterial DNA and provides support maintenance of the DNA insert prior to plant transformation. The backbone portion is not transferred into the plant cells. The various elements of the backbone are described in Table 1. The general structure map of pCAMBIA vectors can be found at the Cambia website.

TABLE 1

| pSIM1278 backbone elements | | | | |
|---|---|---|---|---|
| Genetic Element | Origin | Accession Number | Position (pSIM1278) | Function |
| SacII restriction site | S. tuberosum | AJ272136.1 | 19,411-19,416 | Restriction site used to connect Ubi7 promoter with LB flanking sequence. |

TABLE 1-continued pSIM1278 backbone elements

| Genetic Element | Origin | Accession Number | Position (pSIM1278) | Function |
|---|---|---|---|---|
| Polyubiquitin promoter (Ubi7) including the coding sequence for a 76-amino-acid potato ubiquitin monomer (UBQmon) | S. tuberosum var. Ranger Russet | U26831.1 | 17,671-19,410 | Promoter to drive expression of the ipt backbone marker gene |
| Isopentenyl transferase (ipt) gene | Agrobacterium tumefaciens | NC_002377.1 | 16,936-17,658 | Condensation of AMP and isopentenylpyrophosphate to form isopentenyl-AMP, a cytokinin in the plant. Results in abnormal growth phenotypes in plant (Smigocki and Owens 1988) |
| Terminator of the ubiquitin-3 gene (tUbi3) | S. tuberosum | GP755544.1 | 16,230-16,584 | Terminator for ipt gene transcription (Garbarino and Belknap 1994) |
| Neomycin phosphotransferase III (nptIII) gene | E. coli | FJ362602.1 | 15,240-16,034 | Aminoglycoside phosphotransferase (Courvalin et al. 1977) |
| Origin of replication for pBR322 (pBR322 ori) | E. coli | J01784.1 | 14,669-14,949 | Bacterial origin of replication |
| (pBR322 bom) | E. coli | J01749.1 | 14,269-14,529 | pBR322 region for replication in E. coli |
| pVS1 replicon (pVS1Rep) | Pseudomonas fluorescens plasmid pVS1 | AJ537514.1 (4,501-5,501) | 12,859-13,859 | pVS1 region for replication in Agrobacterium |
| pVS1 partitioning protein StaA (PVS1 Sta) | Pseudomonas fluorescens plasmid pVS1 | AJ537514.1 (6,095-7,095) | 11,266-12,266 | pVS1 stability |
| Overdrive | Agrobacterium tumefaciens | K00549.1 (103-132) | 10,155-10,184 | Enhances cleavage at the Right Border site |

Example 2. The pSIM1278 Plant DNA Insert and its Open Reading Frames (ORFs)

Figure 3:
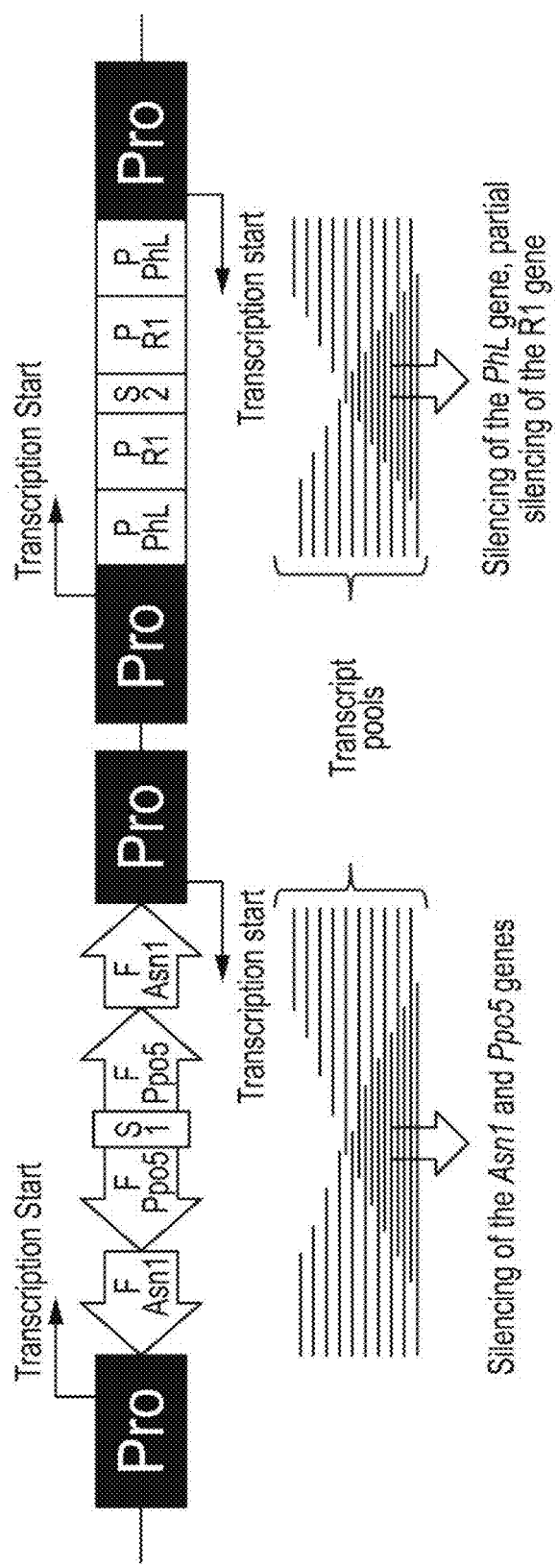
FIG. 3 provides a schematic representation of the silencing cassettes in the DNA insert inserted in the pSIM1278 transformation vector. Each silencing cassette contains two copies of two gene fragments separated by a spacer. Two copies of a DNA segment comprising fragments of four targeted genes, namely Asn-1, Ppo-5, PhL and R1, were inserted as inverted repeats between two convergent promoters, indicated as Pro, that are predominantly active in tubers. Plants containing the resulting silencing cassette produce a diverse and unpolyadenylated array of RNA molecules in tubers that dynamically and vigorously silence the intended target genes. The size of the RNA molecules was generally smaller than the distance between the two promoters employed because convergent transcription results in collisional transcription.

The pSIM1278 DNA insert region, including the flanking border sequences, used in the pSIM1278 is 10,148 bp long, from 1 bp to 10,148 bp. The pSIM1278 DNA insert consists of native DNA only and is stably integrated into the potato genome. The pSIM1278 DNA insert or a functional part thereof, is the only genetic material of vector pSIM1278 that is integrated in the potato plant varieties of the invention. The pSIM1278 DNA insert is described in FIG. 3 and Table 2 below. The LB and RB sequences (25 bp each) were synthetically designed to be similar to and function like T-DNA borders from Agrobacterium tumefaciens. The GenBank Accession AY566555 was revised to clarify the sources of DNA for the Border regions. ASN1 described as genetic elements 5 and 10 is referred to as StAst1 in Chawla et al., 2012.

TABLE 2 pSIM1278 DNA insert elements

| Genetic Element | Origin | Accession Number | Position (pSIM1278) | Intended Function |
|---|---|---|---|---|
| 1. Left Border (LB) site[1] | Synthetic | AY566555 (bases 1-25) | 1-25 | Site for secondary cleavage to release single-stranded DNA insert from pSIM1278 (van Haaren et al. 1989) |
| 2. Left Border region sequence including LB | S. tuberosum var. Ranger Russet. | AY566555 (bases1-187) | 1-187 | Supports secondary cleavage at LB |
| 3. KpnI restriction site | S. tuberosum | AF393847.1 | 188-193 | Site for connection of DNA insert with LB flanking sequence. |
| 4. Promoter for the ADP glucose pyrophosphorylase gene (pAgp), 1st copy | S. tuberosum var. Ranger Russet | HM363752 | 194-2,453 | One of the two convergent promoters that drives expression of an inverted repeat containing fragments of Asn1 and Ppo5, especially in tubers |
| 5. Fragment of the asparagine synthetase-1 (Asn1) gene (1st copy antisense orientation) | S. tuberosum var. Ranger Russet | HM363759 | 2,454-2,858 | Generates with (10) double stranded RNA that triggers the degradation of Asn1 transcripts to impair asparagine formation (Chawla et al. 2012) [2] |
| 6. 3'-untranslated sequence of the polyphenol oxidase-5 gene (Ppo5) (1st copy, in antisense orientation) | S. verrucosum | HM363754 | 2,859-3,002 | Generates with (9) double stranded RNA that triggers the degradation of Ppo5 transcripts to block black spot development |

TABLE 2-continued pSIM1278 DNA insert elements

| Genetic Element | Origin | Accession Number | Position (pSIM1278) | Intended Function |
|---|---|---|---|---|
| 7. XbaI restriction site | S. tuberosum | DQ478950.1 | 3,003-3,008 | Site for connection of the first Ppo5 copy to spacer-1. |
| 8. Spacer-1 | S. tuberosum var. Ranger Russet | HM363753 | 3,009-3,166 | Sequence between the 1st inverted repeats |
| 9. 3'-untranslated sequence of the polyphenol oxidase-5 gene (Ppo5) (2nd copy, in sense orientation) | S. verrucosum | HM363754 | 3,167-3,310 | Generates with (6) double stranded RNA that triggers the degradation of Ppo5 transcripts to block black spot development |
| 10. Fragment of the asparagine synthetase-1 (Asn1) gene (2nd copy, in sense orientation) | S. tuberosum var. Ranger Russet | HM363759 | 3,311-3,715 | Generates with (5) double stranded RNA that triggers the degradation of Asn1 transcripts to impair asparagine formation (Chawla et al. 2012) [2] |
| 11. EcoRI restriction site | S. tuberosum var. Ranger Russet | X73477 | 3,716-3,721 | Site for connection of the second Asn1 copy to Gbss promoter. |
| 12. Promoter for the granule-bound starch synthase (pGbss) gene (1st copy, convergent orientation relative to the 1st copy of pAgp) | S. tuberosum var. Ranger Russet | HM363755 | 3,722-4,407 | One of the two convergent promoters that drives expression of an inverted repeat containing fragments of Asn1 and Ppo5, especially in tubers |
| 13. SpeI/KpnI restriction sites | S. tuberosum var. Ranger Russet | X95996/ AF393847.1 | 4,408-4,423 | Polylinker site for connection of Gbss promoter to the second Agp promoter. |
| 14. pAgp, 2nd copy | S. tuberosum var. Ranger Russet | HM363752 | 4,424-6,683 | One of the two convergent promoters that drives expression of an inverted repeat containing fragments of the promoters of PhL and R1, especially in tubers |
| 15. Fragment of promoter for the potato phosphorylase-L (pPhL) gene (1st copy, in antisense orientation) | S. tuberosum var. Ranger Russet | HM363758 | 6,684-7,192 | Generates with (20) double stranded RNA that triggers the degradation of PhL transcripts to limit the formation of reducing sugars through starch degradation |
| 16. Fragment of promoter for the potato R1 gene (pR1) (1st copy, in antisense orientation) | S. tuberosum var. Ranger Russet | HM363757 | 7,193-7,724 | Generates with (19) double stranded RNA that triggers the degradation of R1 transcripts to limit the formation of reducing sugars through starch degradation |
| 17. PstI restriction site | S. tuberosum var. Ranger Russet | DQ478950.1 | 7,725-7,730 | Site for connection of the first R1 promoter fragment to the spacer-2 |
| 18. Spacer-2 | S. tuberosum var. Ranger Russet | HM363756 | 7,731-7,988 | Sequence between the 2nd inverted repeat |
| 19. Fragment of promoter for the potato R1 gene (pR1) (2nd copy, in sense orientation) | S. tuberosum var. Ranger Russet | HM363757 | 7,989-8,520 | Generates with (16) double stranded RNA that triggers the degradation of R1 transcripts to limit the formation of reducing sugars through starch degradation |
| 20. Fragment of promoter for the potato phosphorylase-L (pPhL) gene (2nd copy, in sense orientation) | S. tuberosum var. Ranger Russet | HM363758 | 8,521-9,029 | Generates with (15) double stranded RNA that triggers the degradation of PhL transcript to limit the formation of reducing sugars through starch degradation |
| 21. pGbss (2nd copy, convergent orientation relative to the 2nd copy of pAgp) | S. tuberosum var. Ranger Russet | HM363755 | 9,030-9,953 | One of the two convergent promoters that drives expression of an inverted repeat containing fragments of the promoters of PhL and R1, especially in tubers |
| 22. SacI restriction site | S. tuberosum | AF143202 | 9,954-9,962 | Site for connection of DNA insert with RB flanking sequence. |
| 23. Right Border region sequence including RB | S. tuberosum var. Ranger Russet | AY566555 (bases 231-416) | 9,963-10,148 | Supports primary cleavage at RB-Like site |

TABLE 2-continued pSIM1278 DNA insert elements

| Genetic Element | Origin | Accession Number | Position (pSIM1278) | Intended Function |
|---|---|---|---|---|
| 24. Right Border (RB) sequence[1] | Synthetic | AY566555 (bases 392-416) | 10,124-10,148 | Site for primary cleavage to release single stranded DNA insert from pSIM1278 (van Haaren et al. 1989) |

[1]The LB and RB sequences (25-bp each) were synthetically designed to be similar to and function like T-DNA borders from *Agrobacterium tumefaciens*.
[2] ASN1 described as genetic elements 5 and 10 is referred to as StAst1 in Chawla et al., 2012.

The DNA insert described in Table 2 that was used to create potato line V11 of the present invention does not activate adjacent genes and does not adversely affect the phenotype of potato plant variety V11. In addition, the potato plant variety V11 of the invention does not produce novel proteins associated with open reading frames encoded by the DNA insert.

Example 3. Development of V11: Description of Marker-Free Transformation

Potato (*Solanum tuberosum* subsp. *tuberosum*) event V11 was developed by *Agrobacterium*-mediated transformation. The genes and regulatory elements used to confer these traits are all derived from the genomes of potatoes or sexually compatible species.

Briefly, transformation was carried out using a modified procedure based on Richael et al., 2008. Potato internode segments of four to six mm were cut from four-week old plants and infected with *Agrobacterium* AGL1 strain carrying pSIM1278. The C58-derived *Agrobacterium* strain AGL1 was developed by precisely deleting the transfer DNA of the hyper-virulent plasmid, pTiBo542 (Lazo et al. 1991). Transformed plants were grown on media containing the antibiotic, timentin, which prevents survival of *Agrobacterium*, and thus selects for plants free of *Agrobacterium*.

Stock plants were maintained in magenta boxes with 40 ml half-strength M516 (Phytotechnology) medium containing 3% sucrose and 2 g/l gelzan (propagation medium). Potato internode segments of four to six mm were cut from four-week old plants, infected with the *Agrobacterium* AGL1 strain carrying pSIM1278, and transferred to tissue culture media containing 3% sucrose and 2 g/l gelzan (co-cultivation medium). Infected explants were transferred, after two days, to M404 (Phytotechnology) medium containing 3% sucrose, 2 g/l gelzan, 300 mg/l timentin and 1.2 ml plant protection medium (Phytotechnology) to eliminate *Agrobacterium* (hormone-free medium). Evidence that the plants were *Agrobacterium*-free was obtained by incubating stem and/or leaf fragments of transformed events on nutrient broth-yeast extract (NBY medium) for 2 weeks at 28° C. (repeated twice) with no outgrowth. Transformed plants were transported and planted in the field only when free of live *Agrobacterium*. Details of the methods are described elsewhere (Richael et al. 2008).

Figure 4:
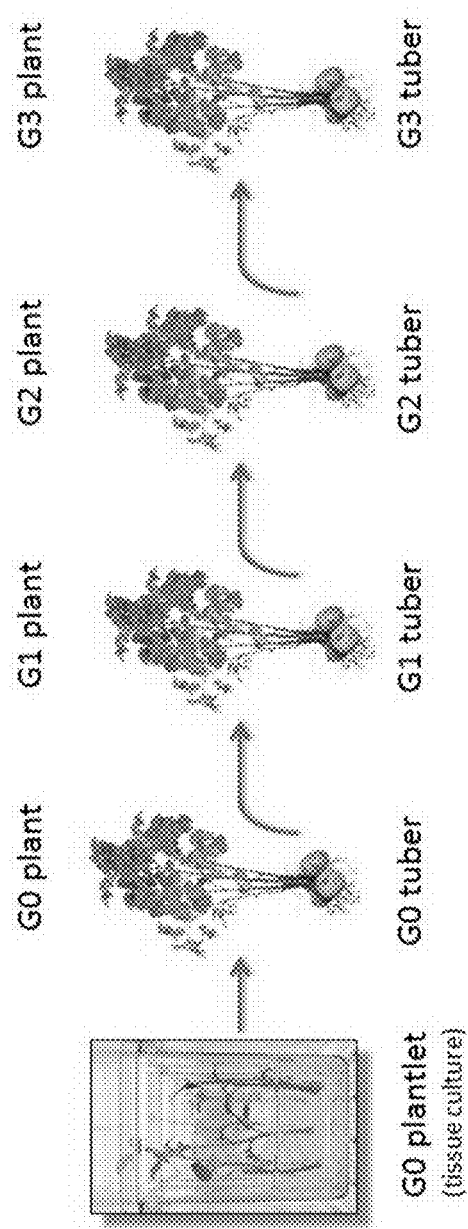
FIG. 4 depicts potato production generations following *Agrobacterium*-mediated transformation.

Following selection, plants are both antibiotic and *Agrobacterium* free, with the potato-derived expression cassettes inserted into the plant's genome. Leaf samples from mature G0 plantlets (FIG. 4) testing positive for the pSIM1278 T-DNA insert were propagated and assayed for the absence of *Agrobacterium*. *Agrobacterium*-free G0 plants were then transferred to greenhouse facilities.

Although *Agrobacterium* is effective in cleaving at the Right Border (RB) site, it often fails to fully release the DNA insert from its plasmid vector by also cutting at the Left Border (LB) site (Gelvin 2003). Consequently, some infected plant cells received the DNA insert itself as well as additional plasmid backbone sequences containing the backbone marker gene, isopentenyltyransferase (ipt), for a plant hormone cytokinin, which commonly regulates growth and development processes in plants. Overexpression results in stunted phenotypes, abnormal leaves, or the inability to root due to the cytokinin overproduction, which were used to select against plants containing backbone DNA (Richael et al. 2008). Every two weeks, the infected explants were transferred to fresh medium lacking any synthetic hormones and incubated in a Percival growth chamber under a 16-hr photoperiod at 24° C. where they started to form shoots. Many shoots expressed the ipt gene and displayed the cytokinin-overproduction phenotype; these shoots were discarded and not considered for further analyses. PCR genotyping demonstrated that about 0.3 to 1.5% of the remaining shoots contained at least part of the DNA insert while lacking the ipt gene.

Events were analyzed using Southern blots to identify plants containing a single insert of the T-DNA. Based on these results and field trials, V11 was selected and further assessed for insert integrity, copy number, gene silencing and agronomic performance. Subsequent V11 generations were developed through clonal propagation.

*Solanum tuberosum* varieties are prone to somaclonal variation and even in tissue culture frequently exhibit a degree of heterogeneity (OECD, 1997). Somaclonal variation (genetically dissimilar individuals derived from vegetative propagation, especially common after tissue culture in which a callus stage is included) is mitigated in several steps throughout the event selection process. Initially, a large number of transformation events are produced. The events are carefully observed by trained personnel, and those exhibiting phenotypes with notably poor vigor or off-types are removed. Any potential impact of somaclonal variation would be addressed in replicated field trials where events are grown in several geographic regions and scouted for undesirable anomalies and off-types. This selection process is conducted by experienced agronomists who observe the transformed events and compare with commercial varieties.

Example 4. Genetic Characterization of V11

Figure 5:
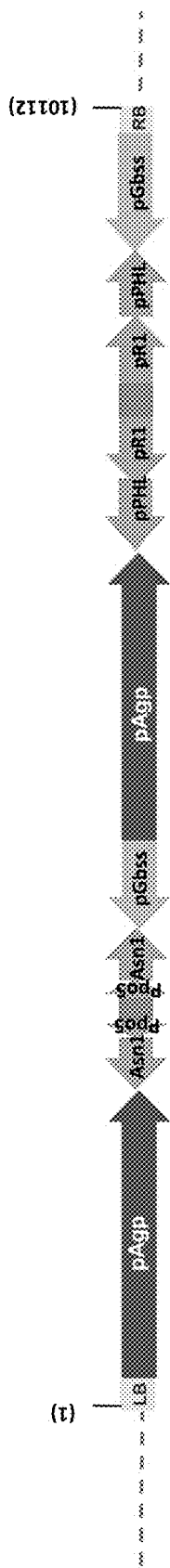
FIG. 5 shows the structure of the T-DNA insert within the genome of V11.

V11 contains an insert derived from transformation with the construct pSIM1278. Molecular analyses demonstrated that V11 contains a single, intact copy of the pSIM1278 insert with a 14-bp deletion of the left border region and a 3-bp deletion of the right border region within the Snowden genome (FIG. 5). V11 contains a stable, well-characterized insert at a single locus with no backbone DNA present. The insert is genetically stable across generations.

A detailed characterization of V11 included: (1) Southern blot verification that the pSIM1278 T-DNA insert integrated into a single genomic locus; (2) Structural determination of the insert by combining the Southern blot analyses with PCR and sequencing analyses (see Molecular Methods); (3) Confirmation of absence of pSIM1278 backbone sequence; (4) Confirmation of genetic stability of the insert across generations.

Characterization of Insert Number in V11

Figure 6:
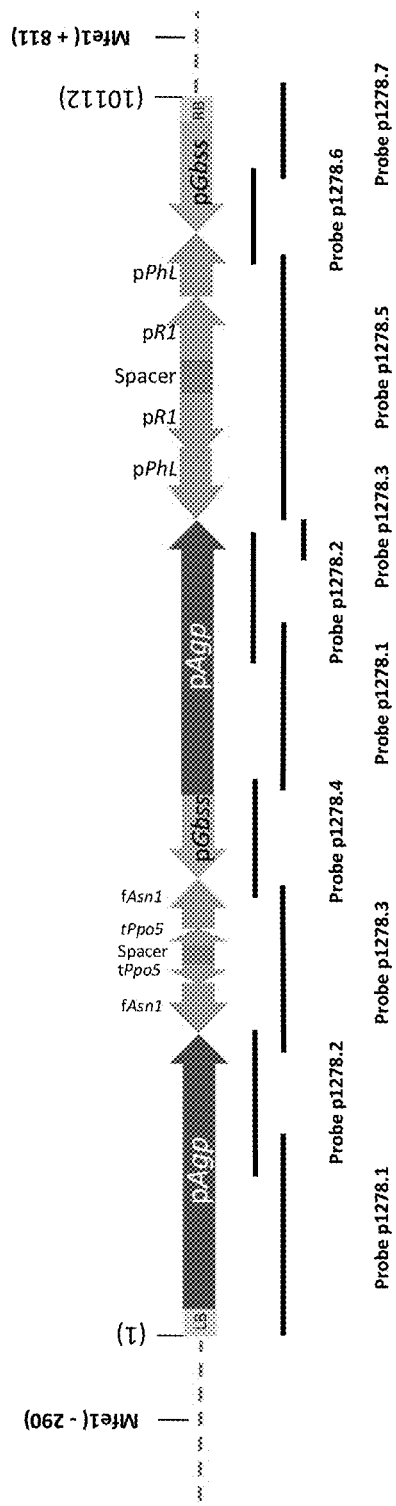
FIG. 6 shows a schematic of pSIM1278 T-DNA along with a set of 7 overlapping probes that cover the entire insert. The flanking regions (dashed lines) and location of MfeI restriction sites are indicated.

To assess the number of inserts derived from pSIM1278 in V11, a series of overlapping probes were designed to cover the entire length of the original T-DNA and used to analyze the genome of V11 by Southern blotting. Genomic DNA was digested with the restriction enzyme, MfeI, which does not cut within the T-DNA itself, and thus results in DNA fragments containing an entire insert along with its adjacent plant genomic DNA (FIG. 6).

Figure 7:
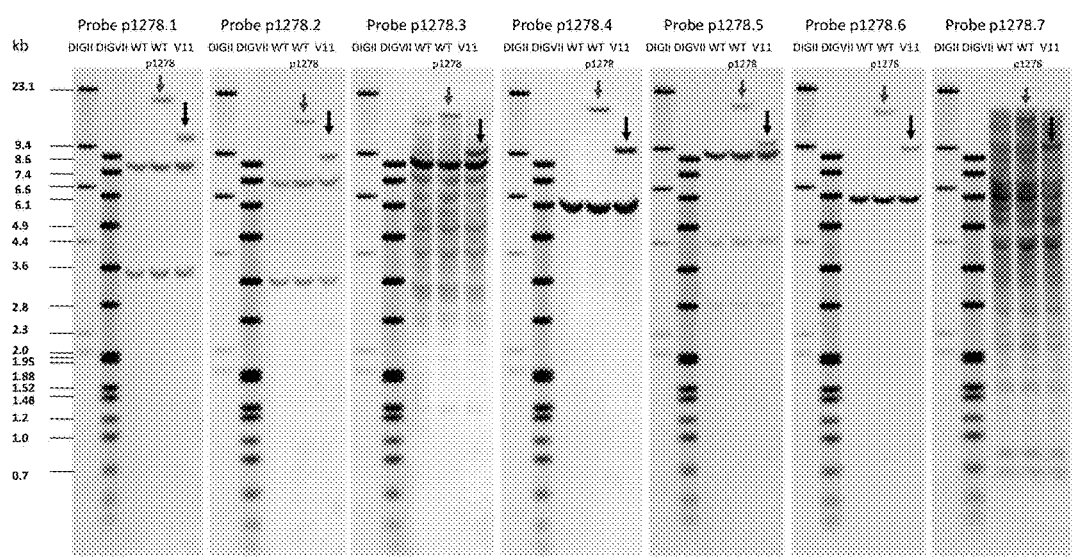
FIG. 7 shows Southern blots of MfeI-digested genomic DNA isolated from Snowden V11 (V11), Snowden control (WT), and Snowden control spiked with pSIM1278-digested plasmid DNA (WT p1278). The restriction enzyme, MfeI, cuts in the flanking region and not within the pSIM1278 T-DNA insert itself. Thus, the entire T-DNA insert is contained within the single band migrating above the 9.4 kb molecular weight marker (black arrows). A copy number control was included by spiking pSIM1278 construct DNA into a Snowden conventional control sample at a concentration of approximately 1 copy/genome prior to digestion (blue arrows). The molecular weight markers, DIGIT and DIGVII, are shown in the first two lanes at the left of each gel, respectively. The expected pSIM1278 insert fragment is indicated by a black arrow in each blot. DNA was separated on agarose gels (TAE) using extended electrophoresis to ensure good separation.

As shown in the Southern blots presented in FIG. 7, only a single band of consistent size (~11 kb) was observed as specific for V11 using each probe. A copy number and sensitivity control was included by spiking approximately a single genome equivalent of the pSIM1278 construct into a sample of Snowden control DNA (WT p1278). This control ensures the probe sensitivity is capable of detecting a single insert in the genome. The location of the MfeI restriction sites and those described in FIG. 8 were confirmed by identification and sequencing of the junction regions and flanking sequence using standard molecular approaches (see Molecular Methods). Collectively, these data indicate that transformation with pSIM1278 resulted in a single insert flanked by the indicated MfeI sites in the Snowden genome.

Characterization of Copy Number and Structure of the DNA Insert in V11

The Southern blot analyses included a set of probes that hybridize to elements contained within the T-DNA insert, but also recognize endogenous sequence within the plant genome. The probes were used to analyze the copy number and structure by comparing the restriction digest banding patterns of genomic DNA isolated from V11 with the Snowden conventional variety.

Figure 8:
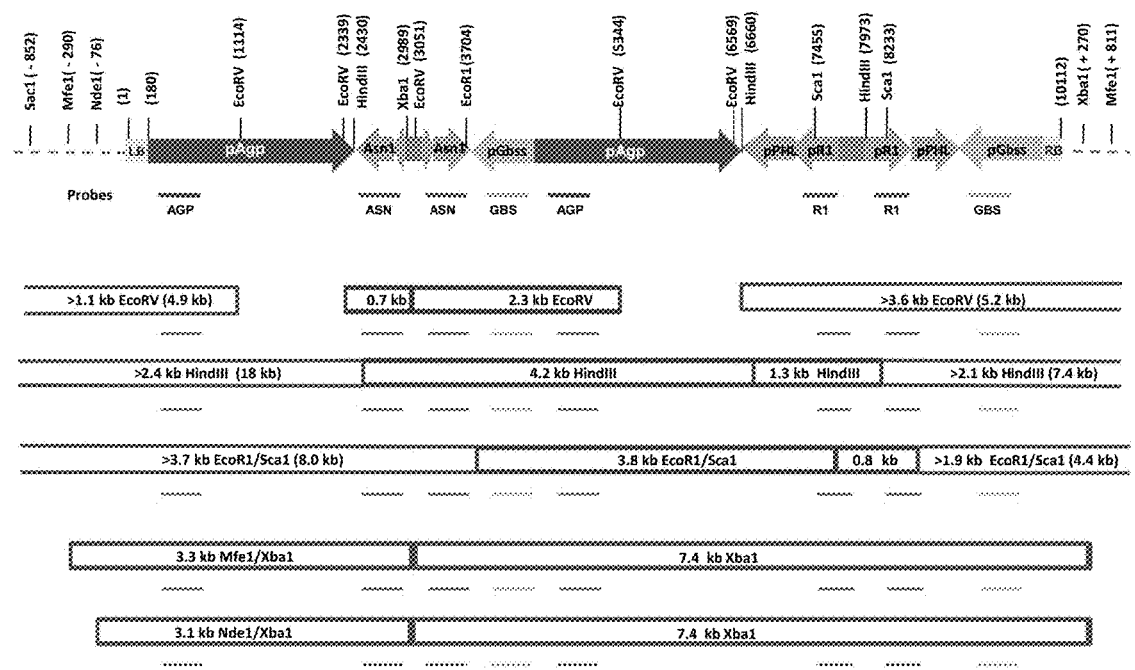
FIG. 8 represents the structure of the insert associated with the pSIM1278 construct, including designated restriction sites. The digestion pattern for selected enzymes is shown as colored boxes with the digest and fragment size indicated. The probes that are expected to detect each digestion product are indicated below the fragment with a colored line. All expected probe binding sites are indicated by bands, but only the digest/probe combinations necessary to support the model are shown. Red boxes denote internal bands (IB) associated with the original pSIM1278 DNA construct. Blue closed boxes indicate bands of known sizes due to identification of restriction sites within flanking DNA. Open-ended blue boxes indicate junction bands where the second restriction site is unknown. The estimated size of junction bands identified on Southern blots is indicated in parenthesis for all junction bands.

The T-DNA insert is summarized in FIG. 8 along with the probes and their binding sites, pertinent restriction sites, and restriction fragments corresponding to the digests used in the analysis. The bands associated solely with the T-DNA insert (internal bands) are depicted as red boxes whereas bands linking the insert to the flanking region (junction bands) are depicted in blue. The expected size of each band is provided for cross-reference with the Southern blots provided in FIGS. 9-14.

Figure 9:
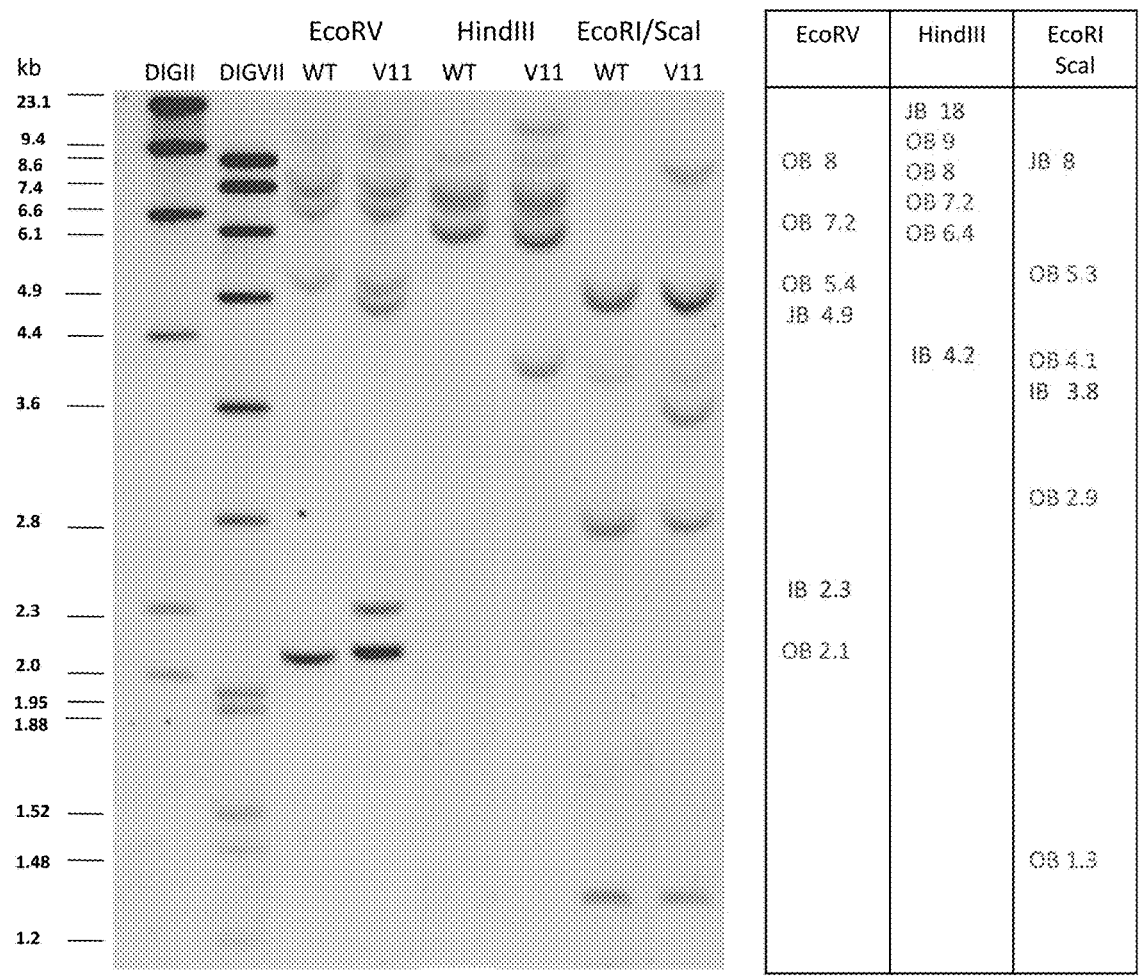
FIG. 9 shows Snowden genomic DNA hybridization with the AGP probe. Genomic DNA of Snowden control (WT) and V11 was digested with EcoRV, HindIII, and EcoRI/ScaI and hybridized with the AGP probe. Size of the DigII and DigVII molecular weight markers are indicated adjacent to the blot image. The estimated sizes of bands are summarized in the table and classified into three groups based on the structure of the DNA insert: original endogenous bands (OBs, in green), internal bands (IBs, in red) and the junction bands (JBs, in blue). All molecular weights are presented in kilobases (kb).
Figure 10:
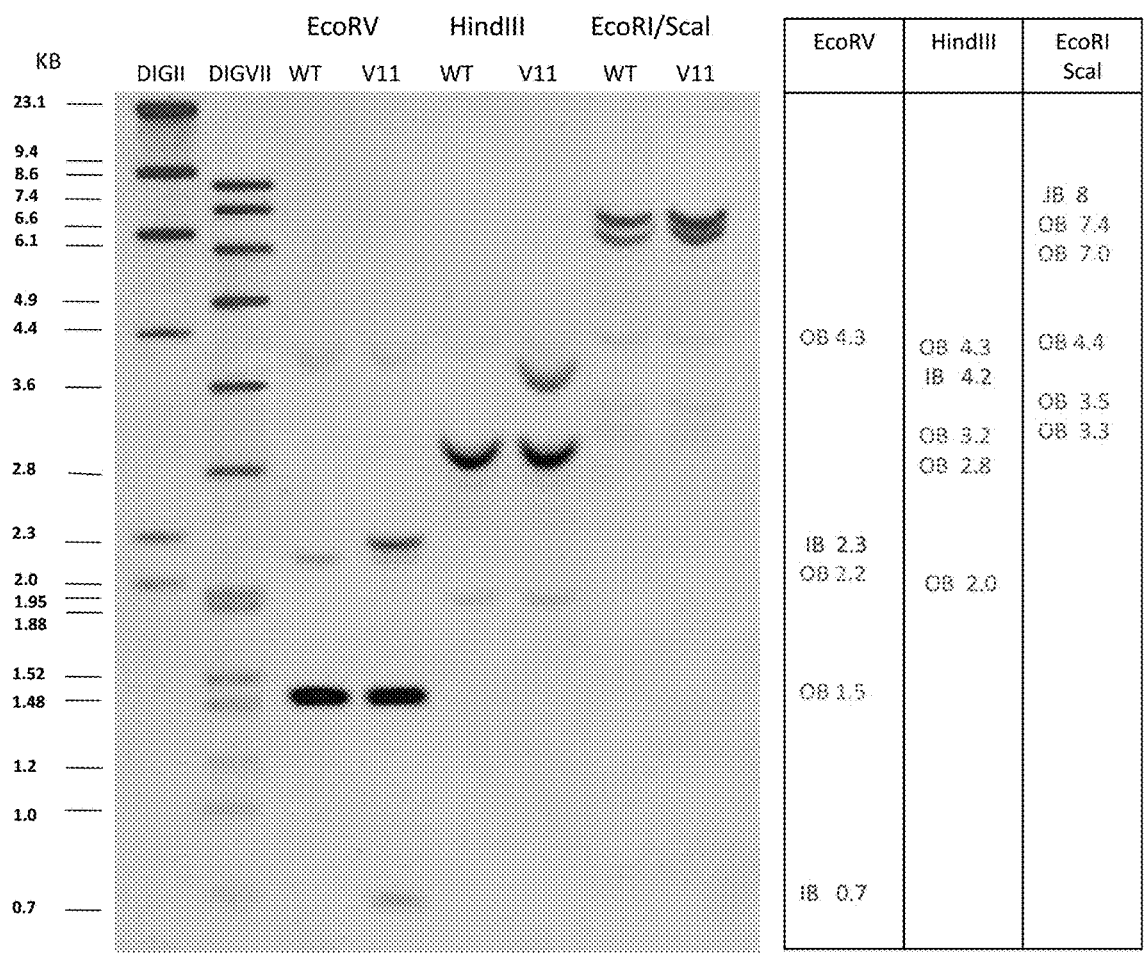
FIG. 10 shows Snowden genomic DNA hybridization with the ASN Probe. Genomic DNA of Snowden control (WT) and V11 was digested with EcoRV, HindIII, and EcoRI/ScaI and hybridized with the ASN probe. Size of the DigII and DigVII molecular weight markers are indicated adjacent to the blot image. The estimated sizes of bands are summarized in the table and classified into three groups based on the structure of the DNA insert: original endogenous bands (OBs, in green), internal bands (IBs, in red) and the junction bands (JBs, in blue). All molecular weights are presented in kilobases (kb).
Figure 11:
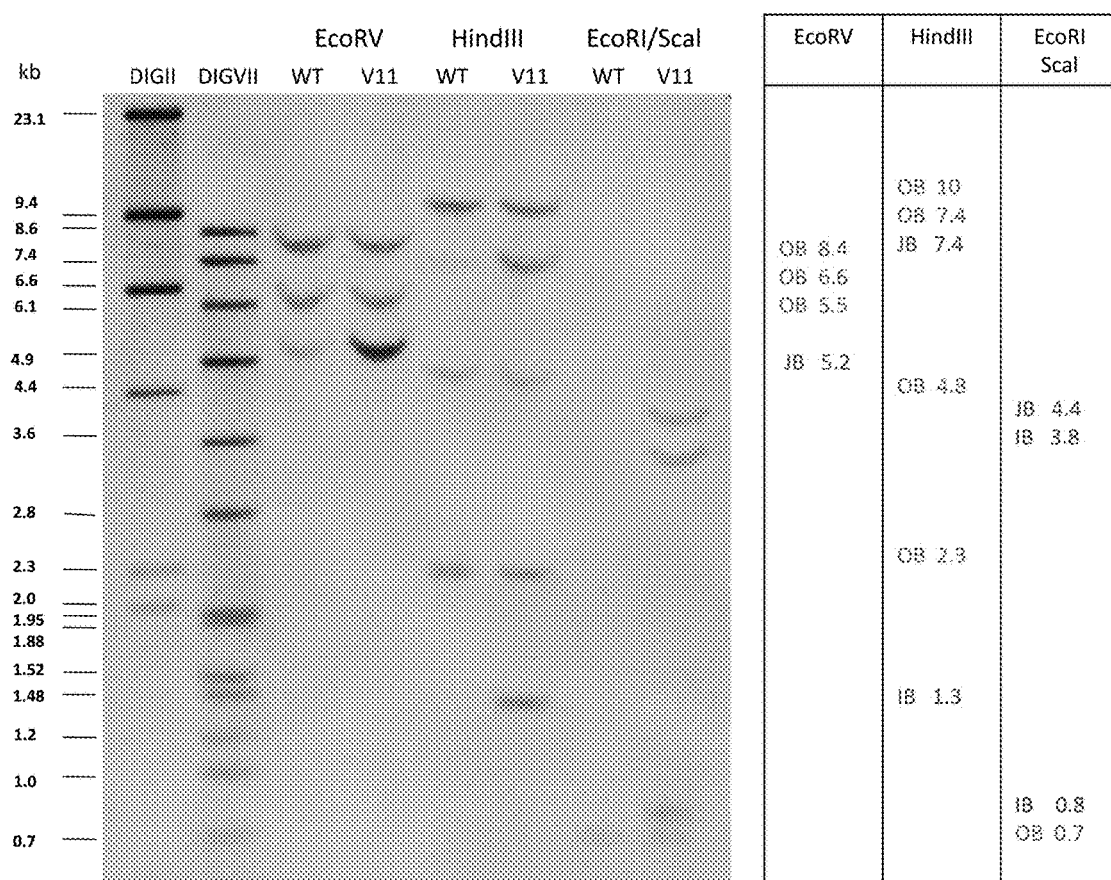
FIG. 11 shows Snowden genomic DNA hybridization with the R1 Probe. Genomic DNA of Snowden control (WT) and V11 was digested with EcoRV, HindIII, and EcoRI/ScaI and hybridized with the R1 probe. Size of the DigII and DigVII molecular weight markers are indicated adjacent to the blot image. The estimated sizes of bands are summarized in the table and classified into three groups based on the structure of the DNA insert: original endogenous bands (OBs, in green), internal bands (IBs, in red) and the junction bands (JBs, in blue). All molecular weights are presented in kilobases (kb).
Figure 12:
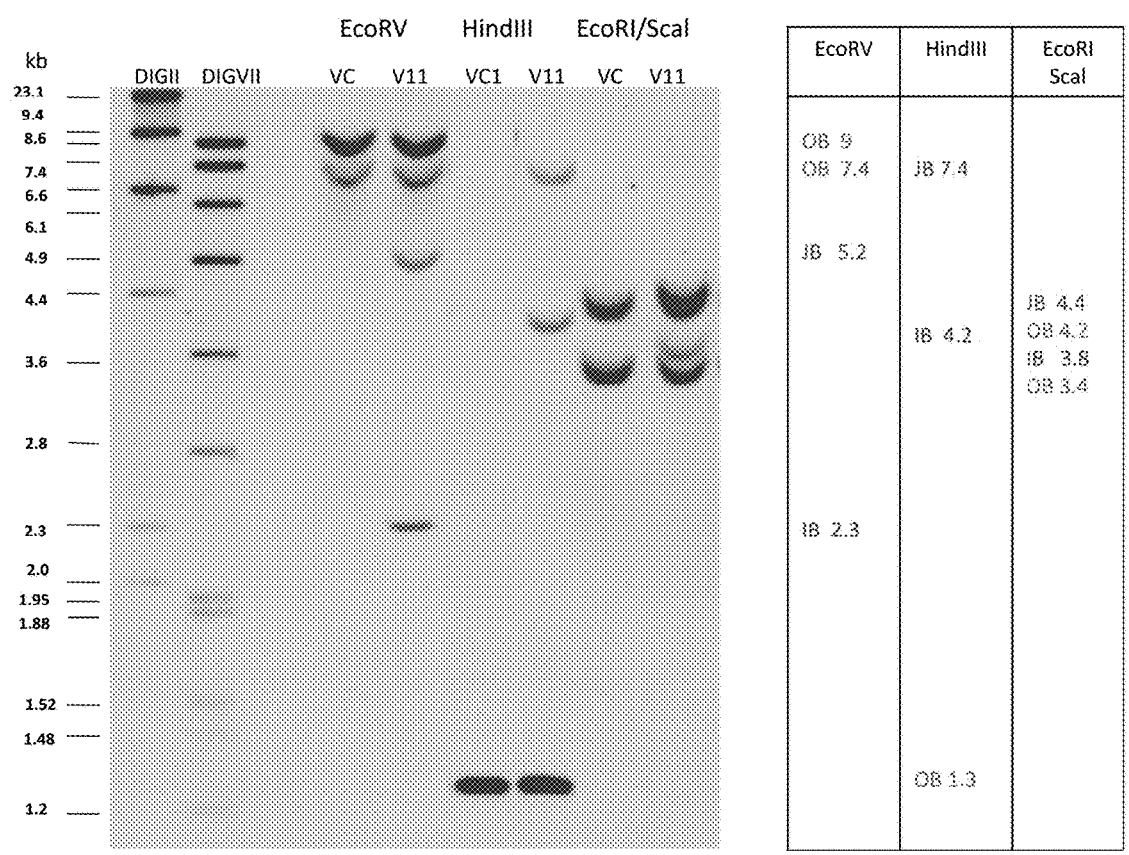
FIG. 12 shows Snowden genomic DNA hybridization with the GBS Probe. Genomic DNA of Snowden control (WT) and V11 was digested with EcoRV, HindIII, and EcoRI/ScaI and hybridized with the GBS probe. Size of the DigII and DigVII molecular weight markers are indicated adjacent to the blot image. The estimated sizes of bands are summarized in the table and classified into three groups based on the structure of the DNA insert: original endogenous bands (OBs, in green), internal bands (IBs, in red) and the junction bands (JBs, in blue). All molecular weights are presented in kilobases (kb).

As predicted, the expected internal bands were detected by the appropriate probes. The 0.7 kb EcoRV band was uniquely detected by the ASN probe (FIG. 10), whereas the 2.3 kb EcoRV and 4.2 kb HindIII bands were detected by AGP, ASN, and GBS probes (FIGS. 9, 10, and 12). The 3.8 kb EcoRI/ScaI band was present in blots detected by AGP, R1, and GBS (FIGS. 9, 11, and 12, respectively). Lastly, as expected, the 1.3 kb HindIII and 0.8 kb EcoRI/ScaI bands were only detected by the R1 probe (FIG. 11). These data confirm the internal structure of the pSIM1278 insert within the V11 genome.

Figure 13:
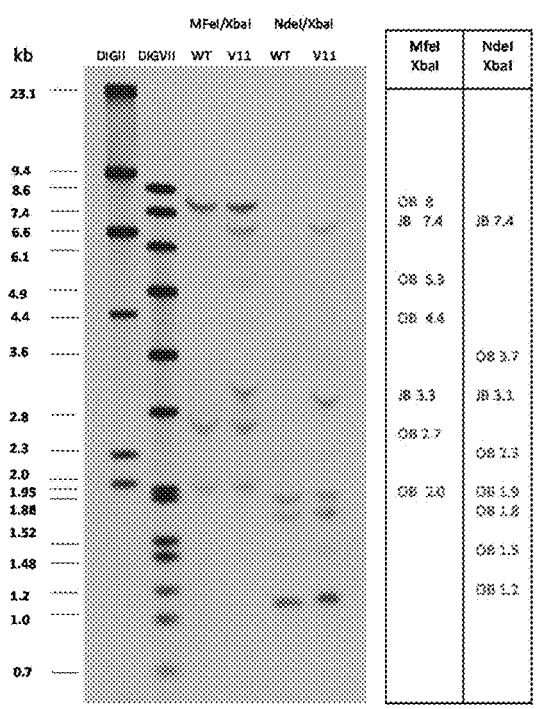
FIGS. 13A and 13B show Snowden genomic DNA hybridization with the AGP and ASN probes. Genomic DNA of Snowden control (WT) and V11 was digested with MfeI/XbaI and NdeI/XbaI and hybridized with either the AGP (FIG. 13A) or ASN (FIG. 13B) probe. Size of the DigII and DigVII molecular weight markers are indicated adjacent to the blot image. The estimated sizes of bands are summarized in the table and classified into groups based on the structure of the DNA insert: original endogenous bands (OBs, in green) and the junction bands (JBs, in blue). All molecular weights are presented in kilobases (kb).
Figure 13:
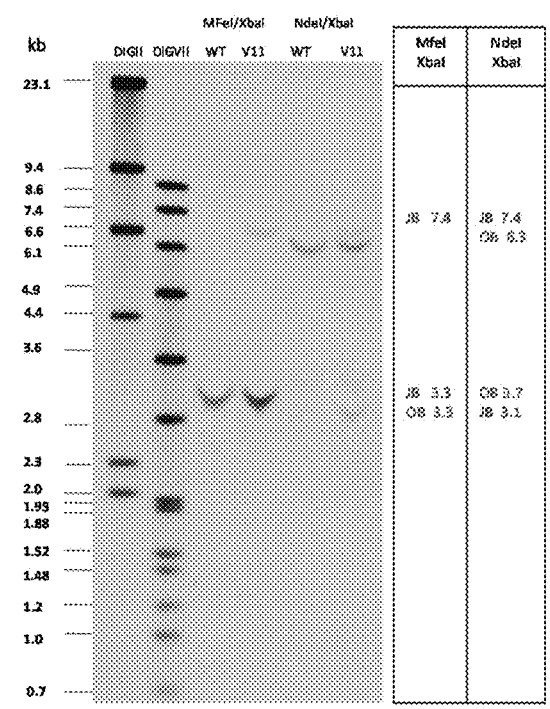
Figure 14:
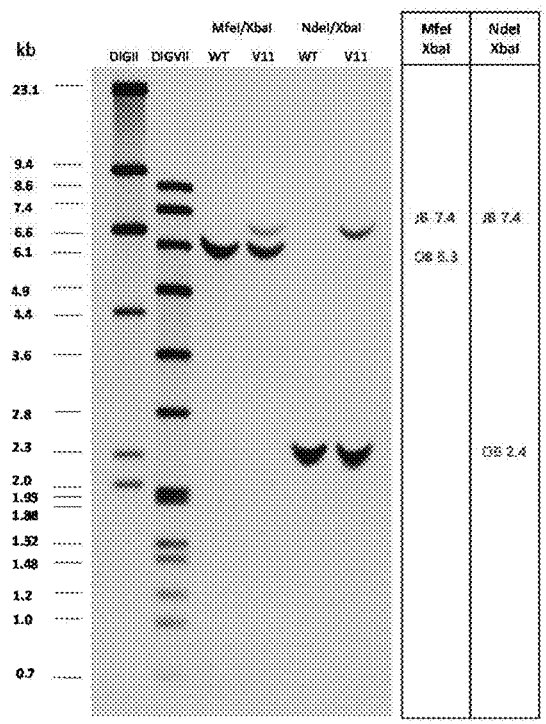
FIGS. 14A and 14B show Snowden genomic DNA hybridization with the GBS and R1 probes. Genomic DNA of Snowden control (WT) and V11 was digested with MfeI/XbaI and NdeI/XbaI and hybridized with either the GBS (FIG. 14A) or R1 (FIG. 14B) probe. Size of the DigII and DigVII molecular weight markers are indicated adjacent to the blot image. The estimated sizes of bands are summarized in the table and classified into three groups based on the structure of the DNA insert: original endogenous bands (OBs, in green) and the junction bands (JBs, in blue). All molecular weights are presented in kilobases (kb).
Figure 14:
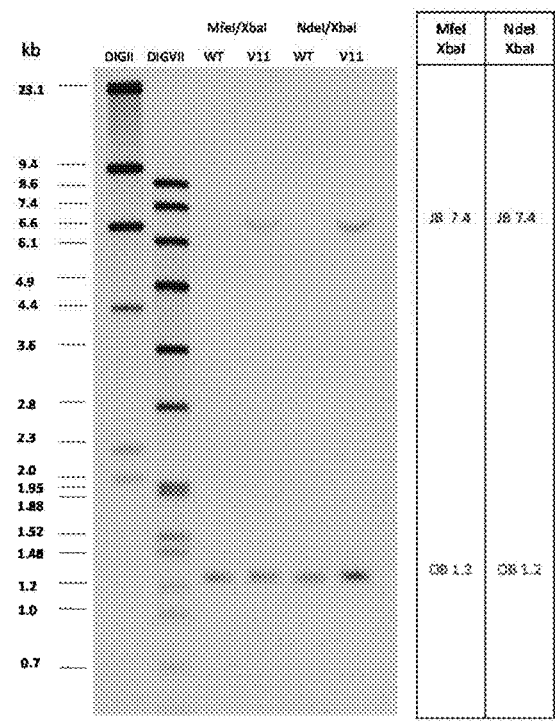

Identification of the left and right junction regions allowed mapping of a number of additional restriction sites as shown in FIG. 8. These restriction sites were used to conclusively map the left and right junction regions of the insert using two sets of digests, MfeI/XbaI and NdeI/XbaI. The presence of 3.3 kb MfeI/XbaI and 3.1 kb NdeI/XbaI bands in blots probed with AGP and ASN (FIG. 13) confirmed the structure of the left side of the insert as both bands connect the already mapped internal bands to the left flanking region. Similarly, the 7.4 kb band produced by XbaI cleavage in both digests connected the internal bands to the right flanking region. This band was detected by all four probes as expected (FIGS. 13 and 14). Higher molecular weight fragments have a tendency to migrate slightly faster than expected in DNA isolated from potatoes, which accounts for the slight difference between expected and observed migration of the 7.4 kb band.

Because the flanking regions did not identify restriction sites for EcoRV, EcoRI, or ScaI in the neighboring sequence, the actual size of junction bands associated with each of those digests could not be predicted. However, a minimal size was calculated based upon the distance between the known restriction sites and the end of the flanking regions (shown in FIG. 8 along with estimates of the actual size observed). In all cases, the observed junction bands were greater than the minimal predicated band size, which further supports the structure presented in FIG. 8. Importantly, only one junction band was identified by the AGP probe associated with the left side of the insert (FIGS. 9 through 12). Likewise, a single junction band was identified in each of these digests associated with the right side using probes GBS and R1 (FIGS. 11 and 12). These data further support a single insertion model.

A summary of these data is provided in Table 3 where the expected and observed band sizes are compared for each digest and associated probe. The number, size, and intensity of observed bands exactly matches what is expected for a single insert of an intact pSIM1278 DNA insert in V11 as shown in FIG. 5.

TABLE 3

Predicted and Observed Bands Based on Southern Blots for pSIM1278

| Enzyme | Probe | Expected sizes (kb)[1] | Observed sizes (kb)[2] | References |
|---|---|---|---|---|
| EcoRV | AGP | >1.1, 2.3 | 4.9, 2.3 | FIG. 9 |
|  | ASN | 0.7, 2.3 | 0.7, 2.3 | FIG. 10 |
|  | R1 | >3.6 | 5.2 | FIG. 11 |
|  | GBS | >3.6, 2.3 | 5.2, 2.3 | FIG. 12 |
| HindIII | AGP | >2.4, 4.2 | 18.0, 4.2 | FIG. 9 |
|  | ASN | 4.2 | 4.2 | FIG. 10 |
|  | R1 | >2.1, 1.3 | 7.4, 1.3 | FIG. 11 |
|  | GBS | >2.1, 4.2 | 7.4, 4.2 | FIG. 12 |
| EcoRI/ScaI | AGP | >3.7, 3.8 | 8.0, 3.8 | FIG. 9 |
|  | ASN | >3.7 | 8.0 | FIG. 10 |
|  | R1 | >1.9, 3.8, 0.8 | 4.4, 3.8, 0.8 | FIG. 11 |
|  | GBS | >1.9, 3.8 | 4.4, 3.8 | FIG. 12 |
| MfeI/XbaI | AGP | >2.9, >7.1 | 3.3, 7.4 | FIG. 13A |
|  | ASN | >2.9, >7.1 | 3.3, 7.4 | FIG. 13B |
|  | R1 | >7.1 | 7.4 | FIG. 14A |
|  | GBS | >7.1 | 7.4 | FIG. 14B |
| NdeI/XbaI | AGP | >2.9, >7.1 | 3.1, 7.4 | FIG. 13A |
|  | ASN | >2.9, >7.1 | 3.1, 7.4 | FIG. 13B |
|  | R1 | >7.1 | 7.4 | FIG. 14A |
|  | GBS | >7.1 | 7.4 | FIG. 14B |

Absence of pSIM1278 Backbone Sequence in V11

The following methods were used to establish that backbone portions of the pSIM1278 construct were not present: 1) Plants with phenotypes associated with the negative selectable isopentenyl isomerase (ipt) marker gene in the construct backbone were discarded; and 2) Southern blots were used to confirm absence of the backbone DNA.

As described below, the results demonstrate that V11 does not contain backbone sequence.

*Agrobacterium*-mediated transformation often results in transfer of construct backbone DNA, in addition to the intended region of DNA positioned between the left and right borders (LB and RB) of the plant-derived DNA insert. To reduce the number of events that must be characterized molecularly, a phenotypic screen for plants was employed that contained the *Agrobacterium* ipt gene, which is present in the construct backbone (Richael et al., 2008). When this gene is introduced into potatoes, its overexpression results in stunted growth, abnormal leaves, or the inability to root due to overproduction of cytokinin. Thus, these phenotypes were used to select against plants containing backbone DNA. V11 did not present abnormal growth phenotypes and was further characterized using molecular methods to show that it did not contain any backbone sequences integrated into the plant genome.

Figure 15:
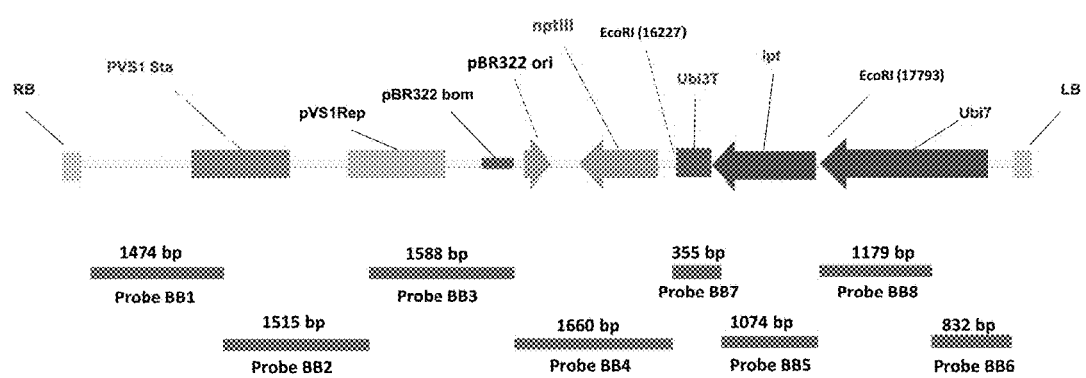
FIG. 15 shows probes for the backbone of pSIM1278. The backbone DNA is spanned by the probes shown as blue rectangles. Probes BB1-BB5 are specific to the backbone DNA. Probes BB6-BB8 detect both backbone DNA and sequence from the potato genome (Ubi7 promoter, Ubi3 terminator, and Ubi7 promoter, respectively).
Figure 16:
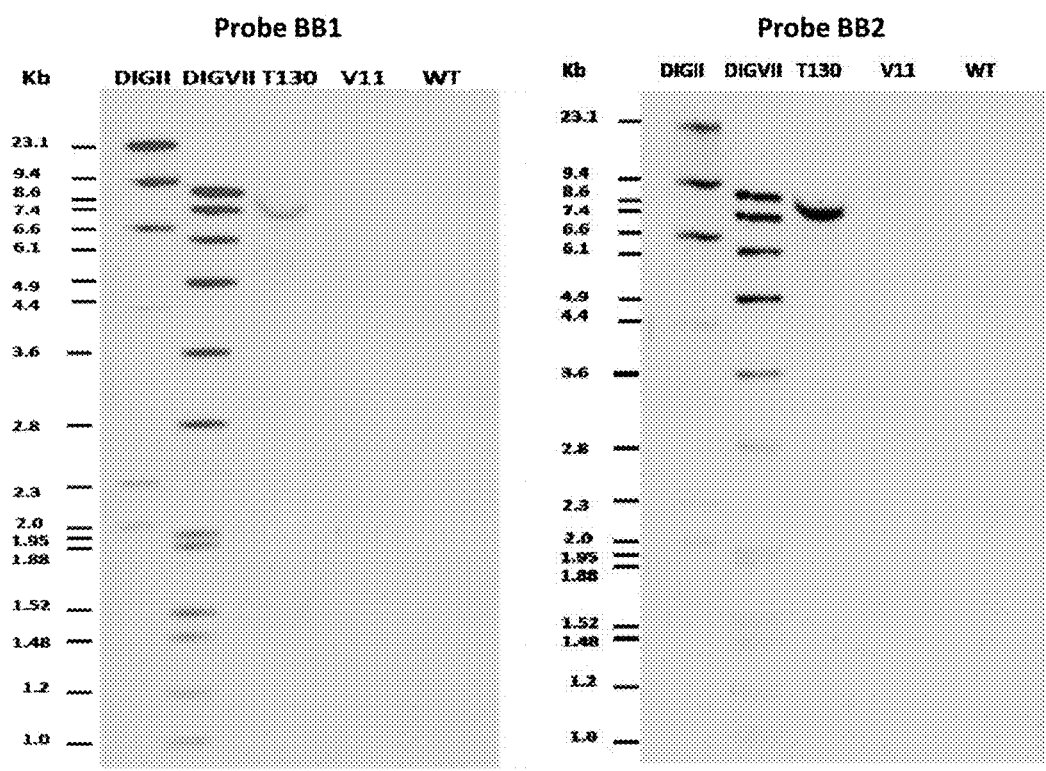
FIG. 16 shows Southern blot analysis of construct backbone DNA using backbone probes BB1 and BB2. Genomic DNA was digested with EcoRI and analyzed by Southern blot using probes BB1 and BB2. WT=Snowden control, V11=Event V11, T130=positive control containing backbone DNA. Lanes 1 and 2 are molecular weight markers (DIG II, and DIGVII, respectively) with sizes indicated next to gel in kilobases (kb).
Figure 17:
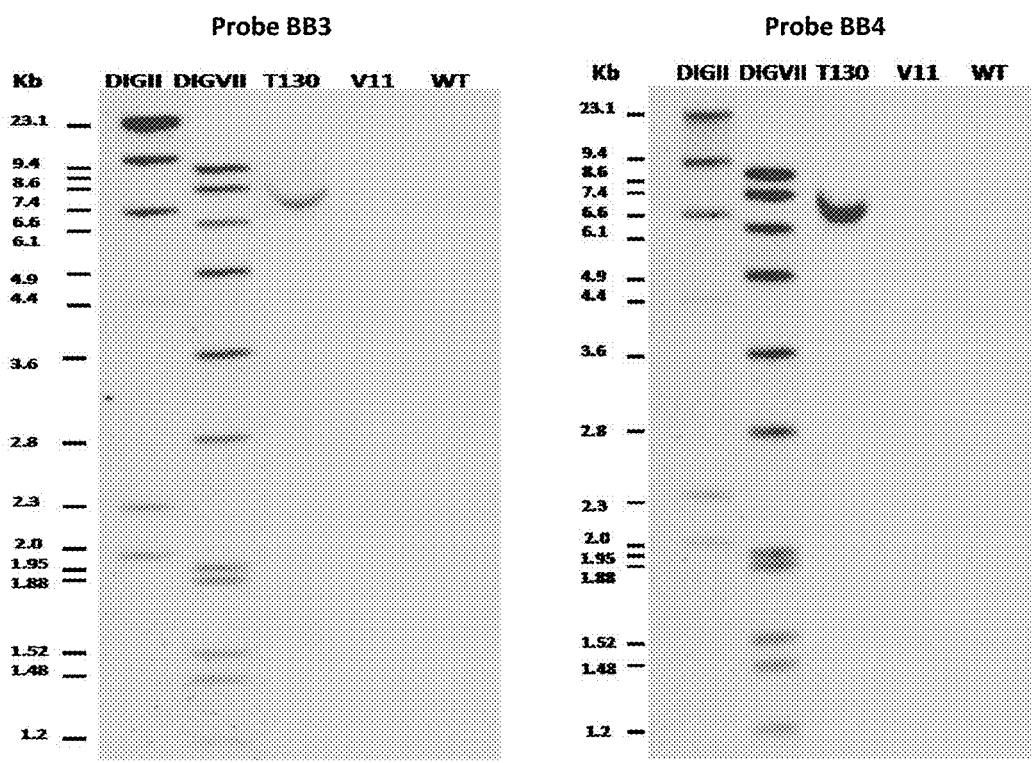
FIG. 17 shows Southern blot analysis of construct backbone DNA using backbone probes BB3 and BB4. Genomic DNA was digested with EcoRI and analyzed by Southern blot using probes BB3 and BB4. WT=Snowden control, V11=Event V11, T130=positive control containing backbone DNA. Lanes 1 and 2 are molecular weight markers (DIG II, and DIGVII, respectively) with sizes indicated next to gel in kilobases (kb).
Figure 18:
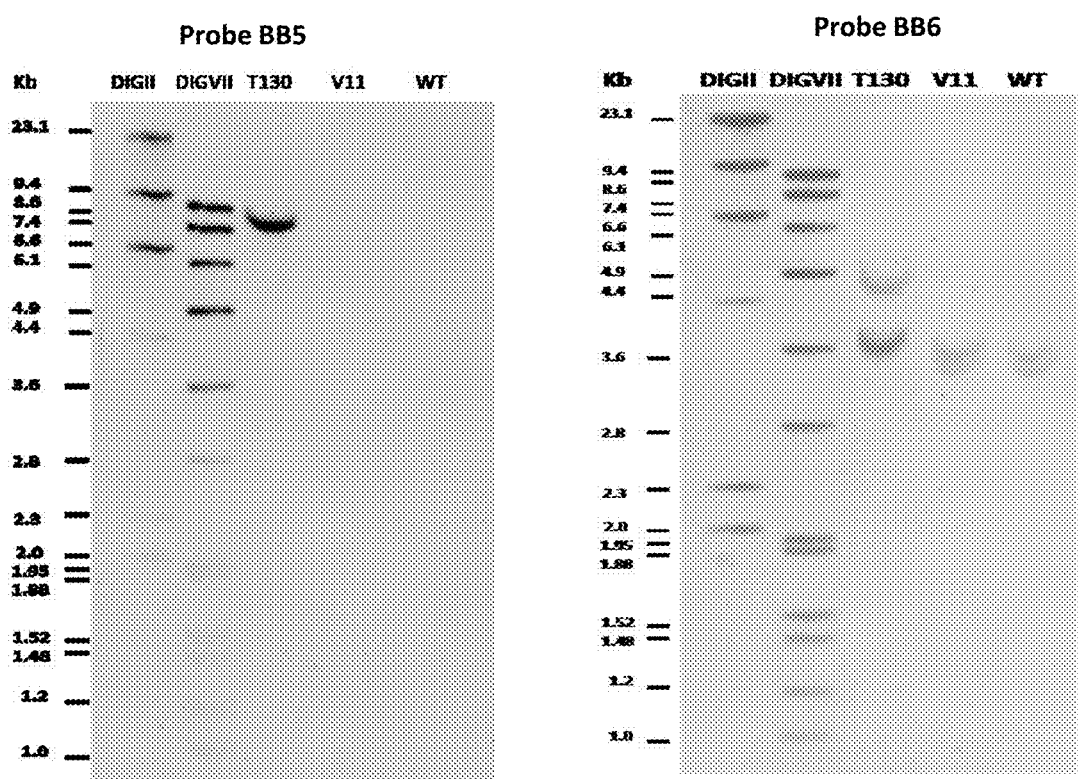
FIG. 18 shows Southern blot analysis of construct backbone DNA using backbone probes BB5 and BB6. Genomic DNA was digested with EcoRI and analyzed by Southern blot using probes BB5 and BB6. WT=Snowden control, V11=Event V11, T130=positive control containing backbone DNA. Lanes 1 and 2 are molecular weight markers (DIG II, and DIGVII, respectively) with sizes indicated next to gel in kilobases (kb).
Figure 19:
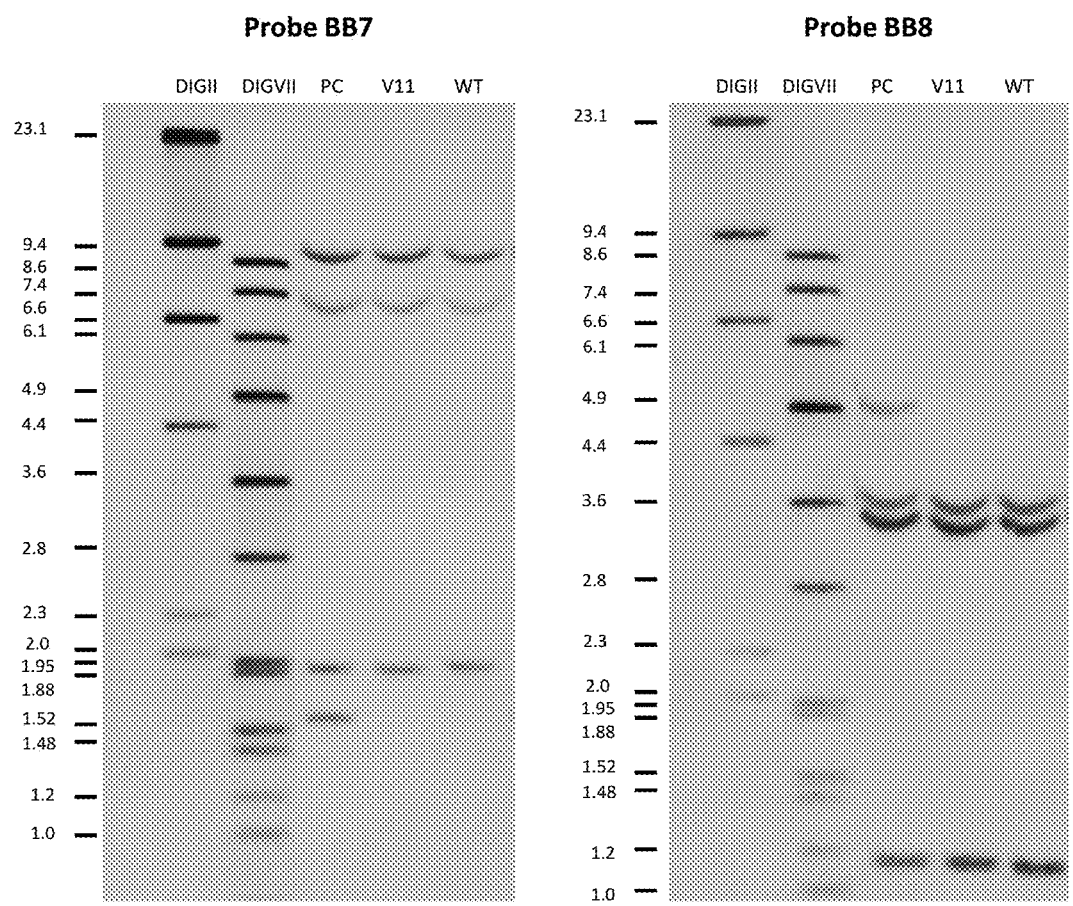
FIG. 19 shows Southern blot analysis of construct backbone DNA using backbone probes BB7 and BB8. Genomic DNA was digested with either EcoRI (probe BB7) or EcoRI/ScaI (probe BB8) and analyzed by Southern blot. PC=Snowden genomic DNA spiked with pSIM1278 construct DNA, WT=Snowden control, V11=Event V11. Lanes 1 and 2 are molecular weight markers (DIG II, and DIGVII, respectively) with sizes indicated next to gel in kilobases (kb).

A series of Southern probes were designed to span the entire construct backbone to detect any backbone DNA in the genome of the transformed potatoes (FIG. 15). As the absence of DNA is based upon a lack of detection or amplification, a positive control (T130) event was developed, which contains an integrated copy of the entire construct backbone. Control genomic DNA samples from Snowden were included to distinguish between bands associated with the transformation and endogenous bands.

Genomic DNA isolated from V11, T130, and Snowden controls (WT) were digested with EcoRI and hybridized with probes BB1-6 (FIGS. 16-19). Probes BB1-5 were highly specific and only detected bands associated with the T130 positive control, whereas probe BB6 detected a pair of endogenous bands. These bands were expected since the region of the construct detected by this probe is derived from the potato Ubi7 promoter.

Similarly, the regions of the construct detected by probes BB7 and BB8 are derived from potato DNA, Ubi3 terminator and Ubi7 promoter, respectively. The Southern blot for probe BB7 was analyzed similar to probes BB1-6. However, to simplify the banding patterns when using probe BB8, genomic DNA was digested with both EcoRI and ScaI. In addition, the positive control for these blots consisted of Snowden genomic DNA spiked with pSIM1278 construct DNA. The probes detected three endogenous bands, in addition to the positive control in each sample. A review of all Southern blots with eight probes demonstrated that only the positive control, T130, contained unique backbone bands that hybridized with the probes (FIGS. 16-19).

Collectively, the Southern blot analyses showed the genome of V11 does not contain sequence from the backbone of construct pSIM1278.

Genetic Stability of the Insert Across Generations

T-DNA can be unstable in a transformed host where the instability rate ($0.5$-$5.9 \times 10^{-4}$) is associated with meiosis and meiotic recombination (Müller et al., 1987; Conner et al., 1998). Since potatoes are reproduced vegetatively and do not undergo meiosis, the T-DNA insert is expected to be genetically stable.

Figure 20:
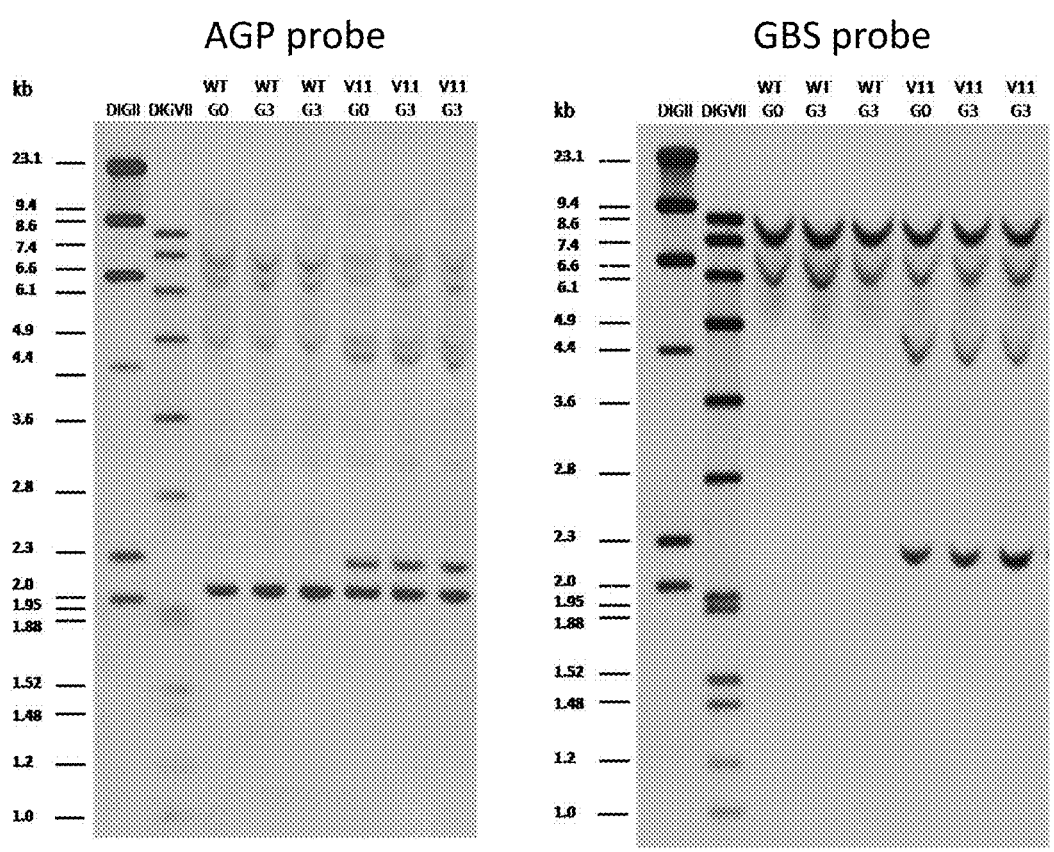
FIG. 20 shows Southern blots of EcoRV-digested genomic DNA with AGP and GBS probes. Genomic DNA (3 µg) was digested with EcoRV and probed for AGP (left) or GBS (right) sequence. Each blot compares DNA from the indicated generation to DNA from the initial transformant (G0). Snowden untransformed controls (WT), event V11 (V11). Genetic stability is established by the consistent digestion pattern between the original transformant (G0) and the G3 generation.

Genetic stability of the T-DNA insert in V11 was assessed by analyzing the structure using Southern blot analysis of genomic DNA isolated from G0 and G3 plants. Southern blots were performed on EcoRV-digested DNA as this digest produces independent bands corresponding to each end of the insert (e.g. 4.9 and 5.1 kb) along with an internal band (e.g. 2.3 kb) as described in FIG. 8 and Table 3. The AGP and GBS probes were used because, collectively, they hybridize to each of the three predicted bands, which includes the ends of the T-DNA insert. As expected, the banding pattern on Southern blots of EcoRV-digested DNA analyzed with the AGP and GBS probes was the same between G0 and G3 plants generated through clonal propagation (FIG. 20). Thus, the V11 insert is genetically stable.

Molecular analysis demonstrated that V11 contains a single, intact copy of the pSIM1278 insert with a 14-bp deletion of the left border region and 3-bp deletion of the right border region within the Snowden genome. The T-DNA insert consisted solely of sequence targeted for insertion and did not contain any detectable construct backbone DNA. The structure of the DNA insert was intact as in the original construct and was shown to be stable across generations. Given the demonstrated DNA insert stability in V11 over generations, it is likely that stability will be maintained during subsequent cycles of vegetative propagation.

Example 5. Gene Down-Regulation in V11

Silencing was achieved by introducing inverted repeats containing sequences derived from the genes and promoters targeted for silencing. Although there are a number of parallel pathways involved in double-stranded RNA mediated silencing, transcription of these inverted repeats is thought to be processed by the cellular machinery involved in the viral defense (Fusaro et al. 2006). V11 potatoes contain two unique cassettes, which contain sequence from a total of four different potato genes. The pSIM1278 construct consists of two gene silencing cassettes (see FIG. 2). One cassette contains an inverted repeat of sequence from two genes, asparagine synthetase-1 (Asn1) and polyphenol oxidase-5 (Ppo5). The second cassette includes sequence from the promoters of the starch associated genes, R1 (531-bp) and phosphorylase-L (PhL) (508-bp).

Both silencing cassettes are regulated by the same set of well-characterized and tissue-specific promoters from the Agp and Gbss genes of potato, which are highly active in tubers compared with photosynthetically-active tissues and roots (Nakata et al. 1994; Visser et al. 1991). Therefore, expression and gene silencing was expected to be most effective in and largely limited to tubers.

V11 was characterized using northern blot analysis to determine the effectiveness of the down-regulation of the four target genes: Asn1, R1, PhL, and Ppo5. The expression level of each target transcript was determined using RNA isolated from V11 and Snowden control (WT) tubers.

Figure 21:
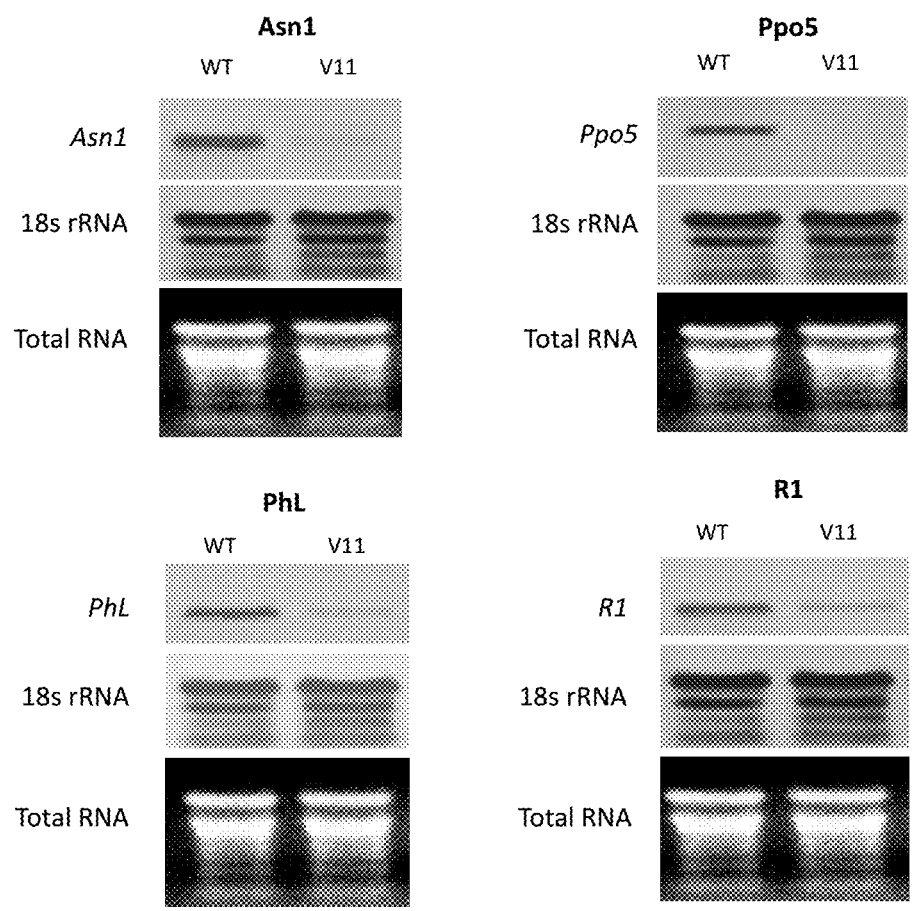
FIG. 21 shows Northern blot analysis of total RNA (20 µg) isolated from tubers of field-grown plants for V11 and the Snowden control (WT). Blots were hybridized with probes specific to the Asn1, Ppo5, PhL, or R1 transcripts (upper panels). A probe specific to the internal control 18s rRNA (middle panels) and ethidium bromide stained total RNA (lower panels) were used as internal and loading controls.

In tubers, the primary target tissue, robust down-regulation of Asn1 and Ppo5 and partial down-regulation of PhL and R1 was observed (FIG. 21). Similar down-regulation of the four genes in tubers of V11 occurred in the previously deregulated events (Collinge and Clark 2013). Gene down-regulation was assessed by northern blot analysis in other tissues (leaves, stems, flowers, and roots) and is summarized in Table 4.

TABLE 4

| Gene Down-regulation in V11 | | | | | |
|---|---|---|---|---|---|
| | Tubers | Leaf | Stems | Roots | Flowers |
| Asn1 | Yes | Yes | Yes | No | No |
| R1 | Yes | No | No | No | No |
| PhL | Yes | No | No | No | No |
| Ppo5 | Yes | No | No | No | No |

Previous studies have shown that Ppo gene silencing reduces the amount of associated protein to levels undetectable by western blot analysis (Llorente et al. 2011). Similarly, silencing of the R1 gene diminished accumulation of a ~160 kDa protein that is at least partially bound to starch granules (Lorberth et al. 1998).

Example 6. Comparative Assessment of V11 Potato

Phenotypic and compositional comparative assessments were conducted to determine the safety of V11 relative to conventional potatoes. These assessments used conventional potatoes for comparison to V11 and established the safety of V11 relative to potato varieties that have a long history of safe use in the environment and as food and feed.

To ensure accurate evaluations of V11, proper selection of comparator varieties was important. For V11, the most relevant comparator is Snowden, its parental variety. The only difference between V11 and Snowden is that V11 underwent transformation and contains a pSIM1278 insert. Statistical analysis was used to determine whether V11 was different from its parental control, Snowden.

Other important comparators include additional varieties of conventional potatoes, which were grown in typical potato-growing regions. These represent a wide range of potato varieties that are planted commercially and were used to assess the normal range of phenotypic and compositional variation. In some cases, the data obtained from the comparator varieties was used to generate a statistical tolerance interval. Scientific literature was used to generate a range of values for compositional analytes of potatoes.

A summary of how the comparative assessment data were interpreted after statistical analysis is as follows:

When p-values were available and the p-value indicated no statistical significance, it was unlikely that there was a difference that was meaningful, and the assessment was considered complete.

If the p-value indicated statistical significance or if a p-value was not present, the mean value of the event was compared to the tolerance interval, conventional variety range, or the combined literature range. If the mean value for V11 was within any of those, we concluded that V11 was within the natural variation of potatoes and that the difference was unlikely to be meaningful.

If the mean value of the event was outside the ranges, further consideration was given to the difference in the context of phenotype or composition equivalence.

The phenotype and compositional comparative assessments of V11 are discussed further below. The analyses indicate that V11 was comparable to its parent variety, Snowden, and other conventional potatoes with respect to the characteristics measured. Overall, these analyses indicate that V11 is as safe and nutritious as conventional potato varieties and poses no more risk than conventional potato varieties in food, feed, and the environment.

Example 7. Phenotypic Performance and Field Observations

Potato variety V11 addresses the need of the potato industry to improve quality by reducing expression of the enzyme responsible for black spot bruise and to reduce acrylamide through lowering the concentration of the reactants, namely asparagine and reducing sugars. Potato variety V11 was transformed with nucleic acid sequences that are native to the potato plant genome and does not contain foreign DNA, *Agrobacterium* DNA, viral markers or vector backbone sequences. In addition, agronomic studies were conducted to ensure that the events grew the same as conventional controls, with the exception of the characteristics associated with the trait.

Observations throughout the growing season allowed for a thorough assessment of: 1) Agronomic/phenotypic characteristics; 2) Tuber characteristics; 3) Biotic and abiotic stress susceptibility; and 4) Volunteer potential.

These assessments demonstrate that the addition of the DNA insert in V11 did not result in unintended effects associated with weediness or pest-like characteristics. In addition, the phenotypic comparability between V11 and Snowden also supports the conclusion of lack of meaningful somaclonal variation in V11.

Field Trial Locations

During 2012 and 2013, V11 and its parental control, Snowden, were grown at multiple locations representing the major production areas for potatoes (Table 5). At some locations, additional conventional varieties were also grown. The agronomic practices and pest control measures used were location-specific and were typical for potato cultivation. They were recommended by both regional potato extension specialists and agronomists and they related to all aspects of soil preparation, fertilizer application, irrigation, and pesticide-based control methods.

TABLE 5

| | | | | | | | |
|---|---|---|---|---|---|---|---|
| Field Trial Locations | | | | | | | |
| Year | State | County | Material Tested[1] | Trial Design[2] | Rows × Planted Tubers/ Row | Seed Type | Regional Specifics |
| 2012 | FL | St. Johns | V11<br>Snowden Control | RCB, 3 reps | 4 × 20 | Mini-tubers | Typical for Florida, which produces almost 8 million cwt/year, mainly for the chip and fresh potato industry, with harvests in spring. |
| 2012 | WI | Adams | V11<br>Snowden Control | RCB, 3 reps | 3 × 20 | Mini-tubers | Typical for Wisconsin, which produces about 20 million cwt/year, for both the chip and fresh potato industry, with harvests in fall. Large areas are dominated by muck soils. |
| 2013 | | | V11<br>Snowden Control<br>Gala<br>Purple Majesty<br>C0095051-7W<br>Norkotah | RCB, 4 reps | 4 × 20 | Tubers | |

TABLE 5-continued

Field Trial Locations

| Year | State | County | Material Tested[1] | Trial Design[2] | Rows × Planted Tubers/ Row | Seed Type | Regional Specifics |
|---|---|---|---|---|---|---|---|
| 2012 | MI | Montcalm | V11 Snowden Control | RCB, 3 reps | 4 × 20 | Mini-tubers | Typical for Michigan, which produces about 15 million |
| 2013 | | | V11 Snowden Control Gala Purple Majesty C0095051-7W Norkotah | RCB, 4 reps | 4 × 20 | Tubers | cwt/year, for both the chip and fresh potato industry, with harvests in fall. The climate is characterized by mild temperatures and ample rain. |
| 2013 | WA | Grant | V11 Snowden Control Gala Purple Majesty C0095051-7W Norkotah | RCB, 4 reps | 4 × 20 | Tubers | Typical for Washington, which produces about 85 million cwt/year, mainly for the fry industry, with harvests in fall. Ideal growing conditions give rise to very high yields per acre. |
| 2013 | PA | Berks | V11 Snowden Control Gala Purple Majesty C0095051-7W Norkotah | RCB, 4 reps | 4 × 20 | Tubers | Typical for Pennsylvania, which produces about 2 million cwt/year, mainly for the chip industry, with harvests in fall. |

[1]The conventional varieties used were selected because they represent a range of common potato varieties that are currently planted commercially.
[2]RCB = Randomized Complete Block design Phenotypic and Tuber Assessment Results Summaries of phenotypic and tuber characteristics (yield and grading) of V11 and the Snowden control grown over two years are shown in Tables 6 and 7, respectively.

The phenotypic characteristics of V11 and the control are shown in Table 6. There were no statistical differences for any of the traits measured.

The yield and grading characteristics of V11 and the control are shown in Table 7. There were no statistical differences for total yield, U.S.#1 yield, tubers per plant, size A tubers, size B tubers, oversize tubers, pickout tubers, and specific gravity. Compared to its parental control, Snowden, V11 had fewer total internal defects (24.9% vs. 18.7%). This could be related to the efficacy provided by the PPO down-regulation and the absence of color in bruises or defects in V11. However, the mean of V11 for total internal defects fell within the conventional variety range. Fewer total internal defects would be considered a positive outcome and would not indicate increased plant pest potential.

Overall, the results demonstrate there are no major differences between V11 and its parental control, Snowden. These data support the conclusion that V11 is unlikely to have increased plant pest potential when compared to the control.

TABLE 6

Phenotypic Characteristics

| Characteristic | Variety | N | Mean | P-Value[1] | Standard Deviation | Conventional Variety Range[2] |
|---|---|---|---|---|---|---|
| Early Emergence (%) | Control | 24 | 62.5 | 0.8243 | 35.4 | 3.75-96.3 |
| | V11 | 25 | 61.0 | | 34.2 | |
| Final Emergence (%) | Control | 24 | 90.8 | 0.9818 | 13.2 | 56.3-106 |
| | V11 | 25 | 90.9 | | 12.6 | |
| Stems Per Plant (#) | Control | 24 | 2.6 | 0.4804 | 1.75 | 1-5.95 |
| | V11 | 25 | 2.8 | | 1.74 | |
| Plant Vigor (1-5 Scale)[3] | Control | 24 | 3.1 | 0.1856 | 1.04 | 1.33-4.00 |
| | V11 | 25 | 3.4 | | 0.978 | |
| Plant Height (cm) | Control | 24 | 56.7 | 0.3267 | 20.2 | 16.4-81.1 |
| | V11 | 25 | 59.1 | | 17.8 | |
| Vine Desiccation (%) | Control | 22 | 60.6 | 0.7981 | 36.1 | 0-99.8 |
| | V11 | 22 | 58.7 | | 32.6 | |

[1]Underlined P-values indicate statistically significant differences.
[2]The range of mean values of conventional varieties.
[3]Plant vigor was assessed on a 1 to 5 scale where 1 = severely less than the varietal average, 2 = noticeably less than varietal average, but not severe, 3 = plants are similar to the varietal average, 4 = slightly more than varietal average, 5 = obviously more than the varietal average, based on the principal investigator's professional experience which includes knowledge of potato growth and development for their specific geography.

TABLE 7

Tuber Characteristics

| Characteristic | Variety | N | Mean | P-Value[1] | Standard Deviation | Conventional Variety Range[2] |
|---|---|---|---|---|---|---|
| Total Yield (cwt/A) | Control | 21 | 314 | 0.2216 | 150 | 89.2-554 |
| | V11 | 22 | 342 | | 144 | |
| U.S.#1 Yield (cwt/a) | Control | 21 | 274 | 0.4144 | 153 | 62.7-522 |
| | V11 | 22 | 295 | | 143 | |
| Tubers Per Plant (#) | Control | 21 | 8.10 | 0.199 | 2.88 | 3.67-18.2 |
| | V11 | 22 | 9.02 | | 3.64 | |
| Size A Tubers (%) | Control | 21 | 75.3 | 0.981 | 8.40 | 28.0-83.3 |
| | V11 | 22 | 75.4 | | 7.98 | |
| Size B Tubers (%) | Control | 21 | 15.7 | 0.875 | 8.86 | 6.00-70.5 |
| | V11 | 22 | 15.0 | | 8.44 | |
| Oversize Tubers (%) | Control | 21 | 8.55 | 0.8095 | 9.52 | 0-23.8 |
| | V11 | 22 | 9.25 | | 9.99 | |
| Pickout Tubers (%) | Control | 21 | 0.474 | 0.9221 | 1.47 | 0-17.3 |
| | V11 | 22 | 0.294 | | 0.894 | |
| Specific Gravity | Control | 21 | 1.076 | 0.1008 | 0.0080 | 1.05-1.09 |
| | V11 | 22 | 1.078 | | 0.0064 | |
| Total Internal Defects (%) | Control | 21 | 24.9 | <u>0.0471</u> | 33.6 | 0-93.8 |
| | V11 | 22 | 18.7 | | 27.5 | |

[1]Underlined P-values indicate statistically significant differences.
[2]Range of mean values of conventional varieties.

Insect, Disease and Abiotic Stressor Assessments

Naturally occurring biotic (insect and disease) and abiotic stressors were observed and recorded by the principal investigators with expertise in potato cultivation. The stressor observations provided an opportunity to assess V11 across a broad range of stressors and locations at several points during the growing season and observe potential environmental interactions. Recorded stressors varied depending on which stressors were present or expected to be present. Even if no stressors were present, zeroes were recorded because the stressors were looked for and comparisons can be made between V11 and its parental control, Snowden.

Stressors were rated at early season, midseason, and late season on a 0 to 3 scale, where:
0=no symptoms observed; 1=slight symptoms were observed, but not interfering with plant development; 2=moderate symptoms were present, intermediate between slight and severe; 3=severe symptoms were observed that interfered with plant development.

The insect, disease, and abiotic stressor evaluations for V11 and the control are shown in Table 6. Stressor evaluations were intended to be categorical and were not statistically analyzed. The range of ratings for V11 and Snowden were compared for each observation, and a difference occurred when the range of V11 did not overlap with the range of Snowden. In total, no differences were observed for 148 out of 155 insect, disease, or abiotic stressors. The seven differences that were observed varied across sites and years.

One difference was noted between V11 and Snowden during 41 individual observations of seven abiotic stressors.

Three differences were observed between V11 and Snowden during 57 individual observations for 12 diseases.

Three differences were observed between V11 and Snowden during 57 individual observations for nine insects.

The small number of observed differences between V11 and Snowden and the lack of trends across sites supports a conclusion of no altered environmental interactions of V11 compared to its parental control, Snowden.

TABLE 8

Abiotic and Biotic Stressor Observations

| Stressor | Total Observations | Observations Without Differences | Observations With Differences | Differences[1] |
|---|---|---|---|---|
| *Abiotic Stressors* | | | | |
| Cold Stress | 2 | 2 | 0 | — |
| Compaction | 1 | 1 | 0 | — |
| Drought | 4 | 4 | 0 | — |
| Hail | 1 | 1 | 0 | — |
| Heat Stress | 14 | 14 | 0 | — |
| Water Stress | 12 | 12 | 0 | — |
| Wind Damage | 7 | 6 | 1 | Adams Co., WI 2012 Obs. 1: V11 = 0-1; Ctrl = 0-0; Ref = 0-1 |
| Total | 41 | 40 | 1 | — |
| *Disease Stressors* | | | | |
| Bacterial Wilt | 1 | 1 | 0 | — |
| Blackleg | 1 | 1 | 0 | — |
| *Botrytis* | 3 | 2 | 1 | Adams Co., WI 2012 Obs. 2: V11 = 0-1; Ctrl = 1-2; Ref = N/A |

TABLE 8-continued

Abiotic and Biotic Stressor Observations

| Stressor | Total Observations | Observations Without Differences | Observations With Differences | Differences[1] |
|---|---|---|---|---|
| Early Blight | 17 | 17 | 0 | — |
| Late Blight | 14 | 14 | 0 | — |
| Leaf Roll Virus | 2 | 1 | 1 | Adams Co., WI 2012 Obs. 2: V11 = 0-2; Ctrl = 1-2; Ref = 0-0 |
| Powdery Mildew | 1 | 1 | 0 | — |
| *Rhizoctonia* | 7 | 7 | 0 | — |
| *Sclerotinia* | 3 | 3 | 0 | — |
| Stem Rot | 1 | 1 | 0 | — |
| *Verticillium* Wilt | 2 | 1 | 1 | Grant Co., WA 2013 Obs. 3: V11 = 1-1; Ctrl = 0-0; Ref = 0-3 |
| White Mold | 5 | 5 | 0 | — |
| Total | 57 | 54 | 3 | — |

Insect Stressors

| Stressor | Total Observations | Observations Without Differences | Observations With Differences | Differences[1] |
|---|---|---|---|---|
| Aphid | 14 | 13 | 1 | Adams Co., WI 2012 Obs. 3: V11 = 1-2; Ctrl = 2-2; Ref = 0-0 |
| Armyworm | 1 | 1 | 0 | — |
| Colorado Potato Beetle | 18 | 16 | 2 | Adams Co., WI 2013 Obs. 1: V11 = 0-1; Ctrl = 0-0; Ref = 0-2 Montcalm Co., MI 2012 Obs. 2: V11 = 0-2; Ctrl = 0-0; Ref = 0-2 |
| Flea Beetle | 3 | 3 | 0 | — |
| Japanese Beetle | 1 | 1 | 0 | — |
| Leaf Beetle | 2 | 2 | 0 | — |
| Leaf Hopper | 14 | 14 | 0 | — |
| Looper | 3 | 3 | 0 | — |
| White Flies | 1 | 1 | 0 | — |
| Total | 57 | 54 | 3 | — |

[1]The range of values observed in conventional reference varieties (Ref).
N/A means a reference range was unavailable.
Obs. 1 = early season.
Obs. 2 = mid-season.
Obs. 3 = late season.

Results of these agronomic trials confirmed that V11 is phenotypically and agronomically similar to its parental control, Snowden, when grown at multiple locations representing the major areas for potato production in the U.S. Observations throughout the growing season demonstrated no meaningful differences in phenotypic and agronomic characteristics, tuber characteristics, biotic and abiotic stress susceptibility, and volunteer potential. No phenotypes that could indicate enhanced weediness, survivability, or plant pest potential were noted for V11.

Volunteer Potential

In an agricultural setting, volunteers are plants that grow from tubers dropped or left behind during planting, harvest, and other field operations, sometimes in a subsequent growing season. This volunteer potential study was intentionally planted with a known quantity of tubers to simulate tubers left behind after harvest. The objective was to evaluate the potential of V11 potatoes to overwinter and produce volunteer plants compared with its parental variety, Snowden.

The study was conducted at multiple sites to include a range of environmental conditions. Tubers of V11, Snowden, and conventional references were planted in the fall of 2012 at two sites (Table 9). The sites were monitored from planting until conditions were too cold for plant growth and again during the following spring when the soil warmed until approximately Jul. 15, 2013. Volunteer plants were counted, removed, and devitalized approximately every two weeks. This assessment compared the total number of volunteer plants for V11 and Snowden over the observation period and found no differences (Table 10).

TABLE 9

Volunteer Potential Field Trial Locations

| State | County | Variety | Trial Design[1] | Rows × Planted Tubers/Row[2] | Regional Specifics |
|---|---|---|---|---|---|
| ID | Canyon | V11 Snowden Ranger Russet Norkotah Shepody Atlantic Russet Burbank G and H (proprietary varieties) | RCB 4 reps | 3 × 10 | Typical for Southwest Idaho, which produces about 120 million cwt/year, mainly for the fry industry. Careful management is needed to limit or prevent heat-associated agronomic issues. |

TABLE 9-continued

Volunteer Potential Field Trial Locations

| State | County | Variety | Trial Design[1] | Rows × Planted Tubers/ Row[2] | Regional Specifics |
|---|---|---|---|---|---|
| WA | Grant | V11 Snowden Ranger Russet Norkotah Umatilla Pacific, Atlantic Russet Burbank G and H (proprietary varieties) | RCB 4 reps | 3 × 10 | Typical for Washington, which produces about 85 million cwt/year, mainly for the fry industry, with harvests in fall. Ideal growing conditions give rise to very high yields per acre. |

[1]RCB = Randomized Complete Block design. Number of blocks was equal to the number of reps.
[2]30 total tubers per rep.

TABLE 10

Mean Total Field Volunteers Observed For Each Variety

| Variety | N[1] | Mean Total Volunteers[2] | Standard Deviation | Conventional Variety Range |
|---|---|---|---|---|
| Atlantic[1] | 8 | 0.0 | 0.0 | 0.0-0.1 |
| Russet Burbank[1] | 8 | 0.0 | 0.0 | |
| Ranger Russet[1] | 8 | 0.1 | 0.2 | |
| V11[1] | 8 | 0.0 | 0.0 | |
| Snowden[1] | 8 | 0.0 | 0.0 | |

[1]N = number of sites (2) times the number of replications per site (4)
[2]Mean total volunteers = total number of volunteers counted during observation period divided by N Most varieties tested, including V11 and Snowden, produced no volunteer plants. Low numbers of volunteers were seen in some other varieties. These results indicate that winter conditions were harsh enough to devitalize almost all tubers at both sites. The few volunteers observed may be explained by random variations in seed size or planting depth. Larger tubers and deeper planting depth would both provide greater insulation during winter and increase the chance of volunteers being produced. While the study attempted to control both of these factors, some variation is to be expected. The study was designed to give tubers a better chance to produce volunteer plants than they would in a commercial cropping system. For example, both whole and cut tubers were planted and covered with soil. A tuber dropped during harvest and exposed to winter weather would almost certainly be devitalized by freezing in most major potato growing areas. The lack of volunteer plants in V11 and the Snowden control indicates there is likely no altered volunteer potential in V11. All available data and evidence supports that V11 has no pest potential and is not weedy.

Conclusions for Agronomic Performance and Field Observations

Results of these agronomic trials confirmed that V11 is phenotypically and agronomically similar to its parental control, Snowden, when grown at multiple locations representing the major areas for potato production in the U.S. Observations throughout the growing season demonstrated no meaningful differences in phenotypic and agronomic characteristics, tuber characteristics, biotic and abiotic stress susceptibility, and volunteer potential. No phenotypes that could indicate enhanced weediness, survivability, or plant pest potential were noted for V11.

Example 8. Potato Cultivar V11 Compositional Assessment

A compositional analysis of V11 was conducted to evaluate the levels of key nutrients (proximates, vitamins, amino acids, and minerals) and glycoalkaloids compared to the parental control, Snowden. In addition, concentrations of free amino acids, sugars, and acrylamide were evaluated in V11 and Snowden to measure efficacy of the low acrylamide potential and lowered reducing sugars traits.

Tubers for the compositional assessment were generated in the same field studies as described for the phenotypic testing (Example 7, Table 6). Briefly, tubers were collected from seven sites over two years with 3-4 replications per site. Samples were obtained by randomly selecting six mid-sized tubers (at harvest) from each site and rep. Samples (whole tubers, including skin) were powdered in an industrial blender with liquid nitrogen and stored at −70° C. until analysis. Analytical testing was conducted by Covance Laboratories, Inc.

Results of the composition studies demonstrate that V11 is comparable to conventional potatoes with respect to nutrient and glycoalkaloid composition. As expected, and similar to the previously deregulated events, the levels of reducing sugars (glucose and fructose), free asparagine, and acrylamide are lower in V11 than in Snowden.

Compositional Nutrient Analysis

These analyses were conducted to confirm that composition of V11 remained within the normal levels for potato and would have equivalent food quality, feed quality, and safety when compared to its parental control, Snowden, and conventional potatoes. The compositional assessments determined the concentrations of: 1) proximates, vitamins, and minerals (Table 11); 2) total amino acids (Table 12); 3) glycoalkaloids (Table 13).

TABLE 11

Proximates, Vitamins, and Minerals in V11 and Its Parental Control, Snowden

| Compound | Variety | Mean | P-value[1] | N | Standard Deviation | Range | | Tolerance Interval[2] | | Combined Literature Range[3] | |
|---|---|---|---|---|---|---|---|---|---|---|---|
| | | | | | | Min | Max | Min | Max | Min | Max |
| Moisture (%) | V11 | 78.5 | 0.1064 | 22 | 1.89 | 76 | 83 | 71.7 | 87 | 63.2 | 86.9 |
| | Control | 79.2 | | 21 | 1.83 | 76.3 | 83.2 | | | | |

TABLE 11-continued

Proximates, Vitamins, and Minerals in V11 and Its Parental Control, Snowden

| Compound | Variety | Mean | P-value[1] | N | Standard Deviation | Range Min | Range Max | Tolerance Interval[2] Min | Tolerance Interval[2] Max | Combined Literature Range[3] Min | Combined Literature Range[3] Max |
|---|---|---|---|---|---|---|---|---|---|---|---|
| Protein (%) | V11 | 2.34 | 0.9048 | 22 | 0.259 | 1.99 | 2.91 | 0.83 | 3.48 | 0.7 | 4.6 |
|  | Control | 2.33 |  | 21 | 0.24 | 2.01 | 2.82 |  |  |  |  |
| Fat (%) | V11 | 0.166 | 0.8899 | 22 | 0.053 | 0.1 | 0.3 | 0 | 0.5 | 0.02 | 0.2 |
|  | Control | 0.162 |  | 21 | 0.061 | 0.1 | 0.33 |  |  |  |  |
| Ash (%) | V11 | 1.03 | 0.6646 | 22 | 0.105 | 0.82 | 1.2 | 0.5 | 1.37 | 0.44 | 1.9 |
|  | Control | 1.01 |  | 21 | 0.107 | 0.803 | 1.2 |  |  |  |  |
| Crude Fiber (%) | V11 | 0.475 | 0.3731 | 22 | 0.086 | 0.34 | 0.63 | 0.197 | 0.83 | 0.17 | 3.5 |
|  | Control | 0.503 |  | 21 | 0.102 | 0.353 | 0.7 |  |  |  |  |
| Carbohydrates (%) | V11 | 17.9 | 0.1296 | 22 | 1.87 | 13.5 | 20.5 | 9.3 | 25.4 | 13.3 | 30.5 |
|  | Control | 17.3 |  | 21 | 1.81 | 13.4 | 20.4 |  |  |  |  |
| Total Calories (kcal/100 g) | V11 | 82.5 | 0.1161 | 22 | 7.70 | 64 | 93.2 | 48.8 | 111 | 80 | 110 |
|  | Control | 79.9 |  | 21 | 7.29 | 64.2 | 92.1 |  |  |  |  |
| Vitamin $B_3$ (Niacin) (mg/100 g) | V11 | 2.19 | 0.0984 | 22 | 0.259 | 1.62 | 2.64 | 0.794 | 2.68 | 0.09 | 3.1 |
|  | Control | 2.05 |  | 21 | 0.201 | 1.68 | 2.32 |  |  |  |  |
| Vitamin $B_6$ (mg/100 g) | V11 | 0.11 | 0.9855 | 22 | 0.011 | 0.097 | 0.14 | 0.064 | 0.19 | 0.11 | 0.34 |
|  | Control | 0.11 |  | 21 | 0.011 | 0.096 | 0.14 |  |  |  |  |
| Vitamin C (mg/100 g) | V11 | 26.9 | 0.005 | 22 | 2.45 | 22.1 | 32 | 12.1 | 34.4 | 1 | 54 |
|  | Control | 24.1 |  | 21 | 4.10 | 15.2 | 30.4 |  |  |  |  |
| Copper (mg/100 g) | V11 | 0.08 | 0.9679 | 22 | 0.023 | 0.05 | 0.12 | 0.011 | 0.16 | 0.02 | 0.7 |
|  | Control | 0.08 |  | 21 | 0.024 | 0.05 | 0.12 |  |  |  |  |
| Magnesium (mg/100 g) | V11 | 22.6 | 0.232 | 22 | 3.77 | 17.9 | 31 | 11.3 | 31 | 11.3 | 55 |
|  | Control | 21.8 |  | 21 | 3.51 | 17.4 | 29.4 |  |  |  |  |
| Potassium (mg/100 g) | V11 | 488 | 0.1021 | 22 | 43.0 | 426 | 605 | 240 | 587 | 350 | 625 |
|  | Control | 473 |  | 21 | 39.2 | 405 | 557 |  |  |  |  |

[1]P-values indicating significant differences with controls are bold and underlined.
[2]TI = 99% Tolerance Interval, 95% confidence.
[3]Literature ranges are from Lisinska and Leszczynski (1989), Rogan et al., (2000), Horton and Anderson (1992), Talburt and Smith (1987).

TABLE 12

Total Amino Acids in V11 and Its Parental Control, Snowden

| Compound | Variety | Mean | P-value[1] | N | Standard Deviation | Range Min | Range Max | Tolerance Interval[2] Min | Tolerance Interval[2] Max | Combined Literature Range[3] Min | Combined Literature Range[3] Max |
|---|---|---|---|---|---|---|---|---|---|---|---|
| Alanine (mg/100 g) | V11 | 70.9 | 0.0067 | 22 | 5.62 | 60.4 | 82.9 | 22.4 | 105 | 39.2 | 95.2 |
|  | Control | 64.2 |  | 21 | 4.99 | 56.7 | 76.1 |  |  |  |  |
| Arginine (mg/100 g) | V11 | 142 | 0.0056 | 22 | 29.4 | 109 | 204 | 15.8 | 188 | 70.0 | 138 |
|  | Control | 123 |  | 21 | 21.6 | 89.4 | 169 |  |  |  |  |
| Aspartic Acid (mg/100 g) | V11 | 300 | <.0001 | 22 | 35.0 | 249 | 377 | 44.2 | 799 | 339 | 738 |
|  | Control | 519 |  | 21 | 62.9 | 414 | 627 |  |  |  |  |
| Glutamic Acid (mg/100 g) | V11 | 495 | <.0001 | 22 | 79.3 | 327 | 653 | 128 | 581 | 292 | 604 |
|  | Control | 350 |  | 21 | 44.4 | 283 | 428 |  |  |  |  |
| Glycine (mg/100 g) | V11 | 72.7 | 0.0103 | 22 | 7.89 | 59.3 | 89.3 | 8.60 | 110 | 1 | 97.5 |
|  | Control | 65.4 |  | 21 | 6.67 | 56.8 | 81.7 |  |  |  |  |
| Histidine (mg/100 g) | V11 | 36.0 | 0.1944 | 22 | 5.74 | 30.1 | 49.1 | 11.5 | 52.5 | 13.3 | 46.9 |
|  | Control | 34.3 |  | 21 | 5.14 | 27.5 | 45.7 |  |  |  |  |
| Isoleucine (mg/100 g) | V11 | 82.2 | 0.0085 | 22 | 9.05 | 67.7 | 101 | 20.0 | 123 | 52.5 | 95.3 |
|  | Control | 75.5 |  | 21 | 8.37 | 63.8 | 94.5 |  |  |  |  |
| Leucine (mg/100 g) | V11 | 138 | 0.0026 | 22 | 13.0 | 114 | 167 | 3.60 | 225 | 68.5 | 138 |
|  | Control | 124 |  | 21 | 11.5 | 109 | 153 |  |  |  |  |
| Lysine (mg/100 g) | V11 | 118 | 0.0534 | 22 | 11.4 | 99.8 | 143 | 36.6 | 173 | 68.7 | 137 |
|  | Control | 111 |  | 21 | 8.76 | 102 | 132 |  |  |  |  |
| Methionine (mg/100 g) | V11 | 39.2 | 0.1648 | 22 | 4.03 | 31.8 | 46.6 | 11.3 | 59.7 | 9 | 128 |
|  | Control | 36.9 |  | 21 | 3.52 | 30.2 | 42.9 |  |  |  |  |
| Phenylalanine (mg/100 g) | V11 | 96.6 | 0.0638 | 22 | 10.7 | 75.9 | 121 | 11.7 | 154 | 55.2 | 109 |
|  | Control | 91.2 |  | 21 | 9.73 | 76.6 | 114 |  |  |  |  |
| Proline (mg/100 g) | V11 | 78.9 | 0.3559 | 22 | 16.1 | 55.8 | 111 | 0 | 155 | 35.5 | 146 |
|  | Control | 72.3 |  | 21 | 13.7 | 51.9 | 95.3 |  |  |  |  |
| Serine (mg/100 g) | V11 | 82.7 | 0.0049 | 22 | 10.2 | 63.2 | 103 | 10 | 130 | 50.0 | 102 |
|  | Control | 74.7 |  | 21 | 7.30 | 62.0 | 90.9 |  |  |  |  |
| Threonine (mg/100 g) | V11 | 85.6 | 0.0027 | 22 | 8.91 | 70.3 | 105 | 11.5 | 129 | 43.6 | 85.5 |
|  | Control | 77.7 |  | 21 | 7.53 | 68.6 | 97.1 |  |  |  |  |

TABLE 12-continued

Total Amino Acids in V11 and Its Parental Control, Snowden

| Compound | Variety | Mean | P-value[1] | N | Standard Deviation | Range Min | Range Max | Tolerance Interval[2] Min | Tolerance Interval[2] Max | Combined Literature Range[3] Min | Combined Literature Range[3] Max |
|---|---|---|---|---|---|---|---|---|---|---|---|
| Tryptophan (mg/100 g) | V11 | 20.9 | 0.2731 | 22 | 4.66 | 13.9 | 32.2 | 7.20 | 36.3 | 11.4 | 28.2 |
| | Control | 20.1 | | 21 | 4.47 | 11.5 | 27.6 | | | | |
| Tyrosine (mg/100 g) | V11 | 85.9 | 0.0020 | 22 | 10.2 | 72.0 | 108 | 17.3 | 124 | 45.7 | 94.2 |
| | Control | 76.1 | | 21 | 8.83 | 66.1 | 94.3 | | | | |
| Valine (mg/100 g) | V11 | 109 | 0.0225 | 22 | 13.0 | 90.0 | 133 | 43.3 | 159 | 75.2 | 145 |
| | Control | 102 | | 21 | 12.2 | 82.6 | 123 | | | | |

[1]P-values indicating significant differences with controls are bold and underlined.
[2]99% Tolerance Interval, 95% confidence.
[3]Literature ranges are from Talley et al., (1984), Rogan et al., (2000).

No statistical differences were found between V11 and Snowden for most of the proximates, vitamins and minerals measured (Table 11). Vitamin C content of V11 was greater than its parental control, Snowden, but was within the tolerance interval and literature range.

A significant difference between V11 and its parental control, Snowden, was noted for several total amino acids (Table 12): alanine, arginine, aspartic acid, glutamic acid, glycine, isoleucine, leucine, serine, threonine, tyrosine, and valine. Aspartic acid was expected to be lower and glutamic acid was expected to be higher in V11 than in Snowden because of the down-regulation of the Asn gene (FIG. 1). In each case, the mean for V11 was within the tolerance interval and/or the combined literature range, so V11 was considered equivalent to conventional potatoes.

Glycoalkaloids

Glycoalkaloids are toxins commonly found in Solanaceous crops, including potato. 95% of the total glycoalkaloids in potato tubers consists of α-solanine and α-chaconine (OECD, 2002). Today, the widely accepted safety limit for total glycoalkaloids in tubers is 20 mg/100 gm fresh weight (Smith et al., 1996).

The mean concentration of glycoalkaloids in V11 was not statistically different from its parent control, Snowden, and was within the generally accepted safety limit.

TABLE 13

Glycoalkaloids in V11 and Its Parental Control, Snowden

| Compound | Variety | Mean | P-value[1] | N | Standard Deviation | Range Min | Range Max | Tolerance Interval[3] Min | Tolerance Interval[3] Max |
|---|---|---|---|---|---|---|---|---|---|
| Glycoalkaloids[2] (mg/100 g) | V11 | 9.70 | 0.3878 | 22 | 4.10 | 5.00 | 19.4 | 0 | 20.4 |
| | Control | 10.8 | | 21 | 7.21 | 5.04 | 38.9 | | |

[1]P-values indicating significant differences with controls are bold and underlined.
[2]Total of α-solanine and α-chaconine
[3]99% Tolerance Interval, 95% confidence Traits Affecting Composition An assessment of trait efficacy of V11 for low acrylamide potential and lowered reducing sugars consisted of the following analyses: 1) free amino acids (Table 14); 2) reducing sugars (Table 15); 3) acrylamide (Table 16).

Free amino acid analysis demonstrated that, as expected, down-regulation of Asn1 was effective in reducing free asparagine in tubers. The results show that V11 tubers contained statistically less free asparagine and statistically more free glutamine than Snowden tubers (Table 14). However, the mean concentrations of free asparagine and free glutamine for V11 were still within the tolerance intervals and therefore considered within the normal range for potatoes.

TABLE 14

Free Amino Acids in Tubers at Harvest

| Compound | Variety | Mean | P-value[1] | N | Standard Deviation | Range Min | Range Max | Tolerance Interval[2] Min | Tolerance Interval[2] Max |
|---|---|---|---|---|---|---|---|---|---|
| Asparagine (mg/100 g) | V11 | 79.4 | <.0001 | 22 | 21.6 | 35.5 | 128 | 0 | 520 |
| | Control | 312 | | 21 | 51.4 | 212 | 407 | | |

TABLE 14-continued

Free Amino Acids in Tubers at Harvest

| Compound | Variety | Mean | P-value[1] | N | Standard Deviation | Range Min | Range Max | Tolerance Interval[2] Min | Tolerance Interval[2] Max |
|---|---|---|---|---|---|---|---|---|---|
| Aspartic Acid (mg/100 g) | V11 | 53.7 | 0.3054 | 22 | 35.0 | 33.8 | 77.8 | 4.20 | 71.4 |
|  | Control | 51.5 |  | 21 | 62.9 | 35.8 | 74.0 |  |  |
| Glutamine (mg/100 g) | V11 | 222 | <.0001 | 22 | 62.2 | 71.2 | 322 | 0 | 298 |
|  | Control | 125 |  | 21 | 36.0 | 55.9 | 181 |  |  |
| Glutamic Acid (mg/100 g) | V11 | 66.5 | 0.2872 | 22 | 13.5 | 37.9 | 90.2 | 4.40 | 96.4 |
|  | Control | 61.8 |  | 21 | 11.5 | 41.9 | 78.4 |  |  |

[1]P-values indicating significant differences between V11 and control are in bold and underlined.
[2]99% Tolerance Interval, 95% confidence.

A review of the biosynthetic pathway for asparagine and glutamine in FIG. 1 illustrates how a reduction in asparagine could lead to increases in glutamine. Through the activity of ASN1, the side-chain amine from glutamine is transferred to aspartate to form asparagine and glutamate. Down-regulation of Asn1 would favor increased glutamine and reduced asparagine levels. Because of the down-regulation of the Asn1 gene in V11, increased free glutamine and reduced asparagine were expected.

The V11 event contains expression cassettes designed to lower levels of reducing sugars fructose and glucose in tubers. A down-regulation cassette for the promoters of the starch-associated gene (R1) and the phosphorylase-L gene (PhL) was introduced in V11. These traits should function by slowing the conversion of starch to the reducing sugars glucose and fructose. In V11, partial down-regulation of R1 and PhL resulted in slightly lower levels of reducing sugars at 0 (fresh) and 3 months after harvest, though the results were not statistically significant (Table 15). After nine months of storage, reducing sugars increased in both the V11 and its parental control. There were no differences in sucrose between V11 and its control.

TABLE 15

Tuber Sugars at Harvest and Stored at 50° F.

| Timing | Variety | Mean | P-value[1] | N | Range Min | Range Max | Tolerance Interval[2] Min | Tolerance Interval[2] Max |
|---|---|---|---|---|---|---|---|---|
| Fructose + Glucose (mg/100 g) | | | | | | | | |
| Fresh | V11 | 26.7 | 0.7689 | 22 | 5.50 | 108 | 1 | 435 |
|  | Control | 35.1 |  | 21 | 5.20 | 145 |  |  |
| Month 3 | V11 | 53.5 | 0.2127 | 6 | 11.5 | 204 | 1 | 435 |
|  | Control | 151 |  | 5 | 26.7 | 319 |  |  |
| Month 6 | V11 | 39.4 | 0.945 | 3 | 11.5 | 95.0 | 1 | 435 |
|  | Control | 14.7 |  | 3 | 11.1 | 19.1 |  |  |
| Month 9 | V11 | 92.3 | 0.997 | 3 | 80.9 | 99.1 | 1 | 435 |
|  | Control | 105 |  | 3 | 84.2 | 125 |  |  |

TABLE 15-continued

Tuber Sugars at Harvest and Stored at 50° F.

| Timing | Variety | Mean | P-value[1] | N | Range Min | Range Max | Tolerance Interval[2] Min | Tolerance Interval[2] Max |
|---|---|---|---|---|---|---|---|---|
| Sucrose (mg/100 g) | | | | | | | | |
| Fresh | V11 | 197 | 0.8569 | 22 | 114 | 424 | 1 | 443 |
|  | Control | 194 |  | 21 | 116 | 432 |  |  |
| Month 3 | V11 | 147 | 0.4911 | 6 | 131 | 170 | 1 | 443 |
|  | Control | 179 |  | 5 | 127 | 262 |  |  |
| Month 6 | V11 | 98.0 | 0.7371 | 3 | 55.0 | 169 | 1 | 443 |
|  | Control | 74.2 |  | 3 | 62.4 | 82.1 |  |  |
| Month 9 | V11 | 171 | 0.9867 | 3 | 146 | 209 | 1 | 443 |
|  | Control | 145 |  | 3 | 143 | 148 |  |  |

[1]P-values indicating significant differences between V11 and control are in bold and underlined.
[2]99% Tolerance Interval, 95% confidence.

Lowered asparagine, fructose and glucose levels led to an overall reduction of acrylamide in processed potato products because they are reactants in the formation of acrylamide. In order to demonstrate the lower potential acrylamide trait, field-grown tubers of V11 and Snowden at harvest and after 3, 6, and 9 months of storage at 50° F. were made into chips, and the acrylamide concentration of the chips was measured (Table 16).

At the time of harvest, potato chips made with V11 tubers contained 64.3% less acrylamide than chips made with Snowden (Table 16). When potatoes were stored throughout 3 months at 50° F., acrylamide concentrations in V11 were 48.9% lower than the control. Acrylamide concentrations in V11 chips were numerically but not statistically lower than Snowden after tuber storage at 50° F. for 6 and 9 months. The significantly lower acrylamide levels at 0 and 3 months after storage were expected from down-regulation of the Asn1, R1 and PhL genes, thus reducing the reactants free asparagine and reducing sugars. Similar reductions in reducing sugars and acrylamide were reported by Zhu et al., 2014.

Snowden is recommended for 3 to 6 months storage (USPB 2014, UNL Crop Watch 2015), so lower acrylamide potential in tubers stored for up to 6 months after harvest will provide value throughout the typical storage time.

TABLE 16

Acrylamide in Chips Made From Potatoes at Harvest and After Storage at 50° F.

| Timing | Compound | Variety | Mean | P-value[1] | Percent Reduction | N | Range Min | Range Max | Tolerance Interval[2] Min | Tolerance Interval[2] Max |
|---|---|---|---|---|---|---|---|---|---|---|
| Fresh | Acrylamide (ppb) | V11 | 262 | <.0001 | 64.3 | 22 | 112 | 540 | 10 | 1,185 |
|  |  | Control | 734 |  |  | 21 | 239 | 1540 |  |  |

TABLE 16-continued

Acrylamide in Chips Made From Potatoes at Harvest and After Storage at 50° F.

| Timing | Compound | Variety | Mean | P-value[1] | Percent Reduction | N | Range Min | Range Max | Tolerance Interval[2] Min | Tolerance Interval[2] Max |
|---|---|---|---|---|---|---|---|---|---|---|
| Month 3 | Acrylamide (ppb) | V11 | 289 | 0.0066 | 48.9 | 6 | 125 | 582 | 10 | 1,185 |
| | | Control | 566 | | | 5 | 399 | 857 | | |
| Month 6 | Acrylamide (ppb) | V11 | 306 | 0.6386 | 47.9 | 3 | 279 | 335 | 10 | 1,185 |
| | | Control | 587 | | | 3 | 337 | 717 | | |
| Month 9 | Acrylamide (ppb) | V11 | 708 | 0.9839 | 15.6 | 3 | 499 | 1080 | 10 | 1,185 |
| | | Control | 839 | | | 3 | 530 | 1030 | | |

[1]P-values indicating significant differences between V11 and control are in bold and underlined.
[2]99% Tolerance Interval, 95% confidence.

A thorough compositional assessment was conducted on V11 and its parental control, Snowden. Two types of analyses were conducted: 1) compositional nutritional assessment, for those analytes important to general potato nutrition; and 2) traits affecting composition, for those specific analytes related to gene down-regulation and trait efficacy.

The nutritional assessment, evaluating proximates, vitamins, minerals, amino acids, and glycoalkaloids demonstrated that V11 is compositionally equivalent to Snowden and is as safe and nutritious for food and feed as conventional potatoes that have a long history of safe consumption.

The efficacy assessment, evaluating free amino acids and reducing sugars as well as acrylamide concentrations in chips demonstrated that, like the previously deregulated events, V11 has lower levels of free asparagine, lower levels of reducing sugars, and lower acrylamide potential in potato chips than Snowden.

Example 9. Environmental Safety Assessment

The environmental safety of V11 is supported by extensive testing including phenotypic performance, trait efficacy, genetic characterization, and compositional assessment. Information on V11 has been reviewed to determine the potential risk to the environment using the following five criteria: 1) Potential to become a weed of agriculture or to be invasive of natural habitats; 2) Potential for gene flow to sexually compatible plants; 3) Potential to become a plant pest; 4) Potential impact on non-target species including humans; and 5) Potential impact on biodiversity.

Potential to Become Weedy, Invasive, or a Plant Pest

Weediness is a term used to describe the ability of a plant to become a weed (survive and thrive) outside of cultivation. Multiple field trials with V11 did not provide any evidence for altered growth characteristics such as accelerated tuber sprouting, increased plant vigor, increased tuber set, delayed senescence, volunteer potential, or other key phenotypic characteristics associated with weediness, invasiveness, or survival outside of cultivation.

Potato is a poor competitor and does not thrive in a non-cultivated environment (Love 1994). Due to modern agricultural practices it is unlikely that potatoes would persist in a field from one crop cycle to the next, particularly since potatoes are typically grown as a rotational crop. Also, much like Canada, in the northern U.S. most of the production areas experience deep frost penetration in the soil, minimizing the likelihood of over-winter survival (CFIA 1996). Results of the phenotypic assessment demonstrate no differences between V11 and its parental control with respect to survivability, and thus it is unlikely that V11 possesses increased potential to become a weed of agriculture, be invasive of natural habitats, or be a plant pest.

Potential for Gene Flow to Sexually Compatible Plants

Gene flow from V11 is expected to be minimal due to agricultural practices and biological characteristics of the Snowden variety.

Generally, the potential for gene transfer in any potatoes through outcrossing within the species is minimal for several reasons: a high percentage of fertile potatoes are self-pollinated and are not frequented by honeybees due to a lack of nectar; pollen transfer between plants is limited to about 20 meters (Conner and Dale 1996) making transfer between commercial-scale fields unlikely; it is unlikely that true potato seeds produced through outcrossing would grow into mature potatoes since potato seeds are not saved and propagated in a typical farming operation; and potatoes are almost always clonally propagated using seed potatoes, thus removing the potential for further propagation of seed produced through outcrossing.

In the unlikely event that outcrossing was to occur between V11 and other potatoes, the impact would be negligible because tubers and not true potato seeds are harvested for future plantings. If seedlings did arise from an outcrossing event, establishment would be nearly impossible since potatoes are grown in rotation and are poor competitors compared to other crop and weed species (Love 1994; CFIA 1996). If seedlings were to establish after harvest, they would be easily identified and eliminated as part of the standard agricultural practices in potato production. In either case, seedlings could be identified and eliminated to prevent them from entering the commercial stream.

Potential Impact on Non-Target Species and Biodiversity

V11 has no impact on non-target organisms. V11 does not express any traits with pesticidal activity; thus interactions with other species in the environment are, by definition, non-target. Observational data and field studies noted in the phenotypic assessment support the conclusion that no adverse impacts to non-targets occurred and no evidence of altered plant-disease interactions were noted. The mechanism of action for the reduced black spot and lower reducing sugar traits is down-regulation of endogenous potato genes. No novel proteins are produced. In addition, V11 is compositionally equivalent to conventional potatoes. Therefore, V11 does not possess any mechanism to harm non-target organisms or biodiversity and does not pose any risk to threatened or endangered species or humans when compared to commercially grown conventional potato varieties.

Example 10. Molecular Methods

Genetic Characterization

The following methods were used to generate the molecular data for V11. Methods are included for characterization of the pSIM1278 insertion, including insert structures, absence of vector backbone, identification of flanking regions, and genetic stability.

Characterization of Insert Structures

Plant Material. Snowden plants used for characterization of insert DNA were grown in Sunshine mix-1 (www.sungro.com) in two-gallon pots in a greenhouse that was controlled for temperature (18° C. minimum/27° C. maximum) and light (16-h photoperiod with an intensity of ~1500 μmol/m2/s). Snowden control plants were also grown in the greenhouse under the same conditions and used as a background control. After one to two months of growth, leaf materials were taken from V11 and Snowden control plants for genomic DNA isolation.

DNA Isolation. DNA was isolated from leaf material using a modified CTAB protocol. Briefly, 1 g leaf tissue was ground under liquid nitrogen then suspended in extraction buffer containing 50 mM EDTA, 0.1 M Tris-HCl, pH 8.0, and 0.35 M Sorbitol. Tissue was pelleted by centrifugation, rinsed with extraction buffer, and resuspended in 2 ml extraction buffer with 100 μg/mL RNase A. An equal volume of lysis buffer containing 0.2 M Tris-HCl, pH 8.0, 50 mM EDTA, 2M NaCl, 2% CTAB, and 0.8 ml 5% Sarkosyl was added and incubated 20 min. at 65° C. DNA was extracted with two rounds of 24:1 chloroform: isoamyl alcohol followed by precipitation in Isopropanol, centrifugation, and a single wash with 70% Ethanol. Purified genomic DNA was resuspended in TE, pH 8.0 and quantified using a Qubit 2.0 Fluorometer (Molecular Probes) with the dsDNA Broad Range Assay kit (Molecular Probes).

DNA Gel (Southern) Blot Analysis. 3 μg of plant DNA was digested overnight in 400 μl final volume with at least 5 μl (10 units/μl) restriction enzyme (Invitrogen) at 37° C. Digested DNA was concentrated by ethanol precipitation (40 μl of 3 M NaOAc, pH5.3 and 1 ml ethanol) at −20° C. for 30 min followed by a wash with 70% ethanol. The DNA pellet was dissolved in 20 μl 1×TE followed by addition of 5 μl DNA gel loading buffer, which consists of 40% sucrose and 0.35% Orange G (Sigma) in water.

Membrane Preparation. Digested plant DNA was loaded on a large 0.7% agarose gel (170 ml) containing 0.5× tris-borate-EDTA (TBE) buffer and 3-5 μl ethidium bromide (10 mg/ml) and run at 30 volts for 18 hrs. The gel was photographed using a gel documentation system from Alpha Innotech (Santa Clara, Calif.), and then depurinated by submerging it into 0.25 N HCl for 20 min. After subsequent denaturation in 0.5 M NaOH/1.5 M NaCl for 2×15 min and neutralization in 1.5 M NaCl and 0.5 M Tris-HCl, pH7.5, for 2×15 min on a shaker at room temperature the gel was equilibrated with 10×SSC for 10 min. The transfer of DNA to the nylon membrane was carried out using 10×SSC according to a standard capillary transfer method.

Figure 22:
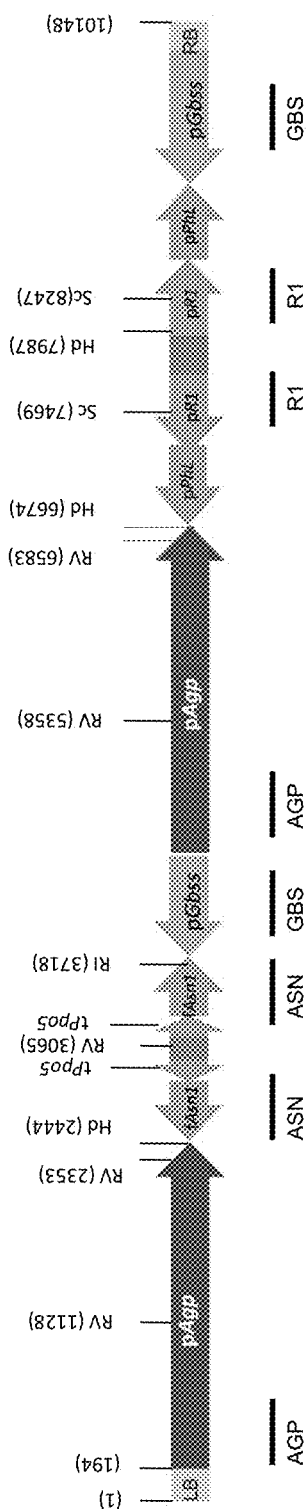
FIG. 22 shows the positions of probes in the DNA insert. RV=EcoRV, R1=EcoRI, Sc=ScaI, Hd=HindIII, LB=Left Border like region containing 25-bp Left Border and 162-bp flanking sequence. RB=Right Border like region containing 25-bp Right Border and 161-bp flanking sequence.

Probe Preparation. The labeling of the PCR-derived probe was achieved using Hotmaster Taq enzyme and buffer (Fisher BioReagents) according to Roche's DIG labeling instructions. A standard 50 μl reaction consisted of 5 μl of 10× Hotmaster Taq Buffer, 2-5 μl of 10 uM forward primer, 2-5 μl of 10 μM reverse primer, 5 μl DIG-labeled dNTP (Roche), 10 ng construct template, 0.75 μl Hotmaster Taq polymerase, and water. The PCR amplification conditions were dependent on each DIG-labeled probe. PCR with regular dNTP instead of DIG labeled dNTP was used as control. Quality of the DIG-labeled probe was assessed by running a small amount of the probe on 1% agarose DNA gel (it always ran slower than control PCR product). The probe was denatured before use by incubating the probe at 100° C. for 5 min, placing on ice for 2 min. For the exact position of probes in the DNA insert, see FIG. 22.

Hybridization. The nylon membrane carrying transferred DNA was prehybridized in 40 ml pre-warmed DIG Easy Hybridization solution (Roche) at 42° C. for 1-4 hours in a bottle in a standard hybridization oven (Amerex Instruments Inc.) at 20-25 rpm. Hybridization was carried out by replacing the prehybridization buffer with a fresh amount of the same preheated solution, now containing 25-50 μl denatured DIG labeled probe, and continuing the incubation at 42° C., 20-25 rpm for about 16 hrs. The hybridization solution could be store at −20° C. and reused up to 3 times. The reused hybridization solution was heated at 68° C. for 10 minutes before use.

Detection. The hybridization solution was removed and replaced by 100 ml washing solution I (2×SSC/0.1% SDS). The membrane was washed twice in washing solution I for 10 min at room temperature. This low stringency buffer was poured off and preheated high stringency washing solution II (0.5×SSC/0.1% SDS, 65° C.) was added immediately. The membrane was washed twice in washing solution II at 65° C. for 20 min each at 25-30 rpm. This was followed by a brief rinse with 2×SSC to remove SDS. The membrane was rinsed with 150 ml of 1×DIG Washing Solution (Roche) in a tray for 2 min and incubated in 1× Blocking solution (Roche) for 0.5-3 hrs on a low-speed shaker. The blocked membrane was incubated with DIG antibody solution (1:10, 000 dilution of Anti-DIG-alkaline phosphate conjugate with 1× Blocking solution) for 30 min on a shaker. The membrane was washed twice (15 min each) with 1×DIG Washing Solution (Roche) and equilibrated with 1× detection buffer. The detection reaction was carried out with 2 ml CDP-Star solution (1:100 diluted stock of CDP-Star with 1× detection buffer) for 5 min. The membrane was wrapped in a plastic film and exposed to the Z-ray film in the dark. Depending on the experiment, multiple exposures were taken from 30 sec to 30 min. The films were developed with Konica SRX-101A Z-ray film developer. The developed films were scanned to obtain the final images.

Characterization of Vector Backbone Sequences

Plant material. Plants used for DNA gel blot analysis were grown for two months in Sunshine mix-1 (www.sungro.com) in two-gallon pots in a greenhouse controlled for temperature (18° C. minimum/27° C. maximum) and light (16-h photoperiod with an intensity of ~1500 μmol/m2/s).

DNA Isolation. Genomic DNA was isolated from the leaves of greenhouse-grown plants as described above for use in the following assays.

Southern Blot—Gel Preparation. Digested DNA was electrophoresed on a large 0.7% agarose gel (170 ml) containing 0.5× Tris-borate-EDTA (TBE) buffer and 3-5 μl ethidium bromide (10 mg/ml) for 18 hrs using 30 volts. The gel was photographed using a gel documentation system from Alpha Innotech (Santa Clara, Calif.), and then depurinated by submersion in 0.25N HCl for 20 min. After subsequent denaturation in 0.5 M NaOH/1.5 M NaCl for 2×15 min and neutralization in 1.5 M NaCl/0.5 M Tris-HCl (pH 7.5), for 2×15 min on a shaker at room temperature, the gel was equilibrated with 10×SSC for 10 min. The transfer of DNA to the nylon membrane was carried out using 10×SSC using capillary transfer.

Southern Blot—Probe Preparation. Nylon filters cross-linked with DNA digested with EcoRI were hybridized independently with eight different probes, which covered entire vector backbone (see Table 17 for primer sequences and FIG. 15 for the linear arrangements of the probes described in Table 17). Untransformed potato varieties were used as negative controls, and the T130 event carrying the entire backbone of pSIM1278 vector provided positive controls.

TABLE 17

Backbone Probes for pSIM1278

| Backbone probe | Size (bp) | pSIM1278 Coordinates | Forward Primer (5' to 3') | Reverse Primer (5' to 3') |
|---|---|---|---|---|
| BB1 | 1,474 | 10,149-11,622 | ACTAGTTGTGAATAAGTCGCTGTG (SEQ ID NO: 1) | TATCGGAATCGACTAACAGAACAT (SEQ ID NO: 2) |
| BB2 | 1,515 | 11,591-13,105 | CCGGGGCCGATGTTCTGUAG (SEQ ID NO: 3) | GCTCGCCGGCAGAACTTGAG (SEQ ID NO: 4) |
| BB3 | 1,588 | 13,054-14,641 | GCCGCGTGTTCCGTCCACAC (SEQ ID NO: 5) | CCTGTCGGGTTTCGCCACCT (SEQ ID NO: 6) |
| BB4 | 1,660 | 14,614-16,273 | CAAGTCAGAGGTGGCGAAAC (SEQ ID NO: 7) | CTTTATGCTCATTGGGTTGAGTA (SEQ ID NO: 8) |
| BB5 | 1,074 | 16,590-17,663 | AGTCCACCCGAAATATAAACAAC (SEQ ID NO: 9) | GGTATGGACCTGCATCTAATTTTC (SEQ ID NO: 10) |
| BB6 | 832 | 18,827-19,658 | GCTCTAATATAGCGCATTTCAAG (SEQ ID NO: 11) | GCTTCCAGCCAGCCAACAGCTC (SEQ ID NO: 12) |
| BB7 | 355 | 16,232-16,586 | CTATTTTTTTACTATATTATACTCAAC (SEQ ID NO: 13) | TTTTAATGTTTAGCAAATGTCTTATC (SEQ ID NO: 14) |
| BB8 | 1,179 | 17,668-18,846 | GATCCACCTCCACGTAGACGGAG (SEQ ID NO: 15) | GAAATGCGCTATATTAGAGCATA (SEQ ID NO: 16) |

The labeling of PCR-derived probes were achieved using Hotmaster Taq enzyme and buffer (Fisher BioReagents) according to Roche's DIG labeling protocol. A standard 50 μl reaction consisted of 5 μl of 10× Hotmaster Taq Buffer, 2-5 μl of 10 μM forward primer, 2-5 μl of 10 μM reverse primer, 5 μl of DIG labeled dNTPs (Roche), 10 ng construct template, 0.75 μl Hotmaster Taq polymerase, and water. The PCR amplification conditions were optimized for each DIG-labeled probe. PCR with regular dNTPs instead of DIG labeled dNTPs was used as positive control. Quality of the DIG labeled probe was assessed by analyzing a fraction of the product on a 1% agarose gel alongside control (unlabeled) PCR product. The probe was denatured before use by incubating the probe at 100° C. for 5 min, and then quenched on ice for 2 min.

Southern Blot—Hybridization and Exposure. The nylon membrane carrying transferred DNA was prehybridized in 40 ml pre-warmed DIG Easy Hybridization solution (Roche) at 42° C. for 1-4 hrs in a hybridization oven (Amerex Instruments Inc.) rotating at 20-25 rpm. Hybridization was carried out by replacing the prehybridization buffer with a fresh amount of the same preheated solution containing 25-50 μl denatured DIG labeled probe, and continuing the incubation with rotation (20-25 rpm) at 42° C. for about 16 hrs. The probe-containing hybridization solution was stored (−20° C.) and reused up to 3 times. The reused hybridization solution was heated at 68° C. for 10 minutes before use. The hybridization solution was removed and replaced by 100 ml washing solution I (2×SSC/0.1% SDS). The membrane was washed twice in washing solution I for 10 min at room temperature. This low stringency buffer was poured off and preheated high stringency washing solution II (0.5×SSC/0.1% SDS, 65° C.) was added immediately. The membrane was washed twice in washing solution II at 65° C. for 20 min each at 25-30 rpm. This was followed by a rinse with 2×SSC to remove SDS. The membrane was rinsed with 150 ml of 1×DIG Washing Solution (Roche) in a tray for 2 min and incubated in 1× Blocking solution (Roche) for 0.5-3 hours on a low-speed shaker. The blocked membrane was incubated with DIG antibody solution (1:10,000 dilution of Anti-DIG-alkaline phosphate conjugate with 1× Blocking solution) for 30 min on a shaker. The membrane was washed twice (15 min each) with 1×DIG Washing Solution (Roche) and equilibrated with 1× detection buffer. The detection reaction was carried out with 2 ml CDP-Star solution (1:100 diluted stock of CDP-Star with 1× detection buffer) for 5 min. The membrane was wrapped in plastic film and exposed to the Z-ray film in the dark. Depending on the experiment multiple exposures were taken from 30 sec to 30 min. Films were developed with a Konica SRX-101A Z-ray film developer. The developed films were scanned to obtain the final images.

Figure 23:
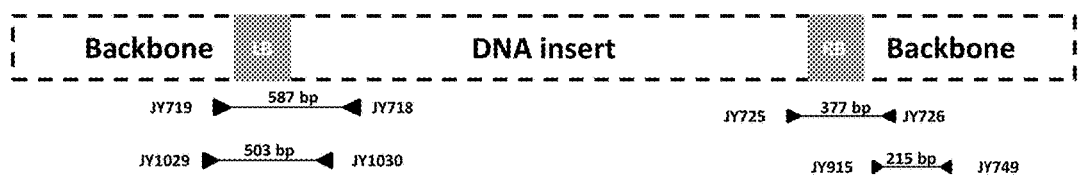
FIG. 23 shows PCR primers for detecting backbone adjacent to left and right borders of pSIM1278.
Figure 24:
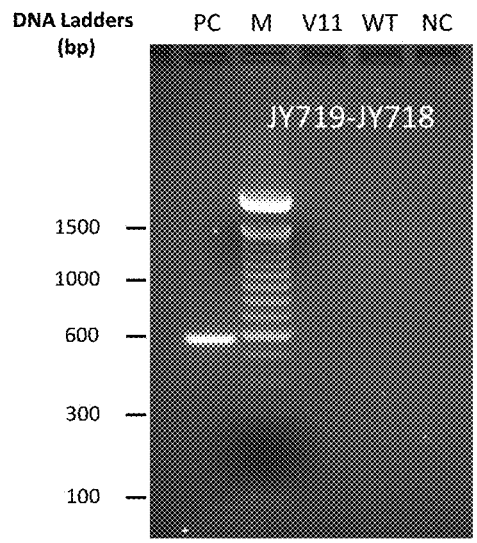
FIG. 24 shows confirmation of the absence of backbone DNA junctions. Top panels show detection of left border of the DNA insert and flanking backbone of pSIM1278. Bottom panels show detection of right border of the DNA insert and flanking backbone of pSIM1278. Ethidium bromide stained agarose gels for the PCR reactions using the primer sets indicated. PC=positive control plasmid, M=100-bp DNA marker (Invitrogen), V11=Snowden event V11, WT=Snowden wild type control, NC=Negative control.
Figure 24:
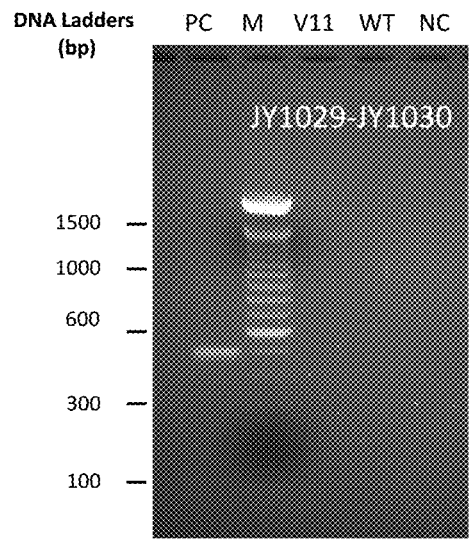
Figure 24:
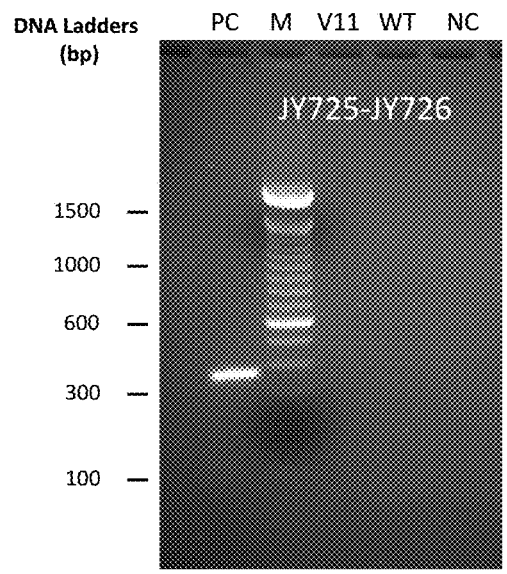
Figure 24:
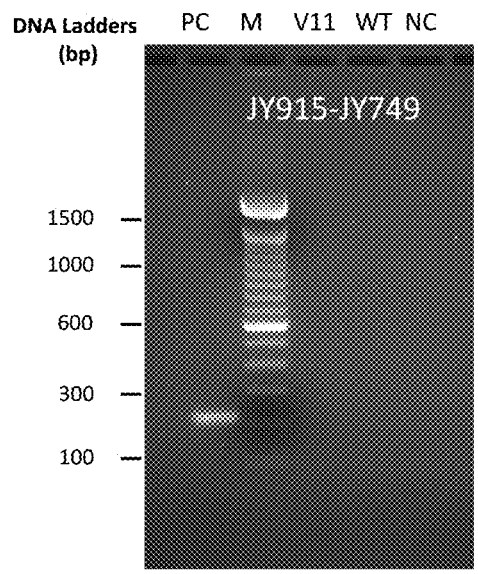

PCR-Based Identification of Vector Backbone sequences. A PCR assay was used to verify the absence of sequence containing the junction between backbone and the DNA insert from pSIM1278. As diagrammed in FIG. 23, each junction was tested using two sets of PCR primers. The standard 30 μl PCR reaction mixture consisted of 3 μl of 10×PCR buffer, 0.6 IA of 10 mM dNTPs, 0.6 μl of 10 μM forward primer, 0.6 μl of 10 μM reverse primer, 100 ng of genomic DNA template, with 0.3 μl of HotMaster Taq polymerase (Fisher BioReagents). The PCR was carried out under the following amplification conditions: 1 cycle of 3 min at 95° C. followed by 40 cycles of 30 sec at 94° C., 30 sec at 55° C., 30 sec at 68° C., and finishing with 10 min at 68° C. Primers were designed to amplify fragments indicative of (1) junctions between DNA insert border regions and flanking backbone DNA or (2) regions entirely within the backbone DNA that flank the DNA insert. The primer pair JY725-JY726 amplified a 377-bp fragment comprising the junction at the Right Border region and flanking backbone, and primers JY915-JY749 were used to amplify a 215-bp backbone fragment flanking the Right Border of both pSIM1278 (see FIG. 23 and Table 18). The primer pair JY718-JY719 amplified a 587-bp fragment comprising the junction at the Left Border region and flanking backbone of pSIM1278, and primers JY1029-JY1030 were used to amplify a 503-bp backbone fragment flanking the Left Border of pSIM1278 (see FIG. 23 and Table 18).

None of the PCR reactions amplified junction regions in either V11 or WT samples, whereas in each case positive controls amplified as expected. Consistent with the Southern data, PCR failed to identify the presence of any backbone DNA in V11. The absence of backbone DNA adjacent to the DNA insert is further supported by the lack of backbone DNA within the insert flanking sequences (see Example 4).

pellet was dissolved in 20 µl 1×TE followed by addition of 2 µl DNA gel loading buffer, which consists of 40% sucrose and 0.35% Orange G (Sigma) in water.

Membrane Preparation. Digested DNA was loaded on a large 0.7% agarose gel (170 ml) containing 0.5×TBE buffer and 3-5 µl ethidium bromide (10 mg/ml) and run at 30 volts for 18 hrs. The gel was photographed using a gel documentation system from Alpha Innotech (Santa Clara, Calif.), and then depurinated by submerging it into 0.25 N HCl for 20 min. After subsequent denaturation in 0.5 M NaOH/1.5 M NaCl for 2×15 min and neutralization in 1.5 M NaCl and 0.5

TABLE 18

Primer Sequences and PCR Products for Detection of Backbone Adjacent to Left and Right Borders of pSIM1278

PCR Primers for Detecting Backbone Adjacent to Left Border of pSIM1278

| Name | Sequence (5' to 3') | Location in pSIM1278 | Product length (bp) | Backbone (bp) |
|---|---|---|---|---|
| JY719 | GAGCTGTTGGCTGGCTGGAAG (SEQ ID NO: 17) | 19,637-1,9657 (backbone) | 587 | 24 |
| JY718 | GTTGGAAATCAATTATCACTGAG (SEQ ID NO: 18) | 541-563 (AGP promoter) | | |
| JY1029 | CCGTTCTTCCGAATAGCATC (SEQ ID NO: 19) | 19,507-19,526 (backbone) | 503 | 154 |
| JY1030 | CGGGTTATCGGTTCTTAACG (SEQ ID NO: 20) | 330-349 (AGP promoter) | | |

PCR Primers for Detecting Backbone Adjacent to Right Border of pSIM1278

| Name | Sequence (5' to 3') | Location in pSIM1278 | Product length (bp) | Backbone (bp) |
|---|---|---|---|---|
| JY725 | GCTTCCCGTATACAACATAACATG (SEQ ID NO: 21) | 9,813-9,836 (GBSS promoter) | 377 | 41 |
| JY726 | GATCTCAAACAAACATACACAGCG (SEQ ID NO: 22) | 10,166-10,189 (backbone) | | |
| JY1029 | CCGTTCTTCCGAATAGCATC (SEQ ID NO: 19) | 19,507-19,526 (backbone) | 215 | 215 |
| JY1030 | CGGGTTATCGGTTCTTAACG (SEQ ID NO: 20) | 330-349 (AGP promoter) | | |

Analysis of Genetic Stability

Materials. DNA insert stability was demonstrated in the originally transformed material (G0) by extracting and evaluating DNA from leaves of plants that had been propagated in vitro and never planted in soil. For G1 and G2 analyses, leaves of two plants from each event and one plant from each control were collected from field trial. For the G3 analyses, leaves of two plants from each event and one plant from each control were collected from plants grown in a greenhouse. The G2 tubers of unmodified Snowden control and V11 were harvested from Hancock, Wis., Florida, and Michigan State University field trial sites and were used for the catechol assay.

DNA Isolation. Genomic DNA was isolated from the leaves of greenhouse-grown plants as described above for use in the following assays.

Figure 25:
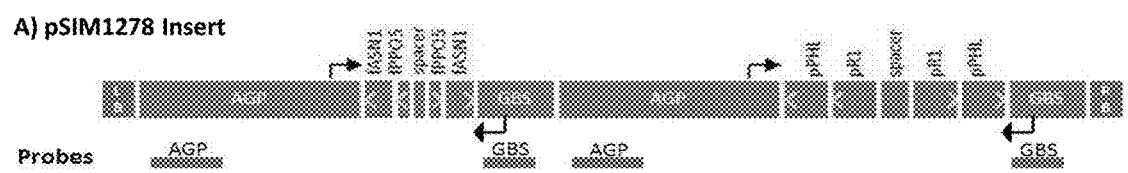
FIG. 25 shows probes used for the Southern blot stability analysis for the pSIM1278 insert.

Southern Blot Analysis. Extracted genomic DNA from leaves was digested with EcoRV and hybridized with two probes (GBS and AGP). The probes used in the Southern blot analysis are depicted in FIG. 25. 3 µg of DNA was digested overnight in 400 µl final volume with at least 5 µl (10 units/µl) restriction enzyme (Invitrogen) at 37° C. Digested DNA was concentrated by ethanol precipitation (40 µl of 3M NaOAc, pH 5.3 and 1 ml ethanol) at −80° C. for 10 min followed by a wash with 70% ethanol. The DNA M Tris-HCl, pH7.5, for 2×15 min on a shaker at room temperature and equilibrated with 10×SSC for 10 min. The transfer of DNA to the nylon membrane was carried out using 10×SSC according to a standard capillary transfer method (Sambrook and Russell 2001).

Northern Blot Methods

Plant material. Gene expression levels were determined by carrying out RNA gel blot analyses on tubers, stolons, roots, stems, leaves, and flowers of greenhouse-grown plants of V11. Three replications per event were used in the analysis.

RNA Isolation. RNA was extracted from 1 g of tuber and root tissue using Plant RNA reagent (Invitrogen, Carlsbad, Calif.), whereas Trizol reagent (Invitrogen) was used to extract RNA from leaves, flowers and stems. The concentration of isolated RNA was measured spectrophotometrically at 260 nm, and RNA quality was confirmed by running a sample on a 1% agarose gel with 1×MOPS buffer (200 mM MOPS, 50 mM NaOAc, 20 mM EDTA, pH7.0) for 30-60 min at 90 volts.

RNA transfer. 20-25 µg of RNA was denatured in RNA loading dye (Sigma) for 10-min at 650 C followed by incubation on ice for 5-min. Denatured RNA was loaded onto an RNA gel containing 1% agarose, 1×MOPS, 0.1-0.25 µg/ml ethidium bromide and 2% formaldehyde (5.5 ml 36.5% stock in 100 ml solution). The gel was run at 80-85 volts for 2-3 hrs and then photographed using the gel documentation system from Alpha Innotech (Santa Clara, Calif.). The gel was soaked twice in 10×SSC for 15-min to remove the formaldehyde. RNA was transferred from the gel to a positively charged nylon membrane (Roche, Indianapolis) by capillary blotting with 10×SSC for 16-18 hrs, and the transferred RNA was stabilized onto the filter by UV cross-linking (UVP, Upland, Calif.). The RNA-containing membrane was stored at 40° C.

Preparation of DIG labeled Probe. A PCR based method was used to prepare DIG labeled probes for four target transcripts and an internal control of 18s rRNA. A typical 50 μl labeling reaction consisted of 5 μl HotMaster Taq Buffer (Fisher BioReagents), 2-5 μl of 10 μM forward primer, 2-5 μl of 10 μM reverse primer, 5 μl DIG-labeled dNTP (Roche, Indianapolis), 5-30 ng plasmid template, 0.50-0.75 μl HotMaster Taq polymerase, and dH2O for a total volume of 50 PCR conditions were specific for each DIG-labeled probe. The DIG-labeled probe was checked on 1% agarose gel and always ran slower than the control.

PCR product. The probe was denatured before use by incubating for 5 min at 100° C. and then transferring to ice. Hybridization. Nylon membranes containing transferred RNA were pre-hybridized in 40 ml pre-warmed DIG Easy Hybridization solution (Roche, Indianapolis) for at least 1-4 hrs at 20-25 rpm in a hybridization oven set at 42° C. (Amerex Instruments). The hybridization solution was replaced by a mix of 40 ml fresh pre-warmed hybridization solution and 25-50 μl of denatured DIG-labeled probe, and the membrane was incubated in this mix for 3-16 hrs at 42° C. The hybridization solution can be store at −20° C. and reused. The reused hybridization solution was heated at 68° C. for 10 minutes before use.

Sequence Analysis

Potato material. Leaves from greenhouse-grown event V11 and untransformed Snowden plants were used to extract DNA for characterization of the insert junctions.

DNA Isolation. Genomic DNA was isolated from the leaves of greenhouse-grown plants as described above for use in the following assays.

Adapter ligation-mediated PCR Junction fragments were amplified by PCR using digested DNA ligated with adapter primers AP1 and AP2 as described by O'Malley et al., 2007. Briefly, 200 ng genomic DNA was digested for 3-5 hours with a restriction enzyme for which an adapter had been designed (EcoRI, HindIII, BamHI, AseI/NdeI.). The digested DNA was ligated with its respective oligonucleotide adapter in a reaction with 1× T4 Ligation Buffer, 1.5 units T4 DNA Ligase, 64 ng digest DNA fragments, 0.3 mM ATP, and the adapter to a final concentration of 0.1 mM. The ligation reaction was used as template for the primary PCR, carried out with a DNA insert-specific primer and AP1 with Hot Master Taq polymerase (Fisher BioReagents) under the following amplification conditions: 1 cycle of 3 min at 95° C. followed by 30 cycles of 30 sec at 94° C., 30 sec at 60° C., 4 min at 68° C., and finishing with 10 min at 68° C. A 1 μl aliquot of the primary PCR product was used for secondary reactions (1 cycle of 3 min at 95° C.; 35 cycles of 30 sec at 94° C., 30 sec at 62° C., 2.5 min at 68° C.; 1 cycle of 10 min at 68° C.) with a nested DNA insert-specific primer and AP2. This protocol was performed for untransformed control plants along with V11. Products of the secondary PCR were run on 1% agarose in TAE buffer. Bands unique to V11 were gel-extracted using a Qiagen QIAquick Gel Extraction kit, cloned into pGEM-T Easy vector (Promega, Madison Wis.), and sequenced. Primers spanning the junction between DNA insert and chromosomal flanking DNA were designed and used to confirm sequences in genomic DNA.

Example 11. Phenotypic Methods

Varieties grown in field trials are described in Table 19. In 2012, test and control varieties were grown at all sites. In 2013, test, control, and reference varieties were grown at all sites. Reference varieties are commercially-available varieties that provide a range of values common to conventional potatoes.

For the 2012 evaluations, nutrient film technology (NFT)-produced mini-tubers for V11 and the control variety were planted. This NFT seed was grown at CSS Farms in Colorado City, Colo. G0 plants from tissue culture were used to grow mini-tubers using nutrient film technology, in which seed is propagated hydroponically using water enriched with dissolved nutrients. In this system, a large number of small seed can be produced because multiple seed harvests from each plant are possible.

For the 2013 evaluations, field-grown G1 seed tubers from each event and the control variety were used to plant the field trials. This seed was grown on a seed farm in Cody, Nebr. Field-grown G1 seed is typically larger than NFT mini-tuber seed and resembles typical sized potatoes.

TABLE 19

Varieties in Field Trials

| Variety | Type | Genotype | Seed Type | Seed Source |
| --- | --- | --- | --- | --- |
| 2012 | | | | |
| Snowden | Control | N/A | G0 mini-tubers | CSS Farms - Colorado City, CO |
| V11 | Test | pSIM1278 | | |
| 2013 | | | | |
| Snowden | Control | N/A | Field-grown G1-tubers | CSS Farms - Cody, NE |
| V11 | Test | pSIM1278 | | |
| Gala | Reference | N/A | | |
| Purple Majesty | Reference | N/A | | |
| C0095051-7w | Reference | N/A | | |
| Norkotah | Reference | N/A | | |

N/A = not applicable

The experiments were established in a randomized complete block design (RCB). The RCB is typical for the evaluation of new potato varieties and events. In 2012, each plot consisted of four rows (except the site in Adams Co. Wis. 2012 which had 3 rows) approximately 20 feet long, each containing 20 mini-tubers. There were three replicates at each site. In-row seed spacing was approximately 12 inches. The mini-tubers were either mechanically or hand planted to a depth of 3-6 inches. In 2013, the sites had plots that consisted of four rows. Each row was approximately 20 feet long, each containing 20 field-grown G1 seed pieces. There were four replicates at each site. In-row seed spacing was approximately 12 inches. The tubers were either mechanically or hand planted to a depth of 3-6 inches.

The agronomic practices and pest control measures used were location-specific and were typical for potato cultivation. They were recommended by both regional potato extension specialists and agronomists and they related to all aspects of soil preparation, fertilizer application, irrigation, and pesticide-based control methods. An example of typical inputs for Snowden potato production is given in Table 20. V11 and untransformed varieties received identical inputs and treatments within each site. The trial sites selected for the phenotypic evaluations were different agricultural zones and represented the main production areas for potatoes in the U.S.

TABLE 20

Example of Agronomic Inputs for Snowden Potato Varieties

| | |
|---|---|
| Planting Date | April 1 to May 10 |
| Vine maturity | 110-120 days after planting |
| Planting Rate | 15,000-18,000 seed pieces or 17-23 cwt/A |
| Row Spacing | 34-36" between rows |
| Seed Spacing | Approximately 12" within row |
| Fertilizer | For 500 cwt/A yields and optimum soil test levels: 200 lb N; 100-180 lb $P_2O_5$; 60 lb $K_2O$/acre |
| Yield/Acre | 300-500 cwt/A |

The phenotypic characteristics evaluated are listed in Table 21.

Tubers were harvested during early fall except in St. John's County, Fla., where tubers were harvested in late spring. At harvest, all tubers from one row of each plot were transported to Michigan State University for testing. The grading methods employed were similar to those used to grade commercial potatoes intended for the production of chips.

The specific gravity was determined by using a weight in air/weight in water measurement. Sub-samples of tubers were first weighed in air and then weighed submerged under water at room temperature. From the two measurements, specific gravity was calculated using the following formula: specific gravity=weight in air/(weight in air−weight in water).

Specific gravity is the industry standard for measuring solids and is thus an important characteristic to compare V11 to its parental control, Snowden.

TABLE 21

Characteristics Evaluated

| Characteristic measured | Evaluation timing[1] | Data description | Scale |
|---|---|---|---|
| Early Emergence | Early season | # of plants emerged out of 20 seed pieces planted, scored in middle two rows of each plot at approximately 50% emergence | 0-100% |
| Final Emergence | Early season | # of plants emerged out of 20 seed pieces planted, scored in middle two rows of each plot at approximately complete emergence | 0-100% |
| Stems per Plant | Early season | Number of stems of 10 non-systematically selected plants in the middle rows of each plot | Number of stems per plant |
| Plant Vigor | Midseason | Visual estimate of relative vigor | 1 to 5 point scale[2] |
| Plant Height | Midseason | Measured from the soil surface at the top of the hill, to the top of the uppermost leaf of 10 non-systematically selected plants in the middle rows of each plot | cm |
| Vine Desiccation | Late season | Visual estimation of the percent of vines desiccated in the middle rows of each plot | 0-100% |
| Total Yield | After harvest | Weight of one of the center two rows, scaled to weight per unit area | Cwt/acre |
| U.S. #1 | After harvest | Total tuber weight minus the weight of oversize and pickout tubers | Cwt/acre |
| Tubers per plant | After harvest | Total number of tubers in a single-row divided by the total number of plants in the same row | Tubes/plant |
| Grade A | After harvest | Tubers 2 to 3.25 in. diameter | % of tubers by weight |
| Grade B | After harvest | Tubers <2 in. diameter | % of tubers by weight |
| Oversize (unusable) | After harvest | Tubers >3.25 in. diameter | % of tubers by weight |
| Pickout (unusable) | After harvest | Unmarketable tubers based on visual physiological defects | % of tubers by weight |
| Specific gravity | After harvest | Tuber sample weight in air/(weight in air - weight in water) | Numeric specific gravity value |
| Total internal defects | After harvest | Sum of internal defects such as hollow heart, vascular necrosis, internal discoloration, internal brown spot, and nematode or insect damage | % of tubers affected by any internal defect |

[1]Early season observations were made within approximately 45 days after emergence. Midseason observations were made during the early bloom stage. Late season notes were taken during the crop senescence stage prior to chemical or mechanical vine desiccation.
[2]1 to 5 scale for vigor:
1 = severely less than the varietal average; 2 = noticeably less than varietal average, but not severe; 3 = plants are similar to the varietal average; 4 = slightly more than varietal average; 5 = obviously more than the varietal average.

TABLE 22

Common Potato Disease and Insect Symptoms[1]

| Insect or Disease Agent | Symptom |
|---|---|
| *Emposasca fabae* (Potato Leafhopper) | Leaf feeding damage |
| *Epitrix* species (Flea Beetle) | Shot-holes in leaves |

TABLE 22-continued

Common Potato Disease and Insect Symptoms[1]

| Insect or Disease Agent | Symptom |
| --- | --- |
| *Leptinotarsa decemlineata* (Colorado Potato Beetle) | Defoliation |
| *Limonius californicus* (Wireworm) | Bored holes in tubers and shoots |
| *Ostrinia nubilalis* (European Corn Borer) | Severe vine wilting above point of injury |
| *Bactericera* (*Paratrioza*) *cockerelli* (Potato Psyllid) | Yellows |
| *Phthorimaea operculella* (Tuberworm) | Foliar and tuber damage |
| Various aphid spp. | Leaf suckling damage |
| Aster Yellows MLO | Purple top disease |
| Potato Leafroll Virus | Rolling of leaves and net necrosis |
| Potato Spindle Tuber Viroid | Potato spindle tuber disease |
| Potato Virus A, M, X, Y | Mosaic symptoms |
| Tobacco Rattle Virus | Stem mottling |
| *Erwinia carotovora* | Blackleg, aerial stem rot and tuber soft rot |
| *Corynebactium sepedonicum* | Bacterial ring rot |
| *Ralstonia solanacearum* | Brown rot |
| *Phytophthora infestans* | Late blight |
| *Phytophthora erythroseptica* | Pink rot |
| *Verticillium* spp. | Early dying |
| *Sclerotinia sclerotiorum* | *Sclerotinia* stalk rot |
| *Rhizoctonia solani* | Canker |
| *Streptomyces scabies* | Scab |
| *Fusarium* spp. | Dry rot |
| *Pythium ultimum* | Water rot, shell rot, *Pythium* leak |
| *Alternaria solani* | Early blight |
| *Botrytis cinerea* | Gray mold |

[1]All stressors shown here were not necessarily observed at all sites or observation timings. This table is meant to give an accurate list of insects and diseases that may impact potatoes.

Volunteer Potential Methods

Tubers harvested from V11 and control plots in the phenotypic trials were used to plant the volunteer potential study. Conventional reference varieties were provided by the grower from commercial sources.

The experiments were established in a randomized complete block (RCB) design with four replicates at each site. Each plot consisted of three rows approximately 10 feet long. In-row seed spacing was approximately 12 inches and each row contained 10 tubers. The tubers were hand planted to a depth of 3-6 inches.

After tubers were planted in the fall of 2012, the field was monitored for volunteers approximately every two weeks until weather conditions became too cold for plant growth. In the spring, when the weather became suitable for the emergence of volunteers, the field was monitored approximately every two weeks for volunteers until July 2013. The number of volunteers found in each plot was noted in the study notebook and the volunteers were removed and devitalized.

Statistical Analysis

The statistical analysis for phenotypic, grading, and stressor data was performed using SAS 9.3. All data were subjected to analysis of variance using the following linear mixed model: $Y_{ijkl} = \alpha_i + \beta_j + \gamma_{k(j)} + (\alpha\beta)_{il} + \epsilon_{ijkl}$, where $\alpha$=mean of treatment (fixed), $\beta$=effect of site (random), $\gamma$=rep[site] (random), $\epsilon$=residual random error.

Where $\alpha_i$ denotes the mean of the $i^{th}$ treatment (fixed effect), $\beta_j$ denotes the effect of the $j^{th}$ site (random effect), $\gamma_{k(j)}^{\gamma_{k(j)}}$ denotes the random rep effect (within site), $(\alpha\beta)_{ik}$ denotes the interaction between the $i^{th}$ treatment and random $k^{th}$ site effect, and $\epsilon_{ijkl}$ denotes the residual random error.

A significant difference was established with a p-value <0.05. Every effort was made to generate p-values to aid in the interpretation of the data. Some departures from the assumptions of normality and equal variances were allowed since the results were always interpreted in the context of variation observed in the conventional varieties.

Composition Methods

Test, control, and reference tubers for the compositional assessment were collected from the same 2012 and 2013 field trial locations listed in Table 5. Each combination of year, site, material, and replicate represents one sample of six tubers in the compositional assessment. Samples analyzed at 3, 6, and 9 months of storage consisted of 3 tubers and were taken from all sites in 2012 but not from the 2013 locations.

Samples were obtained by randomly selecting mid-sized tubers at harvest from each site and rep. Tuber samples were powdered in an industrial blender with liquid nitrogen and stored at −70° C. until analysis. For acrylamide testing, five pound samples of the potatoes were processed into chips prior to analysis, using standard practices.

Analytical testing was conducted by Covance Laboratories, Inc. in Madison, Wis. with the exception that acrylamide testing was conducted by Covance Laboratories, Inc. in Greenfield, Ind.

Statistical Analysis for Composition

The statistical analysis was performed using SAS 9.3. All data were subjected to analysis of variance using the following linear mixed model: $Y_{ijkl} = \alpha_i + \beta_j \gamma_{k(j)} + (\alpha\beta)_{il} + \epsilon_{ijkl}$, where $\alpha$=mean of treatment (fixed), $\beta$=effect of site (random), $\gamma$=rep[site] (random), $\epsilon$=residual random error.

Where $\alpha_i$ denotes the mean of the $i^{th}$ treatment (fixed effect), $\beta_j$ denotes the effect of the $j^{th}$ site (random effect), $\gamma_{k(j)}^{\gamma_{k(j)}}$ denotes the random rep effect (within site), $(\alpha\beta)_{ik}$ denotes the interaction between the $i^{th}$ treatment and random $k^{th}$ site effect, and $\epsilon_{ijkl}$ denotes the residual random error.

A significant difference was established with a p-value <0.05. Every effort was made to generate p-values to aid in the interpretation of the data. Some departures from the assumptions of normality and equal variances were allowed since the results were always interpreted in the context of variation observed in the conventional varieties.

The tolerance intervals were calculated to contain, with 95% confidence, 99% of the values in the population.

Tolerance intervals were used for compositional data to represent the natural variability among potatoes. The tolerance interval attempts to predict, with a specified level of confidence, the range in which most values of a population will fall. Conventional potato varieties used in the tolerance interval are shown in Table 23 and include varieties suitable for fresh use, for frying, for chipping, and the V11 parental control, Snowden.

TABLE 23

Number of Data Points for Each Test, Control and Reference Variety

| Variety | N Per Attribute | Used in Tolerance Interval? |
|---|---|---|
| V11 | 22 | No |
| Atlantic | 8 | Yes |
| Bintje | 8 | Yes |
| C0095051-7W | 16 | Yes |
| Gala | 16 | Yes |
| Golden Sunburst | 8 | Yes |
| Nicolet | 8 | Yes |
| Norkotah | 16 | Yes |
| Purple Majesty | 16 | Yes |
| Snowden | 21 | Yes |
| TX278 | 8 | Yes |
| Total N | 147 | 125 in tolerance interval |

FURTHER EMBODIMENTS OF THE INVENTION

The research leading to potato varieties which combine the advantageous characteristics referred to above is largely empirical. This research requires large investments of time, labor, and money. The development of a potato cultivar can often take up to eight years or more from greenhouse to commercial usage. Breeding begins with careful selection of superior parents to incorporate the most important characteristics into the progeny. Since all desired traits usually do not appear with just one cross, breeding must be cumulative.

Present breeding techniques continue with the controlled pollination of parental clones. Typically, pollen is collected in gelatin capsules for later use in pollinating the female parents. Hybrid seeds are sown in greenhouses and tubers are harvested and retained from thousands of individual seedlings. The next year one to four tubers from each resulting seedling are planted in the field, where extreme caution is exercised to avoid the spread of virus and diseases. From this first-year seedling crop, several "seed" tubers from each hybrid individual which survived the selection process are retained for the next year's planting. After the second year, samples are taken for density measurements and fry tests to determine the suitability of the tubers for commercial usage. Plants which have survived the selection process to this point are then planted at an expanded volume the third year for a more comprehensive series of fry tests and density determinations. At the fourth-year stage of development, surviving selections are subjected to field trials in several states to determine their adaptability to different growing conditions. Eventually, the varieties having superior qualities are transferred to other farms and the seed increased to commercial scale. Generally, by this time, eight or more years of planting, harvesting and testing have been invested in attempting to develop the new and improved potato cultivars.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed variety or line.

Plant transformation involves the construction of an expression vector which will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid, and can be used alone or in combination with other plasmids, to provide transformed potato plants, using transformation methods as described below to incorporate transgenes into the genetic material of the potato plant(s).

Traditional plant breeding typically relies on the random recombination of plant chromosomes to create varieties that have new and improved characteristics. According to standard, well-known techniques, genetic "expression cassettes," comprising genes and regulatory elements, are inserted within the borders of *Agrobacterium*-isolated transfer DNAs ("T-DNAs") and integrated into plant genomes. *Agrobacterium*-mediated transfer of T-DNA material typically comprises the following standard procedures: (1) in vitro recombination of genetic elements, at least one of which is of foreign origin, to produce an expression cassette for selection of transformation, (2) insertion of this expression cassette, often together with at least one other expression cassette containing foreign DNA, into a T-DNA region of a binary vector, which usually consists of several hundreds of basepairs of *Agrobacterium* DNA flanked by T-DNA border sequences, (3) transfer of the sequences located between the T-DNA borders, often accompanied with some or all of the additional binary vector sequences from *Agrobacterium* to the plant cell, and (4) selection of stably transformed plant cells that display a desired trait, such as an increase in yield, improved vigor, enhanced resistance to diseases and insects, or greater ability to survive under stress.

Thus, genetic engineering methods rely on the introduction of foreign, not-indigenous nucleic acids, including regulatory elements such as promoters and terminators, and genes that are involved in the expression of a new trait or function as markers for identification and selection of transformants, from viruses, bacteria and plants. Marker genes are typically derived from bacterial sources and confer antibiotic or herbicide resistance. Classical breeding methods are laborious and time-consuming, and new varieties typically display only relatively modest improvements.

In the "anti-sense" technology, the sequence of native genes is inverted to silence the expression of the gene in transgenic plants. However, the inverted DNA usually contains new and uncharacterized open reading frames inserted between the promoter and the terminator that encode foreign amino acid sequences that may be undesirable as they interfere with plant development and/or reduce their nutritional value.

Expression Vectors for Potato Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Fraley et al., Proc. Natl. Acad. Sci. U.S.A., 80:4803 (1983). Another commonly used selectable marker gene is the hygromycin phosphotransferase gene which confers resistance to the antibiotic hygromycin. Vanden Elzen et al., Plant Mol. Biol., 5:299 (1985).

Additional selectable marker genes of bacterial origin that confer resistance to antibiotics include gentamycin acetyl transferase, streptomycin phosphotransferase and aminoglycoside-3'-adenyl transferase, the bleomycin resistance determinant. Hayford et al., Plant Physiol. 86:1216 (1988), Jones et al., Mol. Gen. Genet., 210:86 (1987), Svab et al., Plant Mol. Biol. 14:197 (1990) Hille et al., Plant Mol. Biol. 7:171 (1986). Other selectable marker genes confer resistance to herbicides such as glyphosate, glufosinate or bromoxynil. Comai et al., Nature 317:741-744 (1985), Gordon-Kamm et al., Plant Cell 2:603-618 (1990) and Stalker et al., Science 242:419-423 (1988).

Selectable marker genes for plant transformation not of bacterial origin include, for example, mouse dihydrofolate reductase, plant 5-enolpyruvylshikimate-3-phosphate synthase and plant acetolactate synthase. Eichholtz et al., Somatic Cell Mol. Genet. 13:67 (1987), Shah et al., Science 233:478 (1986), Charest et al., Plant Cell Rep. 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase. Jefferson, R. A., Plant Mol. Biol. Rep. 5:387 (1987), Teen et al., EMBO J. 8:343 (1989), Koncz et al., Proc. Natl. Acad. Sci. USA 84:131 (1987), DeBlock et al., EMBO J. 3:1681 (1984).

In vivo methods for visualizing GUS activity that do not require destruction of plant tissue are available. Molecular Probes publication 2908, IMAGENE GREEN, p. 1-4 (1993) and Naleway et al., J. Cell Biol. 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., Science 263:802 (1994). GFP and mutants of GFP may be used as screenable markers.

Expression Vectors for Potato Transformation: Promoters

Genes included in expression vectors must be driven by a nucleotide sequence comprising a regulatory element, for example, a promoter. Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters that initiate transcription only in a certain tissue are referred to as "tissue-specific". A "cell-type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

A. Inducible Promoters

An inducible promoter is operably linked to a gene for expression in potato. Optionally, the inducible promoter is operably linked to a nucleotide sequence encoding a signal sequence which is operably linked to a gene for expression in potato. With an inducible promoter the rate of transcription increases in response to an inducing agent.

Any inducible promoter can be used in the instant invention. See Ward et al., Plant Mol. Biol. 22:361-366 (1993). Exemplary inducible promoters include, but are not limited to, that from the ACEI system which responds to copper (Mett et al., PNAS 90:4567-4571 (1993)); In2 gene from maize which responds to benzenesulfonamide herbicide safeners (Hershey et al., Mol. Gen Genetics 227:229-237 (1991) and Gatz et al., Mol. Gen. Genetics 243:32-38 (1994)) or Tet repressor from Tn10 (Gatz et al., Mol. Gen. Genetics 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. USA* 88:0421 (1991).

B. Constitutive Promoters

A constitutive promoter is operably linked to a gene for expression in potato or the constitutive promoter is operably linked to a nucleotide sequence encoding a signal sequence which is operably linked to a gene for expression in potato.

Many different constitutive promoters can be utilized in the instant invention. Exemplary constitutive promoters include, but are not limited to, the promoters from plant viruses such as the 35S promoter from CaMV (Odell et al., Nature 313:810-812 (1985)) and the promoters from such genes as rice actin (McElroy et al., Plant Cell 2: 163-171 (1990)); ubiquitin (Christensen et al., Plant Mol. Biol. 12:619-632 (1989) and Christensen et al., Plant Mol. Biol. 18:675-689 (1992)); pEMU (Last et al., Theor. Appl. Genet. 81:581-588 (1991)); MAS (Velten et al., EMBO J. 3:2723-2730 (1984)) and maize H3 histone (Lepetit et al., Mol. Gen. Genetics 231:276-285 (1992) and Atanassova et al., Plant Journal 2 (3): 291-300 (1992)).

The ALS promoter, XbaI/NcoI fragment 5' to the Brassica napus ALS3 structural gene (or a nucleotide sequence similarity to said XbaI/NcoI fragment), represents a particularly useful constitutive promoter. See PCT application WO 96/30530.

C. Tissue-Specific or Tissue-Preferred Promoters

A tissue-specific promoter is operably linked to a gene for expression in potato. Optionally, the tissue-specific promoter is operably linked to a nucleotide sequence encoding a signal sequence which is operably linked to a gene for expression in potato. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter—such as that from the phaseolin gene (Murai et al., Science 23:476-482 (1983) and Sengupta-Gopalan et al., Proc. Natl. Acad. Sci. USA 82:3320-3324 (1985)); a leaf-specific and light-induced promoter such as that from cab or rubisco (Simpson et al., EMBO J. 4(11):2723-2729 (1985) and Timko et al., Nature 318:579-582 (1985)); an anther-specific promoter such as that from LAT52 (Twell et al., Mol. Gen. Genetics 217:240-245 (1989)); a pollen-specific promoter such as that from Zm13 (Guerrero et al., Mol. Gen. Genetics 244:161-168 (1993)) or a microspore-preferred promoter such as that from apg (Twell et al., Sex. Plant Reprod. 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example, Becker et al., Plant Mol. Biol. 20:49 (1992); Close, P. S., Master's Thesis, Iowa State University (1993); Knox, C., et al., Plant Mol. Biol. 9:3-17 (1987); Lerner et al., Plant Physiol. 91:124-129 (1989); Frontes et al., Plant Cell 3:483-496 (1991); Matsuoka et al., Proc. Natl. Acad. Sci. 88:834 (1991); Gould et al., J. Cell. Biol. 108:1657 (1989); Creissen et al., Plant J. 2:129 (1991); Kalderon, et al., Cell 39:499-509 (1984); Steifel, et al., Plant Cell 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114:92-6 (1981).

According to a preferred embodiment, the transgenic plant provided for commercial production of foreign protein is a potato plant. In another preferred embodiment, the biomass of interest is seed or tubers. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269: 284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene(s) to engineer plants that are resistant to specific pathogen strains. See, for example Jones et al., Science 266:789 (1994) (cloning of the tomato Cf-9 gene for resistance to *Cladosporium fulvum*); Martin et al., Science 262: 1432 (1993) (tomato Pto gene for resistance to *Pseudomonas syringae* pv. tomato encodes a protein kinase); Mindrinos et al. Cell 78:1089 (1994) (*Arabidopsis* RSP2 gene for resistance to *Pseudomonas syringae*).

B. A gene conferring resistance to a pest, such as soybean cyst nematode. See e.g., PCT Application WO 96/30517; PCT Application WO 93/19181.

C. A *Bacillus thuringiensis* protein, a derivative thereof or a synthetic polypeptide modeled thereon. See, for example, Geiser et al., Gene 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

D. A lectin. See, for example, Van Damme et al., Plant Molec. Biol. 24:25 (1994), who disclose the nucleotide sequences of several Clivia miniata mannose-binding lectin genes.

E. A vitamin-binding protein such as avidin. See PCT application US 93/06487 which teaches the use of avidin and avidin homologs as larvicides against insect pests.

F. An enzyme inhibitor, for example, a protease or proteinase inhibitor or an amylase inhibitor. See, for example, Abe et al., J. Biol. Chem. 262:16793 (1987) (nucleotide sequence of rice cysteine proteinase inhibitor), Huub et al., Plant Molec. Biol. 21:985 (1993) (nucleotide sequence of cDNA encoding tobacco proteinase inhibitor I), Sumitani et al., Biosci. Biotech. Biochem. 57:1243 (1993) (nucleotide sequence of *Streptomyces nitrosporeus* α-amylase inhibitor) and U.S. Pat. No. 5,494,813 (Hepher and Atkinson, issued Feb. 27, 1996).

G. An insect-specific hormone or pheromone such as an ecdysteroid or juvenile hormone, a variant thereof, a mimetic based thereon, or an antagonist or agonist thereof. See, for example, the disclosure by Hammock et al., Nature 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, J. Biol. Chem. 269:9 (1994) (expression cloning yields DNA coding for insect diuretic hormone receptor), and Pratt et al., Biochem. Biophys. Res. Comm. 163:1243 (1989) (an allostatin is identified in Diploptera puntata). See also U.S. Pat. No. 5,266,317 to Tomalski et al., who disclose genes encoding insect-specific, paralytic neurotoxins.

I. An insect-specific venom produced in nature by a snake, a wasp, etc. For example, see Pang et al., Gene 116:165 (1992), for disclosure of heterologous expression in plants of a gene coding for a scorpion insectotoxic peptide.

J. An enzyme responsible for a hyperaccumulation of a monoterpene, a sesquiterpene, a steroid, hydroxamic acid, a phenylpropanoid derivative or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 (Scott et al.), which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23:691 (1993), who teach the nucleotide sequence of a cDNA encoding tobacco hornworm chitinase, and Kawalleck et al., Plant Molec. Biol. 21:673 (1993), who provide the nucleotide sequence of the parsley ubi4-2 polyubiquitin gene.

L. A molecule that stimulates signal transduction. For example, see the disclosure by Botella et al., Plant Molec. Biol. 24:757 (1994), of nucleotide sequences for mung bean calmodulin cDNA clones, and Griess et al., Plant Physiol. 104:1467 (1994), who provide the nucleotide sequence of a maize calmodulin cDNA clone.

M. A hydrophobic moment peptide. See PCT application WO 95/16776, which discloses peptide derivatives of Tachyplesin which inhibit fungal plant pathogens, and PCT application WO 95/18855 which teaches synthetic antimicrobial peptides that confer disease resistance.

N. A membrane permease, a channel former or a channel blocker. For example, see the disclosure of Jaynes et al., Plant Sci 89:43 (1993), of heterologous expression of a cecropin-β lytic peptide analog to render transgenic tobacco plants resistant to *Pseudomonas solanacearum.*

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol. 28:451 (1990). Coat protein-mediated resistance has been conferred upon transformed plants against alfalfa mosaic virus, cucumber mosaic virus and tobacco mosaic virus.

P. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q. A virus-specific antibody. See, for example, Tavladoraki et al., Nature 366:469 (1993), who show that transgenic plants expressing recombinant antibody genes are protected from virus attack.

R. A developmental-arrestive protein produced in nature by a pathogen or a parasite. Thus, fungal endo-α-1, 4-D-polygalacturonases facilitate fungal colonization and plant nutrient release by solubilizing plant cell wall homo-α-1, 4-D-galacturonase. See Lamb et al., Bio/Technology 10:1436 (1992). The cloning and characterization of a gene which encodes a bean endopolygalacturonase-inhibiting protein is described by Toubart et al., Plant J. 2:367 (1992).

S. A developmental-arrestive protein produced in nature by a plant. For example, Logemann et al., Bio/Technology 10:305 (1992), have shown that transgenic plants expressing the barley ribosome-inactivating gene have an increased resistance to fungal disease.

T. Genes involved in the Systemic Acquired Resistance (SAR) Response and/or the pathogenesis-related genes. Briggs, S. Current Biology, 5(2) (1995).

U. Antifungal genes. See Cornelissen and Melchers, Plant Physiol., 101:709-712 (1993); Parijs et al., Planta 183:258-264 (1991) and Bushnell et al., Can. J. of Plant Path. 20(2):137-149 (1998).

V. Genes that confer resistance to *Phytophthora* blight, such as the R1, R2, R3, R4 and other resistance genes. See, Naess, S. K., et. al., (2000) Resistance to late blight in *Solanum bulbocastanum* is mapped to chromosome 8. Theor. Appl. Genet. 101: 697-704 and Li, X., et. al., (1998) Autotetraploids and genetic mapping using common AFLP markers: the R2 allele conferring resistance to *Phytophthora infestans* mapped on potato chromosome 4. Theor. Appl. Genet. 96: 1121-1128.

2. Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee et al., EMBO J. 7:1241 (1988), and Miki et al., Theor. Appl. Genet. 80:449 (1990), respectively.

B. Glyphosate (resistance impaired by mutant 5-enolpyruvlshikimate-3-phosphate synthase (EPSP) and aroA genes, respectively) and other phosphono compounds such as glufosinate (phosphinothricin acetyl transferase (PAT) and *Streptomyces hygroscopicus* PAT bar genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., Bio/Technology 7:61 (1989) describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop are the Acc1-S1, Acc1-S2, and Acc2-S3 genes described by Marshall et al., Theor. Appl. Genet. 83:435 (1992).

C. An herbicide that inhibits photosynthesis, such as a triazine (psbA and gs+ genes) or a benzonitrile (nitrilase gene). Przibila et al., Plant Cell 3:169 (1991), describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Nos. 53435, 67441 and 67442. Cloning and expression of DNA coding for a glutathione S-transferase is described by Hayes et al., Biochem. J. 285:173 (1992).

D. Acetohydroxy acid synthase, which has been found to make plants that express this enzyme resistant to multiple types of herbicides, has been introduced into a variety of plants. See Hattori et al., Mol. Gen. Genet. 246:419, 1995. Other genes that confer tolerance to herbicides include a gene encoding a chimeric protein of rat cytochrome P4507A1 and yeast NADPH-cytochrome P450 oxidoreductase (Shiota et al., Plant Physiol., 106:17, 1994), genes for glutathione reductase and superoxide dismutase (Aono et al., Plant Cell Physiol. 36:1687, 1995), and genes for various phosphotransferases (Datta et al., Plant Mol. Biol. 20:619, 1992).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; 5,767,373; and international publication WO 01/12825.

3. Genes that Confer or Contribute to a Value-Added Trait, Such as:

A. Modified fatty acid metabolism, for example, by transforming a plant with an antisense gene of stearyl-ACP desaturase to increase stearic acid content of the plant. See Knultzon et al., *Proc. Natl. Acad. Sci. USA* 89:2625 (1992).

B. Decreased phytate content—1) Introduction of a phytase-encoding gene would enhance breakdown of phytate, adding more free phosphate to the transformed plant. For example, see Van Hartingsveldt et al., *Gene* 127:87 (1993), for a disclosure of the nucleotide sequence of an *Aspergillus niger* phytase gene. 2) A gene could be introduced that reduced phytate content. In maize, for example, this could be accomplished by cloning and then reintroducing DNA associated with the single allele which is responsible for maize mutants characterized by low levels of phytic acid. See Raboy et al., *Maydica* 35:383 (1990).

C. Modified carbohydrate composition effected, for example, by transforming plants with a gene coding for an enzyme that alters the branching pattern of starch. See Shiroza et al., *J. Bacteriol.* 170:810 (1988) (nucleotide sequence of *Streptococcus* mutants fructosyltransferase gene), Steinmetz et al., *Mol. Gen. Genet.* 20:220 (1985) (nucleotide sequence of *Bacillus subtilis* levansucrase gene), Pen et al., *Bio/Technology* 10:292 (1992) (production of transgenic plants that express *Bacillus lichenifonnis* α-amylase), Elliot et al., *Plant Molec. Biol.* 21:515 (1993) (nucleotide sequences of tomato invertase genes), Søgaard et al., *J. Biol. Chem.* 268:22480 (1993) (site-directed mutagenesis of barley α-amylase gene), and Fisher et al., *Plant Physiol.* 102:1045 (1993) (maize endosperm starch branching enzyme II).

D. Elevated oleic acid via FAD-2 gene modification and/or decreased linolenic acid via FAD-3 gene modification. See U.S. Pat. Nos. 6,063,947; 6,323,392; and international publication WO 93/11245.

4. Genes that Control Male Sterility

A. Introduction of a deacetylase gene under the control of a tapetum-specific promoter and with the application of the chemical N-Ac-PPT. See international publication WO 01/29237.

B. Introduction of various stamen-specific promoters. See international publications WO 92/13956 and WO 92/13957.

C. Introduction of the barnase and the barstar genes. See Paul et al., Plant Mol. Biol. 19:611-622, 1992).

Methods for Potato Transformation

Numerous methods for plant transformation have been developed including biological and physical plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (*CRC Press, Inc.* Boca Raton, 1993) pages 67-88. In addition, expression vectors and in-vitro culture methods for plant cell or tissue transformation and regeneration of plants are available. See, for example, Gruber et al., "Vectors for Plant Transformation" in Methods in Plant Molecular Biology and Biotechnology, Glick, B. R. and Thompson, J. E. Eds. (*CRC Press, Inc.*, Boca Raton, 1993) pages 89-119.

A. *Agrobacterium*-mediated Transformation—One method for introducing an expression vector into plants is based on the natural transformation system of *Agrobacterium*. See, for example, Horsch et al., Science 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant Sci. 10:1 (1991). Descriptions of *Agrobacterium* vector systems and methods for *Agrobacterium*-mediated gene transfer are provided by Gruber et al., supra, Miki et al., supra and Moloney et al., *Plant Cell Reports* 8:238 (1989). See also, U.S. Pat. No. 5,563,055 (Townsend and Thomas), issued Oct. 8, 1996.

B. Direct Gene Transfer—Several methods of plant transformation collectively referred to as direct gene transfer have been developed as an alternative to *Agrobacterium*-mediated transformation. A generally applicable method of plant surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987); *Sanford, J. C., Trends Biotech.* 6:299 (1988); Klein et al., *Bio/Tech.* 6:559-563 (1988); *Sanford, J. C. Physiol Plant* 7:206 (1990); Klein et al., *Biotechnology* 10:268 (1992). See also U.S. Pat. No. 5,015,580 (Christou, et al.), issued May 14, 1991 and U.S. Pat. No. 5,322,783 (Tomes, et al.), issued Jun. 21, 1994.

Another method for physical delivery of DNA to plants is sonication of target cells. Zhang et al., *Bio/Technology* 9:996 (1991). Alternatively, liposome and spheroplast fusion have been used to introduce expression vectors into plants. Deshayes et al., *EMBO* 4:2731 (1985); Christou et al., *Proc Natl. Acad. Sci. USA* 84:3962 (1987). Direct uptake of DNA into protoplasts using $CaCl_2$ precipitation, polyvinyl alcohol or poly-L-ornithine has also been reported. Hain et al., *Mol. Gen. Genet.* 199:161 (1985) and Draper et al., *Plant Cell Physiol.* 23:451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4:1495-1505 (1992) and Spencer et al., *Plant Mol. Biol.* 24:51-61 (1994).

Following transformation of potato target tissues, expression of the above-described selectable marker genes allows for preferential selection of transformed cells, tissues and/or plants, using regeneration and selection methods well known in the art.

The foregoing methods for transformation would typically be used for producing a transgenic variety. The transgenic variety could then be crossed with another (non-transformed or transformed) variety in order to produce a new transgenic variety. Alternatively, a genetic trait that has been engineered into a particular potato line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties that do not contain that gene. As used herein, "crossing" can refer to a simple X by Y cross or the process of backcrossing depending on the context.

Persons of ordinary skill in the art will recognize that when the term potato plant is used in the context of the present invention, this also includes derivative varieties that retain the essential distinguishing characteristics of V11, such as a gene converted plant of that variety or a transgenic derivative having one or more value-added genes incorporated therein (such as herbicide or pest resistance). Backcrossing methods can be used with the present invention to improve or introduce a characteristic into the variety. The term "backcrossing" as used herein refers to the repeated crossing 1, 2, 3, 4, 5, 6, 7, 8, 9 or more times of a hybrid progeny back to the recurrent parents. The parental potato plant which contributes the gene(s) for the one or more desired characteristics is termed the nonrecurrent or donor parent. This terminology refers to the fact that the nonrecurrent parent is used one time in the backcross protocol and therefore does not recur. The parental potato plant to which the gene or genes from the nonrecurrent parent are transferred is known as the recurrent parent as it is used for several rounds in the backcrossing protocol. In a typical backcross protocol, the original variety of interest (recurrent parent) is crossed to a second variety (nonrecurrent parent) that carries the gene(s) of interest to be transferred. The resulting progeny from this cross are then crossed again to the recurrent parent and the process is repeated until a potato plant is obtained wherein essentially all of the desired morphological and physiological characteristics of the recurrent parent are recovered in the converted plant, in addition to the one or more genes transferred from the nonrecurrent parent.

The selection of a suitable recurrent parent is an important step for a successful backcrossing procedure. The goal of a backcross protocol is to alter or substitute one or more traits or characteristics in the original variety. To accomplish this, one or more genes of the recurrent variety are modified, substituted or supplemented with the desired gene(s) from the nonrecurrent parent, while retaining essentially all of the rest of the desired genes, and therefore the desired physiological and morphological constitution of the original variety. The choice of the particular nonrecurrent parent will depend on the purpose of the backcross. One of the major purposes is to add some commercially desirable, agronomically important trait to the plant. The exact backcrossing protocol will depend on the characteristic or trait being altered or added to determine an appropriate testing protocol. Although backcrossing methods are simplified when the characteristic being transferred is a dominant allele, a recessive allele may also be transferred. In this instance, it may be necessary to introduce a test of the progeny to determine if the desired characteristic has been successfully transferred.

Likewise, transgenes can be introduced into the plant using any of a variety of established recombinant methods well-known to persons skilled in the art, such as: Gressel, 1985, Biotechnologically Conferring Herbicide Resistance in Crops: The Present Realities, In *Molecular Form and Function of the Plant Genome*, L. van Vloten-Doting, (ed.), Plenum Press, New York; Huttner, S. L., et al., 1992, Revising Oversight of Genetically Modified Plants, Bio/Technology; Klee, H., et al., 1989, Plant Gene Vectors and Genetic Transformation: Plant Transformation Systems Based on the use of *Agrobacterium tumefaciens, Cell Culture and Somatic Cell Genetics of Plants*; Koncz, C., et al., 1986, The Promoter of $T_L$-DNA Gene 5 Controls the Tissue-Specific Expression of Chimeric Genes Carried by a Novel Type of *Agrobacterium* Binary Vector; *Molecular and General Genetics*; Lawson, C., et al., 1990, Engineering Resistance to Mixed Virus Infection in a Commercial Potato Cultivar: Resistance to Potato Virus X and Potato Virus Y in Transgenic Russet Burbank, *Bio/Technology*; Mitsky, T. A., et al., 1996, Plants Resistant to Infection by PLRV. U.S. Pat. No. 5,510,253; Newell, C. A., et al., 1991, *Agrobacterium*-Mediated Transformation of *Solanum tuberosum* L. Cv. Russet Burbank, *Plant Cell Reports*; Perlak, F. J., et al., 1993, Genetically Improved Potatoes: Protection from Damage by Colorado Potato Beetles, *Plant Molecular Biology*; all of which are incorporated herein by reference for this purpose.

Many traits have been identified that are not regularly selected for in the development of a new variety but that can be improved by backcrossing and genetic engineering techniques. These traits may or may not be transgenic; examples of these traits include but are not limited to: herbicide resistance; resistance to bacterial, fungal or viral disease; insect resistance; uniformity or increase in concentration of starch and other carbohydrates; enhanced nutritional quality; decrease in tendency of tuber to bruise; and decrease in the rate of starch conversion to sugars. These genes are generally inherited through the nucleus. Several of these traits are described in U.S. Pat. No. 5,500,365, U.S. Pat. No. 5,387,756, U.S. Pat. No. 5,789,657, U.S. Pat. No. 5,503,999, U.S. Pat. No. 5,589,612, U.S. Pat. No. 5,510,253, U.S. Pat. No. 5,304,730, U.S. Pat. No. 5,382,429, U.S. Pat. No. 5,503,999, U.S. Pat. No. 5,648,249, U.S. Pat. No. 5,312,912, U.S. Pat. No. 5,498,533, U.S. Pat. No. 5,276,268, U.S. Pat. No. 4,900,676, U.S. Pat. No. 5,633,434 and U.S. Pat. No. 4,970,168.

BUDAPEST TREATY DEPOSIT INFORMATION

A tuber deposit of the J.R. Simplot Company proprietary POTATO CULTIVAR V11 disclosed above and recited in the appended claims has been made with the American Type Culture Collection (ATCC®), 10801 University Boulevard, Manassas, Va. 20110. The date of deposit was Jun. 17, 2015. The deposit of 50 microtubers in 25 vials/two microtubers per vial was taken from the same deposit maintained by J.R. Simplot Company since prior to the filing date of this application. All restrictions will be irrevocably removed upon granting of a patent, and the deposit is intended to meet all of the requirements of 37 C.F.R. §§ 1.801-1.809. The ATCC Accession Number is PTA-122246. The deposit will be maintained in the depository for a period of thirty years, or five years after the last request, or for the enforceable life of the patent, whichever is longer, and will be replaced as necessary during that period.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art in any country in the world.

What is claimed is:

1. A potato tuber, or a part of a tuber, of potato cultivar V11, wherein a representative sample of said tuber was deposited under ATCC Accession No. PTA-122246.

2. A potato plant, or a part thereof, produced by growing the tuber, or a part of the tuber, of claim 1.

3. A potato plant having all of the physiological and morphological characteristics of the plant of claim 2, and comprising the insert region of pSIM1278 that is present in cultivar V11 which contains inverted repeats of potato DNA effective for inhibition of expression of the endogenous asparagine synthetase-1 gene and the endogenous polyphenol oxidase-5 gene in addition to inverted repeats of the endogenous potato promoters for the phosphorylase-L and dikinase R1 genes.

4. A tissue culture of cells produced from the plant of claim 2, wherein said cells of the tissue culture are produced from a plant part selected from the group consisting of leaf, pollen, embryo, cotyledon, hypocotyl, meristematic cell, root, root tip, pistil, anther, flowers, stem and tuber, and wherein said tissue cultured cells comprise the insert region of pSIM1278 that is present in cultivar V11 which contains inverted repeats of potato DNA effective for inhibition of expression of the endogenous asparagine synthetase-1 gene and the endogenous polyphenol oxidase-5 gene in addition to inverted repeats of the endogenous potato promoters for the phosphorylase-L and dikinase R1 genes.

5. A potato plant regenerated from the tissue culture of claim 4, wherein said plant has all of the physiological and morphological characteristics of potato cultivar V11.

6. A potato seed produced by growing the potato tuber, or a part of the tuber, of claim 1, wherein said seed comprises the insert region of pSIM1278 that is present in cultivar V11 which contains inverted repeats of potato DNA effective for inhibition of expression of the endogenous asparagine synthetase-1 gene and the endogenous polyphenol oxidase-5 gene in addition to inverted repeats of the endogenous potato promoters for the phosphorylase-L and dikinase R1 genes.

7. A potato plant, or a part thereof, produced by growing the seed of claim 6.

8. A potato plant regenerated from tissue culture of the potato plant of claim 7, wherein said regenerated plant comprises the insert region of pSIM1278 that is present in cultivar V11 which contains inverted repeats of potato DNA effective for inhibition of expression of the endogenous asparagine synthetase-1 gene and the endogenous polyphenol oxidase-5 gene in addition to inverted repeats of the endogenous potato promoters for the phosphorylase-L and dikinase R1 genes.

9. A method for producing a potato seed, said method comprising crossing two potato plants and harvesting the resultant potato seed, wherein at least one potato plant is the potato plant of claim 2.

10. A method for producing a potato seed, said method comprising crossing two potato plants and harvesting the resultant potato seed, wherein at least one potato plant is the potato plant of claim 7.

11. A potato seed produced by the method of claim 10, wherein said seed comprises the insert region of pSIM1278 that is present in cultivar V11 which contains inverted repeats of potato DNA effective for inhibition of expression of the endogenous asparagine synthetase-1 gene and the endogenous polyphenol oxidase-5 gene in addition to inverted repeats of the endogenous potato promoters for the phosphorylase-L and dikinase R1 genes.

12. A potato plant, or a part thereof, produced by growing said potato seed of claim 11.

13. A potato seed produced from the plant of claim 12, wherein said seed comprises the insert region of pSIM1278 that is present in cultivar V11 which contains inverted repeats of potato DNA effective for inhibition of expression of the endogenous asparagine synthetase-1 gene and the endogenous polyphenol oxidase-5 gene in addition to inverted repeats of the endogenous potato promoters for the phosphorylase-L and dikinase R1 genes.

14. The method of claim 9, wherein one of said potato plants is potato cultivar V11 and the second potato plant is transgenic.

15. A method of producing a potato seed, said method comprising crossing two potato plants and harvesting the resultant potato seed, wherein one of said potato plants is the potato plant of claim 7 and the second potato plant is transgenic.

16. A potato plant, or a part thereof, produced by growing the seed produced by the method of claim 14, wherein said plant comprises the insert region of pSIM1278 that is present in cultivar V11 which contains inverted repeats of potato DNA effective for inhibition of expression of the endogenous asparagine synthetase-1 gene and the endogenous polyphenol oxidase-5 gene in addition to inverted repeats of the endogenous potato promoters for the phosphorylase-L and dikinase R1 genes.

17. A method of introducing a desired trait into potato cultivar V11, wherein the method comprises:
    (a) crossing a V11 plant, wherein a representative sample of tubers was deposited under ATCC Accession No. PTA-122246, with a plant of another potato cultivar that comprises a desired trait to produce progeny plants, wherein the desired trait is selected from the group consisting of male sterility, herbicide resistance, insect resistance, modified fatty acid metabolism, modified carbohydrate metabolism and resistance to bacterial disease, fungal disease or viral disease;
    (b) selecting one or more progeny plants that have the desired trait;
    (c) backcrossing the selected progeny plants with V11 plants to produce backcross progeny plants;
    (d) selecting for backcross progeny plants that have the desired trait; and
    (e) repeating steps (c) and (d) two or more times in succession to produce selected third or higher backcross progeny plants that comprise the desired trait.

18. A potato plant produced by the method of claim 17, wherein the plant has the desired trait and comprises the insert region of pSIM1278 that is present in cultivar V11 which contains inverted repeats of potato DNA effective for inhibition of expression of the endogenous asparagine synthetase-1 gene and the endogenous polyphenol oxidase-5 gene in addition to inverted repeats of the endogenous potato promoters for the phosphorylaseL and dikinase R1 genes.

19. The potato plant of claim 18, wherein the desired trait is herbicide resistance and the resistance is conferred to an herbicide selected from the group consisting of imidazolinone, sulfonylurea, glyphosate, glufosinate, L-phosphinothricin, triazine and benzonitrile.

20. The potato plant of claim 18, wherein the desired trait is insect resistance and the insect resistance is conferred by a transgene encoding a *Bacillus thuringiensis* endotoxin.

21. The potato plant of claim 18, wherein the desired trait is modified fatty acid metabolism or modified carbohydrate metabolism and said desired trait is conferred by a nucleic acid encoding a protein selected from the group consisting of fructosyltransferase, levansucrase, a-amylase, invertase and starch branching enzyme or DNA encoding an antisense of stearyl-ACP desaturase.

22. A method of producing a commodity plant product, comprising obtaining the plant of claim 2, or a part thereof, and producing the commodity plant product from said plant or plant part thereof, wherein said commodity plant product is selected from the group consisting of French fries, potato chips, dehydrated potato material, potato flakes and potato granules.

23. The commodity plant product produced by the method of claim 22, wherein said product comprises the insert region of pSIM1278 that is present in cultivar V11 which contains inverted repeats of potato DNA effective for inhibition of expression of the endogenous asparagine synthetase-1 gene and the endogenous polyphenol oxidase-5 gene in addition to inverted repeats of the endogenous potato promoters for the phosphorylase-L and dikinase R1 genes.

24. A food product made from the potato tuber of claim 1.

25. A food product made from the potato tuber of claim 1, wherein the food product is a sliced potato tuber food product.

26. A food product made from the potato tuber of claim 1, wherein the food product is a French fry or chip.

27. A heat-processed tuber product obtained from the potato tuber of claim 1.

28. A heat-processed tuber product obtained from the potato tuber of claim 1, wherein the heat-processed tuber product is selected from the group consisting of: a French fry, a chip, and a baked potato.

29. A heat-processed tuber product obtained from the potato tuber of claim 1, wherein the heat-processed tuber product is selected from the group consisting of: a French fry, a chip, and a baked potato, wherein the heat-processed tuber product has a concentration of acrylamide that is at least 50% lower, 60% lower, 70% lower, 80% lower, 85% lower, or more, than the concentration of acrylamide of a control heat-processed tuber product that is obtained from a control potato plant that does not comprise the insert region of pSIM1278 that is present in cultivar V11.

\* \* \* \* \*